(12) United States Patent
Ju et al.

(10) Patent No.: US 10,023,855 B2
(45) Date of Patent: Jul. 17, 2018

(54) FUSION PROTEIN COMPRISING C-TERMINAL DOMAIN OF RET PROTEIN AND USE THEREOF AS A DIAGNOSING MARKER

(71) Applicant: MACROGEN INC., Seoul (KR)

(72) Inventors: Young-Seok Ju, Seoul (KR); Jeong-Sun Seo, Seoul (KR); Eun-Hee Kim, Seoul (KR)

(73) Assignees: Macrogen, Inc., Seoul (KR); Macrogen Corp., Rockville, MD (US)

( * ) Notice: Subject to any disclaimer, the term of this patent is extended or adjusted under 35 U.S.C. 154(b) by 269 days.

(21) Appl. No.: 13/663,565

(22) Filed: Oct. 30, 2012

(65) Prior Publication Data

US 2013/0116280 A1    May 9, 2013

Related U.S. Application Data

(60) Provisional application No. 61/553,483, filed on Oct. 31, 2011.

(51) Int. Cl.
| | |
|---|---|
| *C12N 9/96* | (2006.01) |
| *C12Q 1/6886* | (2018.01) |
| *C12N 9/12* | (2006.01) |

(52) U.S. Cl.
CPC ............ *C12N 9/96* (2013.01); *C12N 9/12* (2013.01); *C12Q 1/6886* (2013.01); *C07K 2319/03* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 7,741,034 B2 | 6/2010 | Katz | |
| 2007/0212689 A1 | 9/2007 | Bianchi | |
| 2009/0136502 A1 | 5/2009 | Arai | |
| 2013/0137111 A1 | 5/2013 | Shindo | |
| 2014/0243390 A1* | 8/2014 | Downing et al. ........... | 514/44 A |

FOREIGN PATENT DOCUMENTS

| | | |
|---|---|---|
| WO | 1997-44356 | 11/1997 |
| WO | 2008-031551 | 3/2008 |
| WO | 2013018882 | 2/2013 |

OTHER PUBLICATIONS

Ovary: inv(10)(q11q11) in ovarian germ cell tumors, Atlas Genet Cytogenet Oncol Haematol. 14(8): 2010.*

Zhu et al. The Journal of Clinical Endocrinology & Metabolism 91(9):3603-3610, published online Jun. 13, 2006.*

Cirulli et al., Screening the human exome: a comparison of whole genome and whole transcriptome sequencing Genome Biology 11:R57, May 28, 2010.*

Qi, Xiao-Ping et al. RET Germline Mutations Identified by Exome Sequencing in a Chinese Multiple Endocrine Neoplasia Type 2A/Familial Medullary Thyroid Carcinoma Family. PLoS One 6(5): 1-9, published: May 31, 2011.*

American Society of Clinical Oncology.WHO classification, Chapter 1, Tumours of the lung, p. 10, 2013.*

International Searching Authority, PCT Search Report of PCT/KR2012/009056 (dated Mar. 29, 2013).

Ju, Young Seok et al., "A transforming KIF5B and RET gene fusion in lung adenocarcinoma revealed from whole-genome and transcriptome sequencing," Genome Research, vol. 22, pp. 436-445, ISSN 1088-9051 (Dec. 22, 2011).

Kengo Takeuchi et al: "RET, ROS1 and ALK fusions in lung cancer", Nature Medicine, vol. 18, No. 3, Feb. 12, 2012, pp. 378-381, XP5507734.

Takahashi M et al: "Activation of a novel human transforming gene, ret, by DNA Rearrangement", Cell, Cell Press. US, vol. 42, No. 2, Sep. 1, 1985, pp. 581-588, XP023912622.

Alberti Luisella et al: "RET and NTRK1 proto-oncogenes in human diseases.". Journal of Cellular Physiology, vol. 195, No. 2, May 2003, pp. 168-186, XP002735517.

K.Takeuchi et al: "KIF5B-ALK, a Novel Fusion Oncokinase Identified by an Immunohistochemistry-based Diagnostic System for ALK-positive Lung Cancer", Clinical Cancer Research, vol. 15, No. 9, May 1, 2009, pp. 3143-3149, XP55069999.

The extended European Search report dated Feb. 18, 2015, The Application No. 12845116.8-1402/2773673, Applicant Macrogen Inc.

Andrea Morandi, et al., RET in breast cancer: functional and therapeutic implications., Trends in Molecular Medicine, vol. 17, No. 3, pp. 149-157 (Mar. 2011).

Hitoyasu Futami, et al., A Novel Somatic Point Mutation of the RET Proto-oncogene in Tumor Tissues of Small Cell Lung Cancer Patients, Japanese Journal of Cancer Research, vol. 86, Iss. 12, pp. 1127-1130 (Dec. 1995).

Chmielecki J., et al., "Targeted next-generation sequencing of DNA regions proximal to a conserved GXGXXG signaling motif enables systematic discovery of tyrosine kinase fusions in cancer", Nucleic Acids Research, 38(20): pp. 6985-6996 (Jun. 29, 2010).

Tanizaki J., et al., "Differential roles of trans-phosphorylated EGFR, HER2, HER3, and RET as heterodimerisation partners of MET in lung cancer with MET amplification", British Journal of Cancer 105:pp. 807-813 (Aug. 16, 2011).

* cited by examiner

*Primary Examiner* — Alana Harris Dent

(74) *Attorney, Agent, or Firm* — Lex IP Meister, PLLC

(57) ABSTRACT

A fusion protein including N-terminal domain of a fusion partner at N-terminal and C-terminal domain of RET protein at C-terminal, a fusion gene encoding the fusion protein, and a use of the fusion protein or the fusion gene as a diagnosing marker for a cancer, are provided.

4 Claims, 28 Drawing Sheets

FIG. 27

KIF5B-RETa fusion gene (3123bp; SEQ ID NO: 1; 5'-terminal domain of KIF5B: italic type; 3'-terminal of RET: boldface)
Fusion region (SEQ ID NO: 2; underlined)

*ATGGCGGACCTGGCCGAGTGCAACATCAAAGTGATGTGTCGCTTCAGACCTCTCAACGAGTC
TGAAGTGAACGCGGGCGACAAGTACATCGCCAAGTTTCAGGGGAGGAAGACACGGTCGTGATCG
CGTCCAAGCCTTATGCATTTGATCGGGTGTTCCAGTCAAGCACATCTCAAGAGCAAGTGTATAA
TGACTGTGCAAAGAAGATTGTTAAAGATGTACTTGAAGGATATAATGGAACAATATTTGCATATG
GACAAACATCCTCTGGGAAGACACACACAATGGAGGGTAAACTTCATGATCCAGAAGGCATGG
GAATTATTCCAAGAATAGTGCAAGATATTTTTAATTATATTTACTCCATGGATGAAAATTTGGAATT
TCATATTAAGGTTTCATATTTTGAAATATATTTGGATAAGATAAGGGACCTGTTAGATGTTTCAAAG
ACCAACCTTTCAGTTCATGAAGACAAAAACCGAGTTCCCTATGTAAAGGGGTGCACAGAGCGT
TTTGTATGTAGTCCAGATGAAGTTATGGATACCATAGATGAAGGAAAATCCAACAGACATGTAGC
AGTTACAAATATGAATGAACATAGCTCTAGGAGTCACAGTATATTTCTTATTAATGTCAAACAAGA
GAACACACAAACGGAACAAAAGCTGAGTGGAAAACTTTATCTGGTTGATTTAGCTGGTAGTGAA
AAGGTTAGTAAAACTGGAGCTGAAGGTGCTGTGCTGGATGAAGCTAAAAACATCAACAAGTCA
CTTTCTGCTCTTGGAAATGTTATTTCTGCTTTGGCTGAGGGTAGTACATATGTTCCATATCGAGAT
AGTAAAATGACAAGAATCCTTCAAGATTCATTAGGTGGCAACTGTAGAACCACTATTGTAATTTG
CTGCTCTCCaTCATCATACAATGAGTCTGAAACAAAaTCTACACTCTTATTTGGCCAAaGGGCCa
AAACAATTAAGAAcACAGTTTGTGTCAATGTGGAGTTAACTGCAGAACAGTGGAAAAAGAAGTA
TGAAAAAGAAAAAGAAAAAAATAAGATCCTGCGGAACACTATTCGGTGGCTTGAAAATGAGCTC
AACAGATGGCGTAATGGGGAGACGGTGCCTATTGATGAACAGTTTGACAAAGAGAAAGCCAAC
TTGGAAGCTTTCACAGTGGATAAAGATATTACTCTTACCAATGATAAACCAGCAACCGCAATTGG
AGTTATAGGAAATTTTACTGATGCTGAAAGAAGAAAGTGTGAAGAAGAAATTGCTAAATTATACA
AACAGCTTGATGACAAGGATGAAGAAATTAACCAGCAAAGTCAACTGGTAGAGAAACTGAAGA
CGCAAATGTTGGATCAGGAGGAGCTTTTTGGCATCTACCAGAAGGGATCAAGACAATATGCAAG
CTGAGCTGAATCGCCTTCAAGCAGAAAATGATGCCTCTAAAGAAGAAGTGAAAGAAGTTTTACA
GGCCCTAGAAGAACTTGCTGTCAATTATGATCAGAAGTCTCAGGAAGTTGAAGACAAAACTAAG
GAATATGAATTGCTTAGTGATGAATTGAATCAGAAATGGCAACTTTAGCGAGTATAGATGCTGA
GCTTCAGAAACTTAAGGAAATGACCAACCACCAGAAAAACGAGCAGCTGAGATGATGGCATC
TTTACTAAAGACCTTGCAGAAATAGGAATTGCTGTGGGAAATAATGATGTAAAGCAGCCTGAG
GGAACTGGCATGATAGATGAAGAGTTCACTGTTGCAAGACTCTACATTAGCAAAATGAAGTCAG
AAGTAAAAACCATGGTGAAACGTTGCAAGCAGTTAGAAAGCACACAAACTGAGAGCAACAAAA
AAATGGAAGAAAATGAAAAGGAGTTAGCAGCA*<u>TGTCAGCTTCGTATCTCAAGAGGATCCAA
AGTGGGAATTCCCTCGGAAGAACTTGGTTCTTGGAAAAACTCTAGGAGAAGCCGAATTTCC</u>**C
AAAAGTGGTCAAGGCAACGGCCTTCCATCTGAAAGGCAGAGCAGGGTACACCACGGTGGC
CGTGAAGATGCTGAAAGAGAACGCCTCCCCGAGTGAGCTGCGAGACCTGCTGTCAGAGTTC
AACGTCCTGAAGCAGGTCAACCACCCACATGTCATCAAATTGTATGGGGCCTGCAGCCAGG
ATGGCCCGCTCCTCCTCATCGTGGAGTACGCCAAATACGGCTCCCTGCGGGGCTTCCTCCG
CGAGAGCCGCAAAGTGGGGCCTGGCTACCTGGGCAGTGGAGGCAGCCGCAACTCCAGCTC
CCTGGACCACCCGGATGAGCGGGCCCTCACCATGGGCGACCTCATCTCATTTGCCTGGCAG
ATCTCACAGGGGATGCAGTATCTGGCCGAGATGAAGCTCGTTCATCGGGACTTGGCAGCCA
GAAACATCCTGGTAGCTGAGGGGCGGAAGATGAAGATTTCGGATTTCGGCTTGTCCCGAGAT
GTTTATGAAGAGGATTCCTACGTGAAGAGGAGCCAGGGTCGGATTCCAGTTAAATGGATGGC
AATTGAATCCCTTTTTGATCATATCTACACCACCCAAGTGATGTATGGTCTTTTGGTGTCCTG
CTGTGGGAGATCGTGACCCTAGGGGGAAACCCCTATCCTGGGATTCCTCCTGAGCGGCTCTT
CAACCTTCTGAAGACCGGCCACCGGATGGAGAGGCCAGACAACTGCAGCGAGGAGATGTA
CCGCCTGATGCTGCAATGCTGGAAGCAGGAGCCGGACAAAAGGCCGGTGTTTGCGGACAT
CAGCAAAGACCTGGAGAAGATGATGGTTAAGAGGAGAGACTACTTGGACCTTGCGGCGTCC
ACTCCATCTGACTCCCTGATTTATGACGACGGCCTCTCAGAGGAGGAGACACCGCTGGTGG
ACTGTAATAATGCCCCCTCCCTCGAGCCCTCCCTTCCACATGGATTGAAAACAAACTCTATG
GCATGTCAGACCCGAACTGGCCTGGAGAGAGTCCTGTACCACTCACGAGAGCTGATGGCAC
TAACACTGGGTTTCCAAGATATCCAAATGATAGTGTATATGCTAACTGGATGCTTTCACCCTCA
GCGGCAAAATTAATGGACACGTTTGATAGTTAA**

FIG. 28

KIF5B-RETa fusion protein (1040aa; SEQ ID NO: 3; N-terminal domain of
KIF5B: italic type; C-terminal of RET: boldface)
Fusion region (SEQ ID NO: 4; underlined)

*MADLAECNIKVMCRFRPLNESEVNRGDKYIAKFQGEDTVVIASKPYAFDRVFQSSTSQEQVYNDC
AKKIVKDVLEGYNGTIFAYGQTSSGKTHTMEGKLHDPEGMGIIPRIVQDIFNYIYSMDENLEFHIKVS
YFEIYLDKIRDLLDVSKTNLSVHEDKNRVPYVKGCTERFVCSPDEVMDTIDEGKSNRHVAVTNMNE
HSSRSHSIFLINVKQENTQTEQKLSGKLYLVDLAGSEKVSKTGAEGAVLDEAKNINKSLSALGNVIS
ALAEGSTYVPYRDSKMTRILQDSLGGNCRTTIVICCSPSSYNESETKSTLLFGQRAKTIKNTVCVNV
ELTAEQWKKKYEKEKEKNKILRNTIQVLENELNRWRNGETVPIDEQFDKEKANLEAFTVDKDITLT
NDKPATAIGVIGNFTDAERRKCEEEIAKLYKQLDDKDEEINQQSQLVEKLKTQMLDQEELLASTRR
DQDNMQAELNRLQAENDASKEEVKEVLQALEELAVNYDQKSQEVEDKTKEYELLSDELNQKSAT
LASIDAELQKLKEMTNHQKKRAAEMMASLLKDLAEIGIAVGNNDVKQ*PEGTGMIDEEFTVARLYISK
MKSEVKTMVKRCKQLESTQTESNKKMEENEKELAACQLRISQEDPKWEFPRKNLVLGKTLGEGE
FGKVVKATAFHLKGRAGYTTVAVKMLKENASPSELRDLLSEFNVLKQVNHPHVIKLYGACSQDG
PLLLIVEYAKYGSLRGFLRESRKVGPGYLGSGGSRNSSSLDHPDERALTMGDLISFAWQISQGM
QYLAEMKLVHRDLAARNILVAEGRKMKISDFGLSRDVYEEDSYVKRSQGRIPVKWMAIESLFDHI
YTTQSDVWSFGVLLWEIVTLGGNPYPGIPPERLFNLLKTGHRMERPDNCSEEMYRLMLQCWKQ
EPDKRPVFADISKDLEKMMVKRRDYLDLAASTPSDSLIYDDGLSEEETPLVDCNNAPLPRALPST
WIENKLYGMSDPNWPGESPVPLTRADGTNTGFRYPNDSVYANWMLSPSAAKLMDTFDS**

FIG. 29

KIF5B-RETc fusion gene (2997bp: SEQ ID NO:5; 5'-terminal domain of KIF5B: italic type; 3'-terminal of RET: boldface)
Fusion region (SEQ ID NO: 6; underlined)

*ATGGCGGACCTGGCCGAGTGCAACATCAAAGTGATGTGTCGCTTCAGACCTCTCAACGAGTC
TGAAGTGAACCGCGGCGACAAGTACATCGCCAAGTTTCAGGGAGAAGACACGGTCGTGATCG
CGTCCAAGCCTTATGCATTTGATCGGGTGTTCCAGTCAAGCACATCTCAAGAGCAAGTGTATAA
TGACTGTGCAAAGAAGATTGTTAAAGATGTACTTGAAGGATATAATGGAACAATATTTGCATATG
GACAAACATCCTCTGGGAAGACACACACAATGGAGGGTAAACTTCATGATCCAGAAGGCATGG
GAATTATTCCAAGAATAGTGCAAGATATTTTTAATTATATTTACTCCATGGATGAAAATTTGGAATT
TCATATTAAGGTTTCATATTTTGAAATATATTTGGATAAGATAAGGGACCTGTTAGATGTTTCAAAG
ACCAACCTTTCAGTTCATGAAGACAAAAACCGAGTTCCCTATGTAAAGGGGTGCACAGAGCGT
TTTGTATGTAGTCCAGATGAAGTTATGGATACCATAGATGAAGGAAAATCCAACAGACATGTAGC
AGTTACAAATATGAATGAACATAGCTCTAGGAGTCACAGTATATTTCTTATTAATGTCAAACAAGA
GAACACACAAACGGAACAAAAAGCTGAGTGGAAAACTTTATCTGGTTGATTTAGCTGGTAGTGAA
AAGGTTAGTAAAACTGGAGCTGAAGGTGCTGTGCTGGATGAAGCTAAAAACATCAACAAGTCA
CTTTCTGCTCTTGGAAATGTTATTTCTGCTTTGGCTGAGGGTAGTACATATGTTCCATATCGAGAT
AGTAAAATGACAAGAATCCTTCAAGATTCATTAGGTGGCAACTGTAGAACCACTATTGTAATTTG
CTGCTCTCCaTCATCATACAATGAGTCTGAAACAAAaTCTACACTCTTATTTGGCCAAaGGGCCa
AAACAATTAAGAAcACAGTTTGTGTCAATGTGGAGTTAACTGCAGAACAGTGGAAAAAGAAGTA
TGAAAAAGAAAAAGAAAAAAATAAGATCCTGCGGAACACTATTCAGTGGCTTGAAAATGAGCTC
AACAGATGGCGTAATGGGGAGACGGTGCCTATTGATGAACGATTTGACAAAGAGAAAGCCAAC
TTGGAAGCTTTCACAGTGGATAAAGATATTACTCTTACCAATGATAAACCAGCAACCGCAATTGG
AGTTATAGGAAATTTTACTGATGCTGAAAGAAGAAAGTGTGAAGAAGAAATTGCTAAATTATACA
AACAGCTTGATGACAAGGATGAAGAAATTAACCAGCAAAGTCAACTGGTAGAGAAACTGAAGA
CGCAAATGTTGGATCAGGAGGAGCTTTTTGGCATCTACCAGAAGGGATCAAGACAATATGCAAG
CTGAGCTGAATCGCCTTCAAGCAGAAAATGATGCCTCTAAAGAAGAAGTGAAAGAAGTTTTACA
GGCCCTAGAAGAACTTGCTGTCAATTATGATCAGAAGTCTCAGGAAGTTGAAGACAAAACTAAG
GAATATGAATTGCTTAGTGATGAATTGAATCAGAAATCGGCAACTTTAGCGAGTATAGATGCTGA
GCTTCAGAAACTTAAGGAAATGACCAACCACCAGAAAAACGAGCAGCTGAGATGATGGCATC
TTTACTAAAAGACCTTGCAGAAATAGGAATTGCTGTGGGAAATAATGATGTAAAGCAGCCTGAG
GGAACTGGCATGATAGATGAAGAGTTCACTGTTGCAAGACTCTACATTAGCAAAATGAAGTCAG
AAGTAAAAACCATGGTGAAACGTTGCAAGCAGTTAGAAAGCACACAAACTGAGAGCAACAAAA
AAATGGAAGAAAATGAAAAGGAGTTAGCAGCA*<u>TGTCAGCTTCGTATCTCTCAAGAGGATCCAA
AGTGGGAATTC</u>**CCTCGGAAGAACTTGGTTCTTGGAAAAACTCTAGGAGAAGGCGAATTGG
AAAAGTGGTCAAGCGCAACGGCCTTCCATCTGAAGGCAGAGCAGGGTACACGGCGGTGGC
CGTGAAGATGCTGAAAGAGAACGCTTCCCCGAGTGACTTCGAGACCTGCTGTCACAGTTC
AACGTCCTGAAGCACGGTCAAGCCACCTACATGTCATCAAATTGTATGGGGCCTGCAGCCAGG
ATGGCCCCGCTCCTCCTCATCGTGGAGTACGCCAAATACGGCTCCCTGCGGGGCTTCCTCCG
CGAGAGCCGCAAAGTGGGGCCTGGCTACCTGGGCAGTGGAGGCAGCCGCAACTCCAGCTC
CCTGGACCACCCGGATGAGCGGGCCCTCACCATGGGCGACCTCATCTCATTTGCCTGGCAG
ATCTCACAGGGGATGCAGTATCTGGCCGAGATGAAGCTCGTTCATCGGGACTTGGCAGCCA
GAAACATCCTGGTAGCTGAGGGCCGAAAGATGAAGATTTCGGATTTCGGCTTGTCCCGAGA
TGTTTATGAAGAGGATTCCTACGTGAAGAGGAGCCAGGGTCGGATTCCAGTTAAATGGATG
GCAATTGAATCCCTTTTTGATCATATCTACACCACGCAAAGTGATGTATGGTCTTTTGGTGTC
CTGCTGTGGGAGATCGTGACCCTAGGGGGAAACCCCTATCCTGGGATTCCTCCTGAGCGGC
TCTTCAACCTTCTGAAGACCGGCCACCGGATGGAGAGGCCAGACAACTGCAGCGAGGAGA
TGTACCGCCTGATGCTGCAATGCTGGAAGCAGGAGCCGGACAAAAGGCCCGTGTTTGCGG
ACATCAGCAAAGACCTGGAGAAGATGATGGTTAAGAGGAGAGACTACTGGACCTGCGG
CGTCCACTCCATCTGACTCCCTGATTTATGACGACGCCTCTCAGAGGAGGAGACACCGCT
GGTGGACTGTAATAATGCCCCCCTCCCTCGAGCCCCTCCCTTCCACATGGATTGAAAACAAA
CTCTATGGTAGAATTTCCCATGCATTTACTAGATTCTAG**

FIG. 30

KIF5B-RETc fusion protein (998aa; SEQ ID NO: 7; N-terminal domain of KIF5B: italic type; C-terminal of RET: boldface)
Fusion region (SEQ ID NO:8; underlined)

*MADLAECNIKVMCRFRPLNESEVNRGDKYIAKFQGEDTVVIASKPYAFDRVFQSSTSQEQVYNDC
AKKIVKDVLEGYNGTIFAYGQTSSGKTHTMEGKLHDPEGMGIIPRIVQDIFNYIYSMDENLEFHIKVS
YFEIYLDKIRDLLDVSKTNLSVHEDKNRVPYVKGCTERFVCSPDEVMDTIDEGKSNRHVAVTNMNE
HSSRSHSIFLINVQENTQTEQKLSGKLYLVDLAGSEKVSKTGAEGAVLDEAKNINKSLSALGNVIS
ALAEGSTYVPYRDSKMTRILQDSLGGNCRTTIVICCSPSSYNESETKSTLLFGQRAKTIKNTVCVNV
ELTAEQWKKKYEKEKEKNKILRNTIQWLENELNRWRNGETVPIDEQFDKEKANLEAFTVDKDITLT
NDKPATAIGVIGNFTDAERRKCEEEIAKLYKQLDDKDEEINQQSQLVEKLKTQMLDQEELLASTRR
DQDNMQAELNRLQAENDASKEEVKEVLQALEELAVNYDQKSQEVEDKTKEYELLSDELNQKSAT
LASIDAELQKLKEMTNHQKKRAAEMMASLLKDLAEIGIAVGNNDVKQPEGTGMIDEEFTVARLYISK
MKSEVKTMVKRCKQLESTQTESNKKMEENEKELAA*<u>CQLRSQ</u>**EDPKWEFPRKNLVLGKTLGEGE
FGKVVKATAFHLKGRAGYTTVAVKMLKENASPSELRDLLSEFNVLKQVNHPHVIKLYGACSQDG
PLLLIVEYAKYGSLRGFLRESRKVGPGYLGSGGSRNSSSLDHPDERALTMGDLISFAWQISQGM
QYLAEMKLVHRDLAARNILVAEGRKMKISDFGLSRDVYEEDSYVKRSQGRIPVKWMAIESLFDHI
YTTQSDVWSFGVLLWEIVTLGGNPYPGIPPERLFNLLKTGHRMERPDNCSEEMYRLMLQCWKQ
EPDKRPVFADISKDLEKMMVKRRDYLDLAASTPSDSLIYDDGLSEEETPLVDCNNAPLPRALPST
WIENKLYGRISHAFTRF**

FIG. 31

KIF5B-RETa variant (LC-S2) fusion gene (2934bp; SEQ ID NO 9; 5'-terminal domain of KIF5B: italic type; 3'-terminal of RET: boldface)
Fusion region (SEQ ID NO:10; underlined)

*ATGGCGGACCTGGCCGAGTGCAACATCAAAGTGATGTGTCGCTTCAGACCTCTCAACGAGTC
TGAAGTGAACCGCGGCGACAAGTACATCGCCAAGTTTCAGGGAGAAGACACGGTCGTGATCG
CGTCCAAGCCTTATGCATTTGATCGGGTGTTCCAGTCAAGCACATCTCAAGAGCAAGTGTATA
ATGACTGTGCAAAGAAGATTGTTAAAGATGTACTTGAAGGATATAATGGAACAATATTTGCATA
TGGACAAACATCCTCTGGGAAGACACACACAATGGAGGGTAAACTTCATGATCCAGAAGGCA
TGGGAATTATTCCAAGAATAGTGCAAGATATTTTTAATTATATTTACTCCATGGATGAAAATTTG
GAATTTCATATTAAGGTTTCATATTTTGAAATATATTTGGATAAGATAAGGGACCTGTTAGATGT
TTCAAAGACCAACCTTTCAGTTCATGAAGACAAAAACCGAGTTCCCTATGTAAAGGGGTGCAC
AGAGCGTTTTGTATGTAGTCCAGATGAAGTTATGGATACCATAGATGAAGGAAAATCCAACAG
ACATGTAGCAGTTACAAATATGAATGAACATAGCTCTAGGAGTCACAGTATATTTCTTATTAAT
GTCAAACAAGAGAACACACAAACGGAACAAAAGCTGAGTGGAAAACTTTATCTGGTTGATTTA
GCTGGTAGTGAAAAGGTTAGTAAAACTGGAGCTGAAGGTGCTGTGCTGGATGAAGCTAAAAA
CATCAACAAGTCACTTTCTGCTCTTGGAAATGTTATTTCTGCTTTGGCTGAGGGTAGTACATAT
GTTCCATATCGAGATAGTAAAATGACAAGAATCCTTCAAGATTCATTAGGTGGCAACTGTAGAA
CCACTATTGTAATTTGCTGCTCTCCATCATCATCAATGAGTCTGAAACAAAATCTACACTCTTA
TTTGGCCAAAGGGCCAAAACAATTAAGAACACAGTTTGTGTCAATGTGGAGTTAACTGCAGAA
CAGTGGAAAAGAAGTATGAAAAAGAAAAAGAAAAAAATAAGATCCTGCGGAACACTATTCAG
TGGCTTGAAAATGAGCTCAACAGATGGCGTAATGGGGAGACGGTGCCTATTGATGAACAGTT
TGACAAAGAGAAAGCCAACTTGGAAGCTTTCACAGTGGATAAAGATATTACTCTTACCAATGAT
AAACCAGCAACCGCAATTGGAGTTATAGGAAATTTTACTGATGCTGAAAGAAGAAAGTGTGAA
GAAGAAATTGCTAAATTATACAAACAGCTTGATGACAAGGATGAAGAAATTAACCAGCAAAGTC
AACTGGTAGAGAAACTGAAGACGCAAATGTTGGATCAGGAGGAGCTTTTGGCATCTACCAGA
AGGGATCAAGACAATATGCAAGCTGAGCTGAATCGCCTTCAAGCAGAAAATGATGCCTCTAAA
GAAGAAGTGAAAGAAGTTTTACAGGCCCTAGAAGAACTTGCTGTCAATTATGATCAGAAGTCT
CAGGAAGTTGAAGACAAAACTAAGGAATATGAATTGCTTAGTGATGAATTGAATCAGAAATCG
GCAACTTTAGCGAGTATAGATGCTGAGCTTCAGAAACTTAAGGAAATGACCAACCACCAGAAA
AAACGAGCAGCTGAGATGATGGCATCTTTACTAAAAGACCTTGCAGAAATAGGAATTGCT*<u>GTG
GGAAATAATGATGTAAAGGAGGATCCAAAGTGGGAATTCCCTCGGAAGAACTTGGTTCTTGG</u>
**AAAAACTCTAGGAGAAGGCGAATTTGGAAAGGTGTCAAGGCAACGGCCTTCCATCTGAAA
GGCAGACAGGGTACACCACGGTGGCCGTGAAGATGCTGAAAGAGAACGCCTCCCCGAGT
GAGCTGCGAGACCTGCTGTCAGAGTTCAACGTCCTGAAGCAGGTCAACCACCCACATGTCA
TCAAATTGTATGGGGCCTGCAGCCAGGATGGCCCGCTCCTCCTCATCGTGGAGTACGCCAAA
TACGGCTCCCTGCGGGGCTTCCTCCGCGAGAGCCGCAAAGTGGGGCCTGGCTACCTGGGC
AGTGGAGGCAGCCGCAACTCCAGCTCCCTGGACCACCCGGATGAGCGGGCCCTCACCATG
GGCGACCTCATCTCATTTGCCTGGCAGATCTCACAGGGGATGCAGTATCTGGCCGAGATGAA
GCTCGTTCATCGGGACTTGGCAGCCAGAAACATCCTGGTAGCTGAGGGGCGGAAGATGAAG
ATTTCGGATTTCGGCCTTGTCCCGAGATGTTTATGAAGAGGATTCCTACGTGAAGAGGAGCCA
GGGTCGGATTCCAGTTAAATGGATGGCAATTGAATCCCTTTTTGATCATATCTACACCACGCA
AAGTGATGTATGGTCTTTTGGTGTCCTGCTGTGGGAGATCGTGACCCTAGGGGGAAACCCCT
ATCCTGGGATTCCTCCTGAGCGGCTCTTCAACCTTCTGAAGACCGGCCACCGGATGGAGAG
CCAGACAACTGCAGCGAGGAGATGTACCGCCTGATGCTGCAATGCTGGAAGCAGGAGCC
GGACAAAAGGCCGGTGTTTGCGGACATCAGCAAAGACCTGGAGAAGATGATGGTTAAGAG
GAGAGACTACTTGGACCTTGCGGCGTCCACTCCATCTGACTCCCTGATTTATGACGACGGCC
TCTCAGAGGAGGAGACACCGCTGGTGGACTGTAATAATGCCCCCCTCCCTCGAGCCCTCCC
TTCCACATGGATTGAAAACAAACTCTATGGCAGTGTCAGGACCCGAACTGGCCTGGAGAGAGTC
CTGTACCACTCACGAGAGCTGATGGCACTAACACTGGGTTTCCAAGATATCCAAATGATAGT
GTATATGCTAACTGGATGCTTTCACCCTCAGCGGCAAAATTAATGGACACGTTTGATAGTTAA**

FIG. 32

KIF5B-RETa variant (LC-S2) fusion protein (977aa; SEQ ID NO 11; N-terminal domain of KIF5B: italic type; C-terminal of RET: boldface)
Fusion region (SEQ ID NO:12; underlined)

*MADLAECNIKVMCRFRPLNESEVNRGDKYIAKFQGEDTVVIASKPYAFDRVFQSSTSQEQVYNDC*
*AKKIVKDVLEGYNGTIFAYGQTSSGKTHTMEGKLHDPEGMGIIPRIVQDIFNYIYSMDENLEFHIKVS*
*YFEIYLDKIRDLLDVSKTNLSVHEDKNRVPYVKGCTERFVCSPDEVMDTIDEGKSNRHVAVTNMNE*
*HSSRSHSIFLINVKQENTQTEQKLSGKLYLVDLAGSEKVSKTGAEGAVLDEAKNINKSLSALGNVIS*
*ALAEGSTYVPYRDSKMTRILQDSLGGNCRTTIVICCSPSSYNESETKSTLLFGQRAKTIKNTVCVNV*
*ELTAEQWKKKYEKEKEKNKILRNTIQWLENELNRWRNGETVPIDEQFDKEKANLEAFTVDKDITLT*
*NDKPATAIGVIGNFTDAERRKQEEEIAKLYKQLDDKDEEINQQSQLVEKLKTQMLDQEELLASTRR*
*DQDNMQAELNRLQAENDASKEEVKEVLQALEELAVNYDQKSQEVEDKTKEYELLSDELNQKSAT*
*LASIDAELQKLKEMTNHQKKRAAEMMASLLKDLAEIGIA*<u>VGNNDVKEDPKWE</u>FPRKNLVLGKTLG
EGEFGKVVKATAFHLKGRAGYTTVAVKMLKENASPSELRDLLSEFNVLKQVNHPHVIRLYGACS
QDGPLLLIVEYAKYGSLRGFLRESRKVGPGYLGSGGSRNSSLDHPDERALTMGDLISFAWQIS
QGMQYLAEMKLVHRDLAARNILVAEGRKMKISDFGLSRDVYEEDSYVKRSQGRIPVKWMAIESL
FDHIYTTQSDVWSFGVLLWEIVTLGGNPYPGIPPERLFNLLKTGHRMERPDNCSEEMYRLMLQC
WKQEPDKRPVFADISKDLEKMMVKRRDYLDLAASTPSDSLIYDDGLSEEETPLVDCNRAPLPRA
LPSTWIENKLYGMSDPNWPGESPVPLTRADGTNTGFPRYPNDSVYANWMLSPSAAKLMDTFDS

FIG. 33

KIF5B-RETa variant (LC-S6) fusion gene (3753bp; SEQ ID NO 13; 5'-terminal domain of KiF5B: italic type; 3'-terminal of RET: boldface)
Fusion region (SEQ ID NO:14; underlined)

*ATGGCGGACCTGGCCGAGTGCAACATCAAAGTGATGTGTCGCTTCAGACCTCTCAACGAGTCTGAAGTG
AACCGCGGCGACAAGTACATCGCCAAGTTTCAGGGAGAAGACACGGTCGTGATCGCGTCCAAGCCTTAT
GCATTTGATCGGGTGTTCCAGTCAAGCACATCTCAAGAGCAAGTGTATAATGACTGTGCAAAGAAGATTG
TTAAAGATGTACTTGAAGGATATAATGGAACAATATTTGCATATGGACAAACATCCTCTGGGAAGACACAC
ACAATGGAGGGTAAAACTTCATGATCCAGAAGGCATGGGAATTATTCCAAGAATAGTGCAAGATATTTTTAA
TTATATTTACTCCATGGATGAAAATTTGGAATTTCATATTAAGGTTTCATATTTTGAAATATATTTGGATAAG
ATAAGGGACCTGTTAGATGTTTCAAAGACCAACCTTTCAGTTCATGAAGACAAAACCGAGTTCCCTATGT
AAGGGGTGCACAGAGCGTTTTGTATGTAGTCCAGATGAAGTTATGGATACCATAGATGAAGGAAAATCC
AACAGACATGTAGCAGTTACAAATATGAATGAACATAGCTCTAGGAGTCACAGTATATTTCTTATTAATGT
CAAACAAGAGAACACACAACAACGGAACAAAAGCTGAGTGGAAAACTTTATCTGGTTGATTTAGCTGGTAGT
GAAAAGGTTAGTAAAACTGGAGCTGAAGGTGCTGTGCTGGATGAAGCTAAAAACATCAACAAGTCACTTT
CTGCTCTTGGAAATGTTATTTCTGCTTTGGCTGAGGGTAGTACATATGTTCCATATCGAGATAGTAAAATG
ACAAGAATCCTTCAAGATTCATTAGGTGGCAACTGTAGAACCACTATTGTAATTGCTGCTCTCCATCATC
ATACAATGAGTCTGAAACAAAATCTACACTCTTATTTGGCCAAAGGGCCAAAACAATTAAGAACACAGTTT
GTGTCAATGTGGAGTTAACTGCAGAACAGTGGAAAAAGAAGTATGAAAAAGAAAAAGAAAAAAATAAGAT
CCTGCGGAACACTATTCAGTGGCTTGAAAATGAGCTCAACAGATGGCGTAATGGGGAGACGGTGCCTAT
TGATGAACAGTTTGACAAAGAGAAGCCAACTTGGAAGCTTTCACAGTGGATAAAGATATTACTCTTACCA
ATGATAAACCAGCAACCGCAATTGGAGTTATAGGAAATTTTACTGATGCTGAAAGAAGAAAGTGTGAAGA
AGAAATTGCTAAATTATACAAACAGCTTGATGACAAGGATGAAAGAATTAACCAGCAAAGTCAACTGGTAG
AGAAACTGAAGACGCAAATGTTGGATCAGGAGGAGCTTTTGGCATCTACCAGAAGGGATCAAGACAATAT
GCAAGCTGAGCTGAATCGCCTTCAAGCAGAAAATGATGCCTCTAAAGAAGAAGTGAAAGAAGTTTTACAG
GCCCTAGAAGAACTTGCTGTCAATTATGATCAGAAGTCTCAGGAAGTTGAAGACAAAACTAAGGAATATG
AATTGCTTAGTGATGAATTGAATCAGAAATCGGCAACTTTATCGGAGTATAGATGCTGAGCTTCAGAAACTT
AAGGAAATGACCAACCACCAGAAAAAACGAGCAGCTGAGATGATGGCATCTTTACTAAAAGACCTTGCAG
AAATAGGAATTGCTGTGGGAAATAATGATGTAAAGCAGCCTGAGGGAACTGGCATGATAGATGAAGAGTT
CACTGTTGCAAGACTCTACATTAGCAAAATGAAGTCAGAAGTAAAAACCATGGTGAAACGTTGCAAGCAG
TTAGAAAGCACACAACTGAGAGCAACAAAAAATTGGAAGAAAATGAAAAGGAGTTAGCAGCATGTCAGC
TTCGTATCTCTCAACATGAAGCCAAAATCAAGTGATTGACTGAATACCTTCAAAATGTGGAACAAAAGAAA
AGACAGTTGGAGGAATCTGTCGATGCCCTCAGTGAAGAACTAGTCCAGCTTCGAGCACAAGAGAAAGTC
CATGAAATGGAAAAGGAGCACTTAAATAAGGTTCAGACTGCAAATGAAGTTAAGCAAGCTGTTGAACAGC
AGATCCAGAGCCATAGAGAAACTCATCAAAAACAGATCAGTAGTTTGAGAGATGAAGTAGAAGCAAAAGC
AAAACTTATTACTGATCTTCAAGACCAAAACCAGAAAATGATGTTAGAGCAGGAAACGTCTAAGAGTAGAAC
ATGAAGTTAAAGCCACAGATCAGGAAAAGAGCAGAAAACTACATGAACTTACGGTTATGCAAGATAG
ACGGACAAGCAAGACAAGACTTGAAGGGTTTGGAAGAGACAGTGGCAAAAGAACTTCAGACTTTACA
CAACCTGCGCAAACTCTTTGTTCAGGACCTGGCTACAAGAGTTAAAAAGAGTGCTGAGATTGATTCTGAT
GACACGGAGGCAGCGCTGCTCAGAAGCAAAAATCTCCTTTCTTGAAAATAATCTTGAACAG*<u>CTCACTA
AGTGCAACAAGAGGATCCAAAGTGGGAATT</u>**CCCTCGGAAGAACTTGGTCTTCTTGGAAAACTCTAG
GAGAAGGCGAATTTGGAAAAGTGGTCAAGGCAACGGCCTTCCATCTGAAAGGCAGAGCAGGGTACAC
CACGGTGGCCGTGAAGATGCTGAAAGAGAACGCCTCCCCGAGTGAGCTGCGAGACCTGCTGTCAGAG
TTCAACGTCCTGAAGCAGGTCAACCACCCACATGTCATCAAATTGTATGGGGCCTGCAGCCAGGATGG
CCCGCTCCTCCTCATCGTGGAGTACGCCAAATACGGCTCCCTGCGGGGCTTCCTCCGCGAGAGCCGCA
AAGTGGGGCCTGGCTACCTGGGCAGTGGAGGCAGCCGCAACTCCAGCTCCCTGGACCACCCGGATGA
GCGGGCCCTCACCATGGGCGACCTCATCTCATTTGCCTGGCAGATCTCACAGGGGATGCAGTATCTGG
CCGAGATGAAGCTCGTTCATCGGGACTTGGCAGCCAGAAACATCCTGGTAGCTGAGGGCCGGAAGAT
GAAGATTTCAGACTTTCGCTTGTCCCGAGATGTTTATGAAGAGGATTCCTACGTGAAGAGGAGCCAGGG
TCGGATTCCAGTTAAATGGATGGCAATTGAATCCCTTTTTGATCATATCTACACCACGCAAAGTGATGTAT
GGTCTTTTGGTGTCCTGCTGTGGGAGATCGTGACCCTAGGGGGAAACCCCTATCCTGGGATTCCTCCTG
AGCGGCTCTTCAACCTTCTGAAGACCGGCCACCGGATGGAGAGGCCAGACAACTGCAGCGAGGAGAT
GTACCGCCTGATGCTGCAATGCTGGAAGCAGGAGCCGGACAAAAGGCCGGTGTTCGGACATCAGC
AAAGACCTGGAGAAGATGATGGTTAAGCAGGAAGACCTACTTGGACCTTGCGGCGTCCACTCCATCGA
CTCCCTGATTTATGACGACGGCCTCTCAGAGGAGGAGACACCGCTGGTGGACTGTAATAATGCCCCCCT
CCCTCGAGCCCTCCCTTCCACATGGATTGAAAACAAACTCTATGGCATGTCAGACCCGAACTGGCCTGG
AGAGAGTCCTGTACCACTCACGAGAGCTGATGGCACTAACACTGGGTTTCCAAGATATCCAAATGATAG
TGTATATGCTAACTGGATGCTTTCACCCTCAGCGGCAAAATTAATGGACACGTTTGATAGTTAA**

FIG. 34

KIF5B-RETa variant (LC-S6) fusion protein (1250aa; SEQ ID NO:15; N-terminal domain of KIF5B: italic type; C-terminal of RET: boldface)
Fusion region (SEQ ID NO:16; underlined)

*MADLAECNIKVMCRFRPLNESEVNRGDKYIAKFQGEDTVVIASKPYAFDRVFQSSTSQEQVYNDC
AKKIVKDVLEGYNGTIFAYGQTSSGKTHTMEGKLHDPEGMGIIPRIVQDIFNYIYSMDENLEFHIKVS
YFEIYLDKIRDLLDVSKTNLSVHEDKNRVPYYKGCTERFVCSPDEVMDTIDEGKSNRHVAVTNMNE
HSSRSHSIFLINVKQENTQTEQKLSGKLYLVDLAGSEKVSKTGAEGAVLDEAKNINKSLSALGNVIS
ALAEGSTYYPYRDSKMTRILQDSLGGNCRTTIVICCSPSSYNESETKSTLLFGQRAKTIKNTVCVNV
ELTAEQWKKKYEKEKEKNKILRNTIQWLENELNRWRNGETVPIDEQFDKEKANLEAFTVDKDITLT
NDKPATAIGVIGNFTDAERRKCEEEIAKLYKQLDDKDEEINQQSQLVEKLKTQMLDQEELLASTRR
DQDNMQAELNRLQAENDASKEEVKEVLQALEELAVNYDQKSQEVEDKTKEYELLSDELNQKSAT
LASIDAELQKLKEMTNHQKKRAAEMMASLLKDLAEIGIAVGNNDVKQPEGTGMIDEEFTVARLYISK
MKSEVKTMVKRCKQLESTQTESNKKMEENEKELAACQLRISQHEAKIKSLTEYLQNVEQKKRQLE
ESVDALSEELVQLRAQEKVHEMEKEHLNKVQTANEVKQAVEQQIQSHRETHQKQISSLRDEVEAK
AKLITDLQDQNQKMMLEQERLRVEHEKLKATDQEKSRKLHELTVMQDRREQARQDLKGLEETVA
KELQTLHNLRKLFVQDLATRVKKSAEIDSDDTGGSAAQKQKISFLENNLEQ*<u>LTKVHKQE</u>**DPKWEF
PRKNLVLGKTLGEGEFGKVVKATAFHLKGRAGYTTVAVKMLKENASPSELRDLLSEFNVLKQVN
HPHVIKLYGACSQDGPLLLIVEYAKYGSLRGFLRESRKVGPGYLGSGGSRNSSSLDHPDERALT
MGDLISFAWQISQGMQYLAEMKLVHRDLAARNILVAEGRKMKISDFGLSRDVYEEDSYVKRSQG
RIPVKWMAIESLFDHIYTTQSDVWSFGVLLWEIVTLGGNPYPGIPPERLFNLLKTGHRMERPDNC
SEEMYRLMLQCWKQEPDKRPVFADISKDLEKMMVKRRDYLDLAASTPSDSLIYDDGLSEEETPL
VDCNNAPLPRALPSTWIENKLYGMSDPNWPGESPVPLTRADGTNTGFPRYPNDSVYANWMLSP
SAAKLMDTFDS**

SEQUENCE LISTING

```
<160> NUMBER OF SEQ ID NOS: 22

<210> SEQ ID NO 1
<211> LENGTH: 3123
<212> TYPE: DNA
<213> ORGANISM: Artificial Sequence
<220> FEATURE:
<223> OTHER INFORMATION: KIF5B-RETa fusion gene wherein the KIF5B domain
      is derived from NM_020975

<400> SEQUENCE: 1
atggcggacc tggccgagtg caacatcaaa gtgatgtgtc gcttcagacc tctcaacgag      60
tctgaagtga accgcggcga caagtacatc gccaagtttc agggagaaga cacggtcgtg     120
atcgcgtcca gccttatgc atttgatcgg gtgttccagt caagcacatc tcaagagcaa     180
gtgtataatg actgtgcaaa aagagattgtt aaagatgtac ttgaaggata taatggaaca     240
atatttgcat atggacaaac atcctctggg aagacacaca caatggaggg taaacttcat     300
gatccagaag gcatgggaat tattccaaga atagtgcaag atattttaa ttatatttac     360 tccatggatg aaaatttgga atttcatatt aaggtttcat attttgaaat atatttggat     420
aagataaggg acctgttaga tgtttcaaag accaaccttt cagttcatga agacaaaaac     480
cgagttccct atgtaaaggg gtgcacagag cgttttgtat gtagtccaga tgaagttatg     540
gataccatag atgaaggaaa atccaacaga catgtagcag ttacaaatat gaatgaacat     600
agctctagga gtcacagtat atttcttatt aatgtcaaac aagagaacac acaaacggaa     660
caaaagctga gtggaaaact ttatctggtt gatttagctg gtagtgaaaa ggttagtaaa     720
actggagctg aaggtgctgt gctggatgaa gctaaaaaca tcaacaagtc actttctgct     780
cttggaaatg ttatttctgc tttggctgag ggtagtacat atgttcccata tcgagatagt     840 aaaatgacaa gaatccttca agattcatta ggtggcaact gtagaaccac tattgtaatt     900
tgctgctctc catcatcata caatgagtct gaaacaaat ctacactctt atttggccaa     960
agggccaaaa caattaagaa cacagtttgt gtcaatgtgg agttaactgc agaacagtgg    1020
aaaaagaagt atgaaaaaga aaagaaaaa ataagatcc tgcggaacac tattcagtgg    1080
cttgaaaatg agctcaacag atggcgtaat ggggagacgg tgcctattga tgaacagttt    1140
gacaaagaga agccaacttt ggaagctttc acagtggata agatattac tcttaccaat    1200 gataaaccag caaccgcaat tggagttata ggaaatttta ctgatgctga agaagaaag    1260 tgtgaagaag aaattgctaa attatacaaa cagcttgatg acaaggatga agaaattaac    1320
cagcaaagtc aactggtaga gaaactgaag acgcaaatgt tggatcagga ggagctttg    1380 gcatctacca gaagggatca agacaatatg caagctgagc tgaatcgcct tcaagcagaa    1440
aatgatgcct ctaaagaaga agtgaaagaa gttttacagg ccctagaaga acttgctgtc    1500
aattatgatc agaagtctca ggaagttgaa gacaaaacta aggaatatga attgcttagt    1560
gatgaattga atcagaaat ggcaacttta gcgagtatag atgctgagct tcagaaactt    1620
```

```
aaggaaatga ccaaccacca gaaaaaacga gcagctgaga tgatggcatc tttactaaaa    1680
gaccttgcag aaataggaat tgctgtggga aataatgatg taaagcagcc tgagggaact    1740
ggcatgatag atgaagagtt cactgttgca agactctaca ttagcaaaat gaagtcagaa    1800
gtaaaaacca tggtgaaacg ttgcaagcag ttagaaagca cacaaactga gagcaacaaa    1860
aaaatggaag aaaatgaaaa ggagttagca gcatgtcagc ttcgtatctc tcaagaggat    1920
ccaaagtggg aattccctcg gaagaacttg gttcttggaa aaactctagg agaaggcgaa    1980
tttggaaaag tggtcaaggc aacggccttc catctgaaag gcagagcagg gtacaccacg    2040
gtggccgtga agatgctgaa agagaacgcc tccccgagtg agctgcgaga cctgctgtca    2100
gagttcaacg tcctgaagca ggtcaaccac ccacatgtca tcaaattgta tggggcctgc    2160
agccaggatg gccgctcct cctcatcgtg gagtacgcca aatacggctc cctgcgggc    2220 ttcctccgcg agagccgcaa agtggggcct ggctacctgg gcagtggagg cagccgcaac    2280
tccagctccc tggaccaccc ggatgagcgg gccctcacca tgggcgacct catctcattt    2340
gcctggcaga tctcacaggg gatgcagtat ctggccgaga tgaagctcgt tcatcgggac    2400
ttggcagcca gaaacatcct ggtagctgag gggcggaaga tgaagatttc ggatttcggc    2460
ttgtcccgag atgtttatga agaggattcc tacgtgaaga ggagccaggg tcggattcca    2520
gttaaatgga tggcaattga atccctttt gatcatatct acaccacgca agtgatgta    2580 tggtcttttg gtgtcctgct gtgggagatc gtgaccctag ggggaaaccc ctatcctggg    2640
attcctcctg agcggctctt caaccttctg aagaccggcc accggatgga gaggccagac    2700
aactgcagcg aggagatgta ccgcctgatg ctgcaatgct ggaagcagga gccggacaaa    2760
aggccggtgt ttgcggacat cagcaaagac ctggagaaga tgatggttaa gaggagagac    2820
tacttggacc ttgcggcgtc cactccatct gactccctga tttatgacga cggcctctca    2880
gaggaggaga caccgctggt ggactgtaat aatgcccccc tccctcgagc cctcccttcc    2940
acatggattg aaaacaaact ctatggcatg tcagacccga actggcctgg agagagtcct    3000
gtaccactca cgagagctga tggcactaac actgggtttc caagatatcc aaatgatagt    3060
gtatatgcta actggatgct ttcaccctca gcggcaaaat taatgacac gtttgatagt    3120 taa                                                                 3123
```

<210> SEQ ID NO 2
<211> LENGTH: 42
<212> TYPE: DNA
<213> ORGANISM: Artificial Sequence
<220> FEATURE:
<223> OTHER INFORMATION: Fusion region of KIF5B-RETa fusion gene wherein
      the KIF5B domain is derived from NM_020975

<400> SEQUENCE: 2
tgtcagcttc gtatctctca agaggatcca aagtgggaat tc                        42

<210> SEQ ID NO 3
<211> LENGTH: 1040
<212> TYPE: PRT
<213> ORGANISM: Artificial Sequence
<220> FEATURE:
<223> OTHER INFORMATION: KIF5B-RETa fusion protein wherein the KIF5B
      domain is derived from NM_020975

<400> SEQUENCE: 3

Met Ala Asp Leu Ala Glu Cys Asn Ile Lys Val Met Cys Arg Phe Arg
 1               5                  10                  15

-continued

```
Pro Leu Asn Glu Ser Glu Val Asn Arg Gly Asp Lys Tyr Ile Ala Lys
         20                  25                  30
Phe Gln Gly Glu Asp Thr Val Ile Ala Ser Lys Pro Tyr Ala Phe
         35                  40              45
Asp Arg Val Phe Gln Ser Ser Thr Ser Gln Glu Gln Val Tyr Asn Asp
 50                  55                  60
Cys Ala Lys Lys Ile Val Lys Asp Val Leu Glu Gly Tyr Asn Gly Thr
 65                  70                  75                  80
Ile Phe Ala Tyr Gly Gln Thr Ser Ser Gly Lys Thr His Thr Met Glu
                 85                  90                  95
Gly Lys Leu His Asp Pro Glu Gly Met Gly Ile Ile Pro Arg Ile Val
             100                 105                 110
Gln Asp Ile Phe Asn Tyr Ile Tyr Ser Met Asp Glu Asn Leu Glu Phe
         115                 120                 125
His Ile Lys Val Ser Tyr Phe Glu Ile Tyr Leu Asp Lys Ile Arg Asp
 130                 135                 140
Leu Leu Asp Val Ser Lys Thr Asn Leu Ser Val His Glu Asp Lys Asn
145                 150                 155                 160
Arg Val Pro Tyr Val Lys Gly Cys Thr Glu Arg Phe Val Cys Ser Pro
                 165                 170                 175
Asp Glu Val Met Asp Thr Ile Asp Glu Gly Lys Ser Asn Arg His Val
             180                 185                 190
Ala Val Thr Asn Met Asn Glu His Ser Ser Arg Ser His Ser Ile Phe
         195                 200                 205
Leu Ile Asn Val Lys Gln Glu Asn Thr Gln Thr Glu Gln Lys Leu Ser
 210                 215                 220
Gly Lys Leu Tyr Leu Val Asp Leu Ala Gly Ser Glu Lys Val Ser Lys
225                 230                 235                 240
Thr Gly Ala Glu Gly Ala Val Leu Asp Glu Ala Lys Asn Ile Asn Lys
                 245                 250                 255
Ser Leu Ser Ala Leu Gly Asn Val Ile Ser Ala Leu Ala Glu Gly Ser
             260                 265                 270
Thr Tyr Val Pro Tyr Arg Asp Ser Lys Met Thr Arg Ile Leu Gln Asp
         275                 280                 285
Ser Leu Gly Gly Asn Cys Arg Thr Thr Ile Val Ile Cys Cys Ser Pro
 290                 295                 300
Ser Ser Tyr Asn Glu Ser Glu Thr Lys Ser Thr Leu Leu Phe Gly Gln
305                 310                 315                 320
Arg Ala Lys Thr Ile Lys Asn Thr Val Cys Val Asn Val Glu Leu Thr
                 325                 330                 335
Ala Glu Gln Trp Lys Lys Lys Tyr Glu Lys Glu Lys Glu Lys Asn Lys
             340                 345                 350
Ile Leu Arg Asn Thr Ile Gln Trp Leu Glu Asn Glu Leu Asn Arg Trp
         355                 360                 365
Arg Asn Gly Glu Thr Val Pro Ile Asp Glu Gln Phe Asp Lys Glu Lys
 370                 375                 380
Ala Asn Leu Glu Ala Phe Thr Val Asp Lys Asp Ile Thr Leu Thr Asn
385                 390                 395                 400
Asp Lys Pro Ala Thr Ala Ile Gly Val Ile Gly Asn Phe Thr Asp Ala
                 405                 410                 415
Glu Arg Arg Lys Cys Glu Glu Glu Ile Ala Lys Leu Tyr Lys Gln Leu
             420                 425                 430
```

```
Asp Asp Lys Asp Glu Glu Ile Asn Gln Gln Ser Gln Leu Val Glu Lys
            435                 440                 445
Leu Lys Thr Gln Met Leu Asp Gln Glu Glu Leu Leu Ala Ser Thr Arg
    450                 455                 460
Arg Asp Gln Asp Asn Met Gln Ala Glu Leu Asn Arg Leu Gln Ala Glu
465                 470                 475                 480
Asn Asp Ala Ser Lys Glu Val Lys Glu Val Leu Gln Ala Leu Glu
                485                 490                 495
Glu Leu Ala Val Asn Tyr Asp Gln Lys Ser Gln Glu Val Glu Asp Lys
                500                 505                 510
Thr Lys Glu Tyr Glu Leu Leu Ser Asp Glu Leu Asn Gln Lys Ser Ala
        515                 520                 525
Thr Leu Ala Ser Ile Asp Ala Glu Leu Gln Lys Leu Lys Glu Met Thr
        530                 535                 540
Asn His Gln Lys Lys Arg Ala Ala Glu Met Met Ala Ser Leu Leu Lys
545                 550                 555                 560
Asp Leu Ala Glu Ile Gly Ile Ala Val Gly Asn Asn Asp Val Lys Gln
                565                 570                 575
Pro Glu Gly Thr Gly Met Ile Asp Glu Glu Phe Thr Val Ala Arg Leu
            580                 585                 590
Tyr Ile Ser Lys Met Lys Ser Glu Val Lys Thr Met Val Lys Arg Cys
        595                 600                 605
Lys Gln Leu Glu Ser Thr Gln Thr Glu Ser Asn Lys Lys Met Glu Glu
        610                 615                 620
Asn Glu Lys Glu Leu Ala Ala Cys Gln Leu Arg Ile Ser Gln Glu Asp
625                 630                 635                 640
Pro Lys Trp Glu Phe Pro Arg Lys Asn Leu Val Leu Gly Lys Thr Leu
                645                 650                 655
Gly Glu Gly Glu Phe Gly Lys Val Val Lys Ala Thr Ala Phe His Leu
            660                 665                 670
Lys Gly Arg Ala Gly Tyr Thr Thr Val Ala Val Lys Met Leu Lys Glu
        675                 680                 685
Asn Ala Ser Pro Ser Glu Leu Arg Asp Leu Leu Ser Glu Phe Asn Val
        690                 695                 700
Leu Lys Gln Val Asn His Pro His Val Ile Lys Leu Tyr Gly Ala Cys
705                 710                 715                 720
Ser Gln Asp Gly Pro Leu Leu Leu Ile Val Glu Tyr Ala Lys Tyr Gly
                725                 730                 735
Ser Leu Arg Gly Phe Leu Arg Glu Ser Arg Lys Val Gly Pro Gly Tyr
            740                 745                 750
Leu Gly Ser Gly Gly Ser Arg Asn Ser Ser Leu Asp His Pro Asp
        755                 760                 765
Glu Arg Ala Leu Thr Met Gly Asp Leu Ile Ser Phe Ala Trp Gln Ile
770                 775                 780
Ser Gln Gly Met Gln Tyr Leu Ala Glu Met Lys Leu Val His Arg Asp
785                 790                 795                 800
Leu Ala Ala Arg Asn Ile Leu Val Ala Glu Gly Arg Lys Met Lys Ile
                805                 810                 815
Ser Asp Phe Gly Leu Ser Arg Asp Val Tyr Glu Glu Asp Ser Tyr Val
            820                 825                 830
Lys Arg Ser Gln Gly Arg Ile Pro Val Lys Trp Met Ala Ile Glu Ser
        835                 840                 845
Leu Phe Asp His Ile Tyr Thr Thr Gln Ser Asp Val Trp Ser Phe Gly
```

```
                    850                 855                 860
Val Leu Leu Trp Glu Ile Val Thr Leu Gly Gly Asn Pro Tyr Pro Gly
865                 870                 875                 880

Ile Pro Pro Glu Arg Leu Phe Asn Leu Leu Lys Thr Gly His Arg Met
                885                 890                 895

Glu Arg Pro Asp Asn Cys Ser Glu Glu Met Tyr Arg Leu Met Leu Gln
                900                 905                 910

Cys Trp Lys Gln Glu Pro Asp Lys Arg Pro Val Phe Ala Asp Ile Ser
            915                 920                 925

Lys Asp Leu Glu Lys Met Met Val Lys Arg Arg Asp Tyr Leu Asp Leu
        930                 935                 940

Ala Ala Ser Thr Pro Ser Asp Ser Leu Ile Tyr Asp Asp Gly Leu Ser
945                 950                 955                 960

Glu Glu Glu Thr Pro Leu Val Asp Cys Asn Asn Ala Pro Leu Pro Arg
                965                 970                 975

Ala Leu Pro Ser Thr Trp Ile Glu Asn Lys Leu Tyr Gly Met Ser Asp
                980                 985                 990

Pro Asn Trp Pro Gly Glu Ser Pro Val Pro Leu Thr Arg Ala Asp Gly
            995                 1000                1005

Thr Asn Thr Gly Phe Pro Arg Tyr Pro Asn Asp Ser Val Tyr Ala Asn
    1010                1015                1020

Trp Met Leu Ser Pro Ser Ala Ala Lys Leu Met Asp Thr Phe Asp Ser
1025                1030                1035                1040

<210> SEQ ID NO 4
<211> LENGTH: 14
<212> TYPE: PRT
<213> ORGANISM: Artificial Sequence
<220> FEATURE:
<223> OTHER INFORMATION: Fusion region of KIF5B-RETa fusion protein
      wherein the KIF5B domain is derived from NM_020975

<400> SEQUENCE: 4

Cys Gln Leu Arg Ile Ser Gln Glu Asp Pro Lys Trp Glu Phe
  1               5                  10

<210> SEQ ID NO 5
<211> LENGTH: 2997
<212> TYPE: DNA
<213> ORGANISM: Artificial Sequence
<220> FEATURE:
<223> OTHER INFORMATION: KIF5B-RETc fusion gene wherein the KIF5B domain
      is derived from NM_020630

<400> SEQUENCE: 5
atggcggacc tggccgagtg caacatcaaa gtgatgtgtc gcttcagacc tctcaacgag      60
tctgaagtga accgcggcga caagtacatc gccaagtttc agggagaaga cacggtcgtg     120
atcgcgtcca agcctatgc atttgatcgg gtgttccagt caagcacatc tcaagagcaa     180
gtgtataatg actgtgcaaa gaagattgtt aaagatgtac ttgaaggata taatggaaca     240
atatttgcat atggacaaac atcctctggg aagacacaca atggagggt aaacttcat     300 gatccagaag gcatgggaat tattccaaga atagtgcaag atatttttaa ttatatttac     360
tccatggatg aaaatttgga atttcatatt aaggtttcat attttgaaat atatttggat     420
aagataaggg acctgttaga tgtttcaaag accaaccttt cagttcatga agacaaaaac     480
cgagttccct atgtaaaggg gtgcacagag cgttttgtat gtagtccaga tgaagttatg     540
gataccatag atgaaggaaa atccaacaga catgtagcag ttacaaatat gaatgaacat     600
```

-continued

```
agctctagga gtcacagtat atttcttatt aatgtcaaac aagagaacac acaaacggaa      660
caaaagctga gtggaaaact ttatctggtt gatttagctg gtagtgaaaa ggttagtaaa      720
actggagctg aaggtgctgt gctggatgaa gctaaaaaca tcaacaagtc actttctgct      780
cttggaaatg ttatttctgc tttggctgag ggtagtacat atgttccata tcgagatagt      840
aaaatgacaa gaatccttca agattcatta ggtggcaact gtagaaccac tattgtaatt      900
tgctgctctc catcatcata caatgagtct gaaacaaaat ctacactctt atttggccaa      960
agggccaaaa caattaagaa cacagtttgt gtcaatgtgg agttaactgc agaacagtgg     1020
aaaaagaagt atgaaaaaga aaagaaaaa aataagatcc tgcggaacac tattcagtgg     1080
cttgaaaatg agctcaacag atggcgtaat ggggagacgg tgcctattga tgaacagttt     1140
gacaaagaga aagccaactt ggaagctttc acagtggata agatattac tcttaccaat      1200 gataaaccag caaccgcaat tggagttata ggaaatttta ctgatgctga agaagaaag      1260 tgtgaagaag aaattgctaa attatacaaa cagcttgatg acaaggatga agaaattaac     1320
cagcaaagtc aactggtaga gaaactgaag acgcaaatgt tggatcagga ggagcttttg     1380
gcatctacca gagggatca agacaatatg caagctgagc tgaatcgcct tcaagcagaa     1440
aatgatgcct ctaaagaaga agtgaaagaa gttttacagg ccctagaaga acttgctgtc     1500
aattatgatc agaagtctca ggaagttgaa gacaaaacta aggaatatga attgcttagt     1560
gatgaattga atcagaaatc ggcaactttta gcgagtatag atgctgagct tcagaaactt     1620
aaggaaatga ccaaccacca gaaaaaacga gcagctgaga tgatggcatc tttactaaaa     1680
gaccttgcag aaataggaat tgctgtggga aataatgatg taaagcagcc tgagggaact     1740
ggcatgatag atgaagagtt cactgttgca agactctaca ttagcaaaat gaagtcagaa     1800
gtaaaaacca tggtgaaacg ttgcaagcag ttagaaagca cacaaactga gagcaacaaa     1860
aaaatggaag aaaatgaaaa ggagttagca gcatgtcagc ttcgtatctc tcaagaggat     1920
ccaaagtggg aattccctcg gaagaacttg gttcttggaa aaactctagg agaaggcgaa     1980
tttggaaaag tggtcaaggc aacggccttc atctgaaag gcagagcagg gtacaccacg     2040
gtggccgtga agatgctgaa agagaacgcc tccccgagtg agcttcgaga cctgctgtca     2100
gagttcaacg tcctgaagca ggtcaaccac ccacatgtca tcaaattgta tggggcctgc     2160
agccaggatg gcccgctcct cctcatcgtg gagtacgcca aatacggctc cctgcggggc     2220
ttcctccgcg agagccgcaa agtggggcct ggctacctgg gcagtggagg cagccgcaac     2280
tccagctccc tggaccaccc ggatgagcgg gccctcacca tgggcgacct catctcattt     2340
gcctggcaga tctcacaggg gatgcagtat ctggccgaga tgaagctcgt tcatcgggac     2400
ttggcagcca gaaacatcct ggtagctgag ggcggaaga tgaagatttc ggatttcggc     2460
ttgtcccgag atgtttatga agaggattcc tacgtgaaga ggagccaggg tcggattcca     2520
gttaaatgga tggcaattga atcccttttt gatcatatct acaccacgca agtgatgta      2580 tggtcttttg gtgtcctgct gtgggagatc gtgaccctag ggggaaaccc ctatcctggg     2640
attcctcctg agcggctctt caaccttctg aagaccggcc accggatgga gaggccagac     2700
aactgcagcg aggagatgta ccgcctgatg ctgcaatgct ggaagcagga gccgacaaa      2760 aggccggtgt ttgcggacat cagcaaagac ctggagaaga tgatggttaa gaggagagac     2820
tacttggacc ttgcggcgtc cactccatct gactccctga tttatgacga cggcctctca     2880
gaggaggaga caccgctggt ggactgtaat aatgccccc tccctcgagc cctcccttcc     2940
```

-continued

```
acatggattg aaaacaaact ctatggtaga atttcccatg catttactag attctag        2997
```

<210> SEQ ID NO 6
<211> LENGTH: 42
<212> TYPE: DNA
<213> ORGANISM: Artificial Sequence
<220> FEATURE:
<223> OTHER INFORMATION: Fusion region of KIF5B-RETc fusion gene wherein
the KIF5B Domain is derived from NM_020630

<400> SEQUENCE: 6

```
tgtcagcttc gtatctctca agaggatcca aagtgggaat tc                          42
```

<210> SEQ ID NO 7
<211> LENGTH: 998
<212> TYPE: PRT
<213> ORGANISM: Artificial Sequence
<220> FEATURE:
<223> OTHER INFORMATION: KIF5B-RETc fusion protein wherein the KIF5B
domain is derived from NM_020630

<400> SEQUENCE: 7

```
Met Ala Asp Leu Ala Glu Cys Asn Ile Lys Val Met Cys Arg Phe Arg
  1               5                  10                  15

Pro Leu Asn Glu Ser Glu Val Asn Arg Gly Asp Lys Tyr Ile Ala Lys
             20                  25                  30

Phe Gln Gly Glu Asp Thr Val Val Ile Ala Ser Lys Pro Tyr Ala Phe
         35                  40                  45

Asp Arg Val Phe Gln Ser Ser Thr Ser Gln Glu Gln Val Tyr Asn Asp
     50                  55                  60

Cys Ala Lys Lys Ile Val Lys Asp Val Leu Glu Gly Tyr Asn Gly Thr
 65                  70                  75                  80

Ile Phe Ala Tyr Gly Gln Thr Ser Ser Gly Lys Thr His Thr Met Glu
                 85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285
```

```
Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Lys Asn Lys
                340                 345                 350

Ile Leu Arg Asn Thr Ile Gln Trp Leu Glu Asn Glu Leu Asn Arg Trp
            355                 360                 365

Arg Asn Gly Glu Thr Val Pro Ile Asp Glu Gln Phe Asp Lys Glu Lys
        370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Ile Ala Lys Leu Tyr Lys Gln Leu
                420                 425                 430

Asp Asp Lys Asp Glu Glu Ile Asn Gln Gln Ser Gln Leu Val Glu Lys
            435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
                565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
    610                 615                 620

Asn Glu Lys Glu Leu Ala Ala Cys Gln Leu Arg Ile Ser Gln Glu Asp
625                 630                 635                 640

Pro Lys Trp Glu Phe Pro Arg Lys Asn Leu Val Leu Gly Lys Thr Leu
                645                 650                 655

Gly Glu Gly Glu Phe Gly Lys Val Val Lys Ala Thr Ala Phe His Leu
            660                 665                 670

Lys Gly Arg Ala Gly Tyr Thr Thr Val Ala Val Lys Met Leu Lys Glu
        675                 680                 685

Asn Ala Ser Pro Ser Glu Leu Arg Asp Leu Leu Ser Glu Phe Asn Val
    690                 695                 700
```

```
Leu Lys Gln Val Asn His Pro His Val Ile Lys Leu Tyr Gly Ala Cys
705                 710                 715                 720

Ser Gln Asp Gly Pro Leu Leu Ile Val Glu Tyr Ala Lys Tyr Gly
            725                 730                 735

Ser Leu Arg Gly Phe Leu Arg Glu Ser Arg Lys Val Gly Pro Gly Tyr
            740                 745                 750

Leu Gly Ser Gly Gly Ser Arg Asn Ser Ser Leu Asp His Pro Asp
        755                 760                 765

Glu Arg Ala Leu Thr Met Gly Asp Leu Ile Ser Phe Ala Trp Gln Ile
    770                 775                 780

Ser Gln Gly Met Gln Tyr Leu Ala Glu Met Lys Leu Val His Arg Asp
785                 790                 795                 800

Leu Ala Ala Arg Asn Ile Leu Val Ala Glu Gly Arg Lys Met Lys Ile
            805                 810                 815

Ser Asp Phe Gly Leu Ser Arg Asp Val Tyr Glu Asp Ser Tyr Val
            820                 825                 830

Lys Arg Ser Gln Gly Arg Ile Pro Val Lys Trp Met Ala Ile Glu Ser
        835                 840                 845

Leu Phe Asp His Ile Tyr Thr Thr Gln Ser Asp Val Trp Ser Phe Gly
    850                 855                 860

Val Leu Leu Trp Glu Ile Val Thr Leu Gly Gly Asn Pro Tyr Pro Gly
865                 870                 875                 880

Ile Pro Pro Glu Arg Leu Phe Asn Leu Leu Lys Thr Gly His Arg Met
            885                 890                 895

Glu Arg Pro Asp Asn Cys Ser Glu Glu Met Tyr Arg Leu Met Leu Gln
        900                 905                 910

Cys Trp Lys Gln Glu Pro Asp Lys Arg Pro Val Phe Ala Asp Ile Ser
    915                 920                 925

Lys Asp Leu Glu Lys Met Met Val Lys Arg Arg Asp Tyr Leu Asp Leu
930                 935                 940

Ala Ala Ser Thr Pro Ser Asp Ser Leu Ile Tyr Asp Asp Gly Leu Ser
945                 950                 955                 960

Glu Glu Glu Thr Pro Leu Val Asp Cys Asn Asn Ala Pro Leu Pro Arg
            965                 970                 975

Ala Leu Pro Ser Thr Trp Ile Glu Asn Lys Leu Tyr Gly Arg Ile Ser
        980                 985                 990

His Ala Phe Thr Arg Phe
        995

<210> SEQ ID NO 8
<211> LENGTH: 14
<212> TYPE: PRT
<213> ORGANISM: Artificial Sequence
<220> FEATURE:
<223> OTHER INFORMATION: Fusion region of KIF5B-RETc fusion protein
      wherein the KIF5B domain is derived from NM_020630

<400> SEQUENCE: 8

Cys Gln Leu Arg Ile Ser Gln Glu Asp Pro Lys Trp Glu Phe
  1               5                  10

<210> SEQ ID NO 9
<211> LENGTH: 2934
<212> TYPE: DNA
<213> ORGANISM: Artificial Sequence
<220> FEATURE:
<223> OTHER INFORMATION: KIF5B-RETa variant (LC-S2) fusion gene
```

```
<400> SEQUENCE: 9
atggcggacc tggccgagtg caacatcaaa gtgatgtgtc gcttcagacc tctcaacgag      60
tctgaagtga accgcggcga caagtacatc gccaagtttc agggagaaga cacggtcgtg     120
atcgcgtcca agcctatgc atttgatcgg gtgttccagt caagcacatc tcaagagcaa     180
gtgtataatg actgtgcaaa gaagattgtt aaagatgtac ttgaaggata taatggaaca     240
atatttgcat atggacaaac atcctctggg aagacacaca caatggaggg taaacttcat     300
gatccagaag gcatgggaat tattccaaga atagtgcaag atattttaa ttatatttac     360 tccatggatg aaaatttgga atttcatatt aaggtttcat attttgaaat atatttggat     420
aagataaggg acctgttaga tgtttcaaag accaaccttt cagttcatga agacaaaaac     480
cgagttccct atgtaaaggg gtgcacagag cgttttgtat gtagtccaga tgaagttatg     540
gataccatag atgaaggaaa atccaacaga catgtagcag ttacaaatat gaatgaacat     600
agctctagga gtcacagtat atttcttatt aatgtcaaac aagagaacac acaaacggaa     660
caaaagctga gtggaaaact ttatctggtt gatttagctg gtagtgaaaa ggttagtaaa     720
actggagctg aaggtgctgt gctggatgaa gctaaaaaca tcaacaagtc actttctgct     780
cttggaaatg ttatttctgc tttggctgag ggtagtacat atgttccata tcgagatagt     840
aaaatgacaa gaatccttca agattcatta ggtggcaact gtagaaccac tattgtaatt     900
tgctgctctc catcatcata caatgagtct gaaacaaaat ctacactctt atttggccaa     960
agggccaaaa caattaagaa cacagtttgt gtcaatgtgg agttaactgc agaacagtgg    1020
aaaaagaagt atgaaaaaga aaagaaaaa aataagatcc tgcggaacac tattcagtgg    1080
cttgaaaatg agctcaacag atggcgtaat ggggagacgg tgcctattga tgaacagttt    1140
gacaaagaga aagccaactt ggaagctttc acagtggata agatattac tcttaccaat    1200 gataaaccag caaccgcaat tggagttata ggaaatttta ctgatgctga agaagaaag    1260 tgtgaagaag aaattgctaa attatacaaa cagcttgatg acaaggatga agaaattaac    1320
cagcaaagtc aactggtaga gaaactgaag acgcaaatgt tggatcagga ggagcttttg    1380
gcatctacca aagggatca agacaatatg caagctgagc tgaatcgcct tcaagcagaa    1440
aatgatgcct ctaaagaaga agtgaaagaa gttttacagg ccctagaaga acttgctgtc    1500
aattatgatc agaagtctca ggaagttgaa gacaaaacta aggaatatga attgcttagt    1560
gatgaattga atcagaaatc ggcaactta gcgagtatag atgctgagct tcagaaactt    1620
aaggaaatga ccaaccacca gaaaaaacga gcagctgaga tgatggcatc tttactaaaa    1680
gaccttgcag aaataggaat tgctgtggga ataatgatg taaaggagga tccaaagtgg    1740
gaattccctc ggaagaactt ggttcttgga aaaactctag gagaaggcga atttggaaaa    1800
gtggtcaagg caacggcctt ccatctgaaa ggcagagcag ggtacaccac ggtggccgtg    1860
aagatgctga agagaacgc ctccccgagt gagctgcgag acctgctgtc agagttcaac    1920
gtcctgaagc aggtcaacca cccacatgtc atcaaattgt atgggccctg cagccaggat    1980
ggcccgctcc tcctcatcgt ggagtacgcc aaatacggct ccctgcgggg cttcctccgc    2040
gagagccgca agtggggcc tggctacctg gcagtggag gcagccgcaa ctccagctcc    2100
ctggaccacc cggatgagcg ggccctcacc atgggcgacc tcatctcatt tgcctggcag    2160
atctcacagg ggatgcagta tctggccgag atgaagctcg ttcatcggga cttggcagcc    2220
agaaacatcc tggtagctga ggggcggaag atgaagattt cggatttcgg cttgtcccga    2280
gatgtttatg aagaggattc ctacgtgaag aggagccagg gtcggattcc agttaaatgg    2340
```

-continued

```
atggcaattg aatcccttt tgatcatatc tacaccacgc aaagtgatgt atggtctttt    2400
ggtgtcctgc tgtgggagat cgtgacccta gggggaaacc cctatcctgg gattcctcct    2460
gagcggctct tcaaccttct gaagaccggc caccggatgg agaggccaga caactgcagc    2520
gaggagatgt accgctgat gctgcaatgc tggaagcagg agccggacaa aaggccggtg     2580
tttgcggaca tcagcaaaga cctggagaag atgatggtta agaggagaga ctacttggac    2640
cttgcggcgt ccactccatc tgactccctg atttatgacg acggcctctc agaggaggag    2700
acaccgctgg tggactgtaa taatgccccc ctccctcgag ccctcccttc cacatggatt    2760
gaaaacaaac tctatggcat gtcagacccg aactggcctg agagagtcc tgtaccactc    2820 acgagagctg atggcactaa cactgggttt ccaagatatc caaatgatag tgtatatgct    2880
aactggatgc tttcaccctc agcggcaaaa ttaatggaca cgtttgatag ttaa          2934
```

<210> SEQ ID NO 10
<211> LENGTH: 42
<212> TYPE: DNA
<213> ORGANISM: Artificial Sequence
<220> FEATURE:
<223> OTHER INFORMATION: Fusion region of KIF5B-RETa variant (LC-S2)
      fusion gene

<400> SEQUENCE: 10

```
gtgggaaata atgatgtaaa ggaggatcca aagtgggaat tc                        42
```

<210> SEQ ID NO 11
<211> LENGTH: 977
<212> TYPE: PRT
<213> ORGANISM: Artificial Sequence
<220> FEATURE:
<223> OTHER INFORMATION: KIF5B-RETa variant (LC-S2) fusion protein

<400> SEQUENCE: 11

```
Met Ala Asp Leu Ala Glu Cys Asn Ile Lys Val Met Cys Arg Phe Arg
  1               5                  10                  15

Pro Leu Asn Glu Ser Glu Val Asn Arg Gly Asp Lys Tyr Ile Ala Lys
             20                  25                  30

Phe Gln Gly Glu Asp Thr Val Val Ile Ala Ser Lys Pro Tyr Ala Phe
         35                  40                  45

Asp Arg Val Phe Gln Ser Ser Thr Ser Gln Glu Gln Val Tyr Asn Asp
     50                  55                  60

Cys Ala Lys Lys Ile Val Lys Asp Val Leu Glu Gly Tyr Asn Gly Thr
 65                  70                  75                  80

Ile Phe Ala Tyr Gly Gln Thr Ser Ser Gly Lys Thr His Thr Met Glu
                 85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190
```

```
Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
        290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
        370                 375                 380

Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
                405                 410                 415

Glu Arg Arg Lys Cys Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Glu Leu Leu Ala Ser Thr Arg
    450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
                485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
    530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Glu
                565                 570                 575

Asp Pro Lys Trp Glu Phe Pro Arg Lys Asn Leu Val Leu Gly Lys Thr
            580                 585                 590

Leu Gly Glu Gly Glu Phe Gly Lys Val Val Lys Ala Thr Ala Phe His
        595                 600                 605
```

```
Leu Lys Gly Arg Ala Gly Tyr Thr Thr Val Ala Val Lys Met Leu Lys
    610                 615                 620
Glu Asn Ala Ser Pro Ser Glu Leu Arg Asp Leu Leu Ser Glu Phe Asn
625                 630                 635                 640
Val Leu Lys Gln Val Asn His Pro His Val Ile Lys Leu Tyr Gly Ala
                645                 650                 655
Cys Ser Gln Asp Gly Pro Leu Leu Leu Ile Val Glu Tyr Ala Lys Tyr
            660                 665                 670
Gly Ser Leu Arg Gly Phe Leu Arg Glu Ser Arg Lys Val Gly Pro Gly
        675                 680                 685
Tyr Leu Gly Ser Gly Gly Ser Arg Asn Ser Ser Ser Leu Asp His Pro
    690                 695                 700
Asp Glu Arg Ala Leu Thr Met Gly Asp Leu Ile Ser Phe Ala Trp Gln
705                 710                 715                 720
Ile Ser Gln Gly Met Gln Tyr Leu Ala Glu Met Lys Leu Val His Arg
                725                 730                 735
Asp Leu Ala Ala Arg Asn Ile Leu Val Ala Glu Gly Arg Lys Met Lys
            740                 745                 750
Ile Ser Asp Phe Gly Leu Ser Arg Asp Val Tyr Glu Glu Asp Ser Tyr
        755                 760                 765
Val Lys Arg Ser Gln Gly Arg Ile Pro Val Lys Trp Met Ala Ile Glu
    770                 775                 780
Ser Leu Phe Asp His Ile Tyr Thr Thr Gln Ser Asp Val Trp Ser Phe
785                 790                 795                 800
Gly Val Leu Leu Trp Glu Ile Val Thr Leu Gly Gly Asn Pro Tyr Pro
                805                 810                 815
Gly Ile Pro Pro Glu Arg Leu Phe Asn Leu Leu Lys Thr Gly His Arg
            820                 825                 830
Met Glu Arg Pro Asp Asn Cys Ser Glu Glu Met Tyr Arg Leu Met Leu
        835                 840                 845
Gln Cys Trp Lys Gln Glu Pro Asp Lys Arg Pro Val Phe Ala Asp Ile
    850                 855                 860
Ser Lys Asp Leu Glu Lys Met Met Val Lys Arg Arg Asp Tyr Leu Asp
865                 870                 875                 880
Leu Ala Ala Ser Thr Pro Ser Asp Ser Leu Ile Tyr Asp Asp Gly Leu
                885                 890                 895
Ser Glu Glu Glu Thr Pro Leu Val Asp Cys Asn Asn Ala Pro Leu Pro
            900                 905                 910
Arg Ala Leu Pro Ser Thr Trp Ile Glu Asn Lys Leu Tyr Gly Met Ser
        915                 920                 925
Asp Pro Asn Trp Pro Gly Glu Ser Pro Val Pro Leu Thr Arg Ala Asp
    930                 935                 940
Gly Thr Asn Thr Gly Phe Pro Arg Tyr Pro Asn Asp Ser Val Tyr Ala
945                 950                 955                 960
Asn Trp Met Leu Ser Pro Ser Ala Ala Lys Leu Met Asp Thr Phe Asp
                965                 970                 975
Ser

<210> SEQ ID NO 12
<211> LENGTH: 14
<212> TYPE: PRT
<213> ORGANISM: Artificial Sequence
<220> FEATURE:
<223> OTHER INFORMATION: Fusion region of KIF5B-RETa variant (LC-S2)
      fusion protein
```

<400> SEQUENCE: 12

Val Gly Asn Asn Asp Val Lys Glu Asp Pro Lys Trp Glu Phe
 1               5                   10

<210> SEQ ID NO 13
<211> LENGTH: 3753
<212> TYPE: DNA
<213> ORGANISM: Artificial Sequence
<220> FEATURE:
<223> OTHER INFORMATION: KIF5B-RETa variant (LC-S6) fusion gene

<400> SEQUENCE: 13

| | | | | | | |
|---|---|---|---|---|---|---|
| atggcggacc | tggccgagtg | caacatcaaa | gtgatgtgtc | gcttcagacc | tctcaacgag | 60 |
| tctgaagtga | accgcggcga | caagtacatc | gccaagtttc | agggagaaga | cacggtcgtg | 120 |
| atcgcgtcca | agccttatgc | atttgatcgg | gtgttccagt | caagcacatc | tcaagagcaa | 180 |
| gtgtataatg | actgtgcaaa | gaagattgtt | aaagatgtac | ttgaaggata | taatggaaca | 240 |
| atatttgcat | atggacaaac | atcctctggg | aagacacaca | caatggaggg | taaacttcat | 300 |
| gatccagaag | gcatgggaat | tattccaaga | atagtgcaag | atattttta | ttatatttac | 360 |
| tccatggatg | aaaatttgga | atttcatatt | aaggtttcat | attttgaaat | atatttggat | 420 |
| aagataaggg | acctgttaga | tgtttcaaag | accaaccttt | cagttcatga | agacaaaaac | 480 |
| cgagttccct | atgtaaaggg | gtgcacagag | cgttttgtat | gtagtccaga | tgaagttatg | 540 |
| gataccatag | atgaaggaaa | atccaacaga | catgtagcag | ttacaaatat | gaatgaacat | 600 |
| agctctagga | gtcacagtat | atttcttatt | aatgtcaaac | aagagaacac | acaaacggaa | 660 |
| caaaagctga | gtggaaaact | ttatctggtt | gatttagctg | gtagtgaaaa | ggttagtaaa | 720 |
| actggagctg | aaggtgctgt | gctggatgaa | gctaaaaaca | tcaacaagtc | actttctgct | 780 |
| cttggaaatg | ttatttctgc | tttggctgag | ggtagtacat | atgttccata | tcgagatagt | 840 |
| aaaatgacaa | gaatccttca | agattcatta | ggtggcaact | gtagaaccac | tattgtaatt | 900 |
| tgctgctctc | catcatcata | caatgagtct | gaaacaaaat | ctacactctt | atttggccaa | 960 |
| agggccaaaa | caattaagaa | cacagtttgt | gtcaatgtgg | agttaactgc | agaacagtgg | 1020 |
| aaaaagaagt | atgaaaaaga | aaagaaaaa | aataagatcc | tgcggaacac | tattcagtgg | 1080 |
| cttgaaaatg | agctcaacag | atggcgtaat | ggggagacgg | tgcctattga | tgaacagttt | 1140 |
| gacaaagaga | agccaacttt | ggaagctttc | acagtggata | agatattac | tcttaccaat | 1200 |
| gataaaccag | caaccgcaat | tggagttata | ggaaatttta | ctgatgctga | agaagaaag | 1260 |
| tgtgaagaag | aaattgctaa | attatacaaa | cagcttgatg | acaaggatga | agaaattaac | 1320 |
| cagcaaagtc | aactggtaga | gaaactgaag | acgcaaatgt | tggatcagga | ggagcttttg | 1380 |
| gcatctacca | gaagggatca | agacaatatg | caagctgagc | tgaatcgcct | tcaagcagaa | 1440 |
| aatgatgcct | ctaaagaaga | agtgaaagaa | gttttacagg | ccctagaaga | acttgctgtc | 1500 |
| aattatgatc | agaagtctca | ggaagttgaa | gacaaaacta | ggaatatga | attgcttagt | 1560 |
| gatgaattga | atcagaaatc | ggcaacttta | gcgagtatag | atgctgagct | tcagaaactt | 1620 |
| aaggaaatga | ccaaccacca | gaaaaaacga | gcagctgaga | tgatggcatc | tttactaaaa | 1680 |
| gaccttgcag | aaataggaat | tgctgtggga | ataatgatg | taaagcagcc | tgagggaact | 1740 |
| ggcatgatag | atgaagagtt | cactgttgca | gactctaca | ttagcaaaat | gaagtcagaa | 1800 |
| gtaaaaacca | tggtgaaacg | ttgcaagcag | ttagaaagca | cacaaactga | gcaacaaaa | 1860 |
| aaaatggaag | aaaatgaaaa | ggagttagca | gcatgtcagc | ttcgtatctc | tcaacatgaa | 1920 |

```
gccaaaatca agtcattgac tgaatacctt caaaatgtgg aacaaaagaa aagacagttg      1980
gaggaatctg tcgatgccct cagtgaagaa ctagtccagc ttcgagcaca agagaaagtc      2040
catgaaatgg aaaaggagca cttaaataag gttcagactg caaatgaagt taagcaagct      2100
gttgaacagc agatccagag ccatagaaaa actcatcaaa aacagatcag tagttttgaga     2160 gatgaagtag aagcaaaagc aaaacttatt actgatcttc aagaccaaaa ccagaaaatg      2220
atgttagagc aggaacgtct aagagtagaa catgagaagt tgaaagccac agatcaggaa      2280
aagagcagaa aactacatga acttacggtt atgcaagata gacgagaaca agcaagacaa      2340
gacttgaagg gtttggaaga gacagtggca aagaacttc agactttaca caacctgcgc       2400
aaactctttg ttcaggacct ggctacaaga gttaaaaaga gtgctgagat tgattctgat      2460
gacaccggag gcagcgctgc tcagaagcaa aaaatctcct ttcttgaaaa taatcttgaa      2520
cagctcacta aagtgcacaa acaggaggat ccaaagtggg aattccctcg aagaacttg       2580 gttcttggaa aaactctagg agaaggcgaa tttggaaaag tggtcaaggc aacggccttc      2640
catctgaaag gcagagcagg gtacaccacg gtggccgtga agatgctgaa agagaacgcc      2700
tccccgagtg agctgcgaga cctgctgtca gagttcaacg tcctgaagca ggtcaaccac      2760
ccacatgtca tcaaattgta tgggccctgc agccaggatg gcccgctcct cctcatcgtg      2820
gagtacgcca aatacggctc cctgcggggc ttcctccgcg agagccgcaa agtgggccct      2880
ggctacctgg gcagtggagg cagccgcaac tccagctccc tggaccaccc ggatgagcgg      2940
gccctcacca tgggcgacct catctcattt gcctggcaga tctcacaggg gatgcagtat      3000
ctggccgaga tgaagctcgt tcatcgggac ttggcagcca gaaacatcct ggtagctgag      3060
gggcggaaga tgaagatttc ggatttcggc ttgtcccgag atgtttatga agaggattcc      3120
tacgtgaaga ggagccaggg tcggattcca gttaaatgga tggcaattga atccctttt       3180 gatcatatct acaccacgca agtgatgta tggtcttttg gtgtcctgct gtgggagatc       3240
gtgaccctag ggggaaaccc ctatcctggg attcctcctg agcggctctt caaccttctg      3300
aagaccggcc accggatgga gaggccagac aactgcagcg aggagatgta ccgcctgatg      3360
ctgcaatgct ggaagcagga gccggacaaa aggccggtgt tgcggacat cagcaaagac       3420 ctggagaaga tgatggttaa gaggagagac tacttggacc ttgcggcgtc cactccatct      3480
gactccctga tttatgacga cggcctctca gaggaggaga caccgctggt ggactgtaat      3540
aatgcccccc tccctcgagc cctcccttcc acatggattg aaaacaaact ctatggcatg      3600
tcagacccga ctggcctgg agagagtcct gtaccactca cgagagctga tggcactaac      3660
actgggtttc caagatatcc aaatgatagt gtatatgcta actggatgct ttcaccctca      3720
gcggcaaaat taatgaccac gtttgatagt taa                                   3753
```

<210> SEQ ID NO 14
<211> LENGTH: 42
<212> TYPE: DNA
<213> ORGANISM: Artificial Sequence
<220> FEATURE:
<223> OTHER INFORMATION: Fusion region of KIF5B-RETa variant (LC-S6)
      fusion gene

<400> SEQUENCE: 14
ctcactaaag tgcacaaaca ggaggatcca agtgggaat tc                          42

<210> SEQ ID NO 15
<211> LENGTH: 1250

<212> TYPE: PRT
<213> ORGANISM: Artificial Sequence
<220> FEATURE:
<223> OTHER INFORMATION: KIF5B-RETa variant (LC-S6) fusion protein

<400> SEQUENCE: 15

```
Met Ala Asp Leu Ala Glu Cys Asn Ile Lys Val Met Cys Arg Phe Arg
 1               5                  10                  15

Pro Leu Asn Glu Ser Glu Val Asn Arg Gly Asp Lys Tyr Ile Ala Lys
            20                  25                  30

Phe Gln Gly Glu Asp Thr Val Val Ile Ala Ser Lys Pro Tyr Ala Phe
        35                  40                  45

Asp Arg Val Phe Gln Ser Thr Ser Gln Glu Gln Val Tyr Asn Asp
50                  55                  60

Cys Ala Lys Lys Ile Val Lys Asp Val Leu Glu Gly Tyr Asn Gly Thr
65                  70                  75                  80

Ile Phe Ala Tyr Gly Gln Thr Ser Ser Gly Lys Thr His Thr Met Glu
                85                  90                  95

Gly Lys Leu His Asp Pro Glu Gly Met Gly Ile Ile Pro Arg Ile Val
            100                 105                 110

Gln Asp Ile Phe Asn Tyr Ile Tyr Ser Met Asp Glu Asn Leu Glu Phe
        115                 120                 125

His Ile Lys Val Ser Tyr Phe Glu Ile Tyr Leu Asp Lys Ile Arg Asp
    130                 135                 140

Leu Leu Asp Val Ser Lys Thr Asn Leu Ser Val His Glu Asp Lys Asn
145                 150                 155                 160

Arg Val Pro Tyr Val Lys Gly Cys Thr Glu Arg Phe Val Cys Ser Pro
                165                 170                 175

Asp Glu Val Met Asp Thr Ile Asp Glu Gly Lys Ser Asn Arg His Val
            180                 185                 190

Ala Val Thr Asn Met Asn Glu His Ser Ser Arg Ser His Ser Ile Phe
        195                 200                 205

Leu Ile Asn Val Lys Gln Glu Asn Thr Gln Thr Glu Gln Lys Leu Ser
    210                 215                 220

Gly Lys Leu Tyr Leu Val Asp Leu Ala Gly Ser Glu Lys Val Ser Lys
225                 230                 235                 240

Thr Gly Ala Glu Gly Ala Val Leu Asp Glu Ala Lys Asn Ile Asn Lys
                245                 250                 255

Ser Leu Ser Ala Leu Gly Asn Val Ile Ser Ala Leu Ala Glu Gly Ser
            260                 265                 270

Thr Tyr Val Pro Tyr Arg Asp Ser Lys Met Thr Arg Ile Leu Gln Asp
        275                 280                 285

Ser Leu Gly Gly Asn Cys Arg Thr Thr Ile Val Ile Cys Cys Ser Pro
    290                 295                 300

Ser Ser Tyr Asn Glu Ser Glu Thr Lys Ser Thr Leu Leu Phe Gly Gln
305                 310                 315                 320

Arg Ala Lys Thr Ile Lys Asn Thr Val Cys Val Asn Val Glu Leu Thr
                325                 330                 335

Ala Glu Gln Trp Lys Lys Lys Tyr Glu Lys Glu Lys Glu Lys Asn Lys
            340                 345                 350

Ile Leu Arg Asn Thr Ile Gln Trp Leu Glu Asn Glu Leu Asn Arg Trp
        355                 360                 365

Arg Asn Gly Glu Thr Val Pro Ile Asp Glu Gln Phe Asp Lys Glu Lys
    370                 375                 380
```

-continued

```
Ala Asn Leu Glu Ala Phe Thr Val Asp Lys Asp Ile Thr Leu Thr Asn
385                 390                 395                 400

Asp Lys Pro Ala Thr Ala Ile Gly Val Ile Gly Asn Phe Thr Asp Ala
            405                 410                 415

Glu Arg Arg Lys Cys Glu Glu Ile Ala Lys Leu Tyr Lys Gln Leu
            420                 425                 430

Asp Asp Lys Asp Glu Glu Ile Asn Gln Gln Ser Gln Leu Val Glu Lys
        435                 440                 445

Leu Lys Thr Gln Met Leu Asp Gln Glu Leu Leu Ala Ser Thr Arg
        450                 455                 460

Arg Asp Gln Asp Asn Met Gln Ala Glu Leu Asn Arg Leu Gln Ala Glu
465                 470                 475                 480

Asn Asp Ala Ser Lys Glu Glu Val Lys Glu Val Leu Gln Ala Leu Glu
            485                 490                 495

Glu Leu Ala Val Asn Tyr Asp Gln Lys Ser Gln Glu Val Glu Asp Lys
            500                 505                 510

Thr Lys Glu Tyr Glu Leu Leu Ser Asp Glu Leu Asn Gln Lys Ser Ala
        515                 520                 525

Thr Leu Ala Ser Ile Asp Ala Glu Leu Gln Lys Leu Lys Glu Met Thr
        530                 535                 540

Asn His Gln Lys Lys Arg Ala Ala Glu Met Met Ala Ser Leu Leu Lys
545                 550                 555                 560

Asp Leu Ala Glu Ile Gly Ile Ala Val Gly Asn Asn Asp Val Lys Gln
            565                 570                 575

Pro Glu Gly Thr Gly Met Ile Asp Glu Glu Phe Thr Val Ala Arg Leu
            580                 585                 590

Tyr Ile Ser Lys Met Lys Ser Glu Val Lys Thr Met Val Lys Arg Cys
        595                 600                 605

Lys Gln Leu Glu Ser Thr Gln Thr Glu Ser Asn Lys Lys Met Glu Glu
        610                 615                 620

Asn Glu Lys Glu Leu Ala Ala Cys Gln Leu Arg Ile Ser Gln His Glu
625                 630                 635                 640

Ala Lys Ile Lys Ser Leu Thr Glu Tyr Leu Gln Asn Val Glu Gln Lys
            645                 650                 655

Lys Arg Gln Leu Glu Glu Ser Val Asp Ala Leu Ser Glu Glu Leu Val
            660                 665                 670

Gln Leu Arg Ala Gln Glu Lys Val His Glu Met Glu Lys Glu His Leu
        675                 680                 685

Asn Lys Val Gln Thr Ala Asn Glu Val Lys Gln Ala Val Glu Gln Gln
        690                 695                 700

Ile Gln Ser His Arg Glu Thr His Gln Lys Gln Ile Ser Ser Leu Arg
705                 710                 715                 720

Asp Glu Val Glu Ala Lys Ala Lys Leu Ile Thr Asp Leu Gln Asp Gln
            725                 730                 735

Asn Gln Lys Met Met Leu Glu Gln Glu Arg Leu Arg Val Glu His Glu
        740                 745                 750

Lys Leu Lys Ala Thr Asp Gln Glu Lys Ser Arg Lys Leu His Glu Leu
        755                 760                 765

Thr Val Met Gln Asp Arg Arg Glu Gln Ala Arg Gln Asp Leu Lys Gly
        770                 775                 780

Leu Glu Glu Thr Val Ala Lys Glu Leu Gln Thr Leu His Asn Leu Arg
785                 790                 795                 800

Lys Leu Phe Val Gln Asp Leu Ala Thr Arg Val Lys Lys Ser Ala Glu
```

-continued

```
                805                 810                 815
Ile Asp Ser Asp Asp Thr Gly Gly Ser Ala Ala Gln Lys Gln Lys Ile
            820                 825                 830

Ser Phe Leu Glu Asn Asn Leu Glu Gln Leu Thr Lys Val His Lys Gln
            835                 840                 845

Glu Asp Pro Lys Trp Glu Phe Pro Arg Lys Asn Leu Val Leu Gly Lys
        850                 855                 860

Thr Leu Gly Glu Gly Glu Phe Gly Lys Val Val Lys Ala Thr Ala Phe
865                 870                 875                 880

His Leu Lys Gly Arg Ala Gly Tyr Thr Thr Val Ala Val Lys Met Leu
            885                 890                 895

Lys Glu Asn Ala Ser Pro Ser Glu Leu Arg Asp Leu Leu Ser Glu Phe
            900                 905                 910

Asn Val Leu Lys Gln Val Asn His Pro His Val Ile Lys Leu Tyr Gly
            915                 920                 925

Ala Cys Ser Gln Asp Gly Pro Leu Leu Leu Ile Val Glu Tyr Ala Lys
            930                 935                 940

Tyr Gly Ser Leu Arg Gly Phe Leu Arg Glu Ser Arg Lys Val Gly Pro
945                 950                 955                 960

Gly Tyr Leu Gly Ser Gly Ser Arg Asn Ser Ser Leu Asp His
            965                 970                 975

Pro Asp Glu Arg Ala Leu Thr Met Gly Asp Leu Ile Ser Phe Ala Trp
            980                 985                 990

Gln Ile Ser Gln Gly Met Gln Tyr Leu Ala Glu Met Lys Leu Val His
            995                 1000                1005

Arg Asp Leu Ala Ala Arg Asn Ile Leu Val Ala Glu Gly Arg Lys Met
    1010                1015                1020

Lys Ile Ser Asp Phe Gly Leu Ser Arg Asp Val Tyr Glu Glu Asp Ser
1025                1030                1035                1040

Tyr Val Lys Arg Ser Gln Gly Arg Ile Pro Val Lys Trp Met Ala Ile
            1045                1050                1055

Glu Ser Leu Phe Asp His Ile Tyr Thr Thr Gln Ser Asp Val Trp Ser
        1060                1065                1070

Phe Gly Val Leu Leu Trp Glu Ile Val Thr Leu Gly Gly Asn Pro Tyr
        1075                1080                1085

Pro Gly Ile Pro Pro Glu Arg Leu Phe Asn Leu Leu Lys Thr Gly His
        1090                1095                1100

Arg Met Glu Arg Pro Asp Asn Cys Ser Glu Glu Met Tyr Arg Leu Met
1105                1110                1115                1120

Leu Gln Cys Trp Lys Gln Glu Pro Asp Lys Arg Pro Val Phe Ala Asp
            1125                1130                1135

Ile Ser Lys Asp Leu Glu Lys Met Met Val Lys Arg Arg Asp Tyr Leu
            1140                1145                1150

Asp Leu Ala Ala Ser Thr Pro Ser Asp Ser Leu Ile Tyr Asp Asp Gly
        1155                1160                1165

Leu Ser Glu Glu Glu Thr Pro Leu Val Asp Cys Asn Asn Ala Pro Leu
1170                1175                1180

Pro Arg Ala Leu Pro Ser Thr Trp Ile Glu Asn Lys Leu Tyr Gly Met
1185                1190                1195                1200

Ser Asp Pro Asn Trp Pro Gly Glu Ser Pro Val Pro Leu Thr Arg Ala
        1205                1210                1215

Asp Gly Thr Asn Thr Gly Phe Pro Arg Tyr Pro Asn Asp Ser Val Tyr
        1220                1225                1230
```

```
Ala Asn Trp Met Leu Ser Pro Ser Ala Ala Lys Leu Met Asp Thr Phe
        1235                1240                1245

Asp Ser
  1250

<210> SEQ ID NO 16
<211> LENGTH: 14
<212> TYPE: PRT
<213> ORGANISM: Artificial Sequence
<220> FEATURE:
<223> OTHER INFORMATION: Fusion region of KIF5B-RETa variant (LC-S6)
      fusion protein

<400> SEQUENCE: 16

Leu Thr Lys Val His Lys Gln Glu Asp Pro Lys Trp Glu Phe
1               5                   10

<210> SEQ ID NO 17
<211> LENGTH: 310
<212> TYPE: PRT
<213> ORGANISM: Artificial Sequence
<220> FEATURE:
<223> OTHER INFORMATION: coiled coil domain of KIF5B protein encoded by
      NM_004521

<400> SEQUENCE: 17

Val Cys Val Asn Val Glu Leu Thr Ala Glu Gln Trp Lys Lys Tyr
1               5                   10                  15

Glu Lys Glu Lys Glu Lys Asn Lys Ile Leu Arg Asn Thr Ile Gln Trp
            20                  25                  30

Leu Glu Asn Glu Leu Asn Arg Trp Arg Asn Gly Glu Thr Val Pro Ile
        35                  40                  45

Asp Glu Gln Phe Asp Lys Glu Lys Ala Asn Leu Glu Ala Phe Thr Val
    50                  55                  60

Asp Lys Asp Ile Thr Leu Thr Asn Asp Lys Pro Ala Thr Ala Ile Gly
65                  70                  75                  80

Val Ile Gly Asn Phe Thr Asp Ala Glu Arg Arg Lys Cys Glu Glu Glu
                85                  90                  95

Ile Ala Lys Leu Tyr Lys Gln Leu Asp Asp Lys Asp Glu Glu Ile Asn
            100                 105                 110

Gln Gln Ser Gln Leu Val Glu Lys Leu Lys Thr Gln Met Leu Asp Gln
        115                 120                 125

Glu Glu Leu Leu Ala Ser Thr Arg Arg Asp Gln Asp Asn Met Gln Ala
    130                 135                 140

Glu Leu Asn Arg Leu Gln Ala Glu Asn Asp Ala Ser Lys Glu Glu Val
145                 150                 155                 160

Lys Glu Val Leu Gln Ala Leu Glu Glu Leu Ala Val Asn Tyr Asp Gln
                165                 170                 175

Lys Ser Gln Glu Val Glu Asp Lys Thr Lys Glu Tyr Glu Leu Leu Ser
            180                 185                 190

Asp Glu Leu Asn Gln Lys Ser Ala Thr Leu Ala Ser Ile Asp Ala Glu
        195                 200                 205

Leu Gln Lys Leu Lys Glu Met Thr Asn His Gln Lys Lys Arg Ala Ala
    210                 215                 220

Glu Met Met Ala Ser Leu Leu Lys Asp Leu Ala Glu Ile Gly Ile Ala
225                 230                 235                 240

Val Gly Asn Asn Asp Val Lys Gln Pro Glu Gly Thr Gly Met Ile Asp
                245                 250                 255
```

Glu Glu Phe Thr Val Ala Arg Leu Tyr Ile Ser Lys Met Lys Ser Glu
            260                 265                 270

Val Lys Thr Met Val Lys Arg Cys Lys Gln Leu Glu Ser Thr Gln Thr
        275                 280                 285

Glu Ser Asn Lys Lys Met Glu Glu Asn Glu Lys Glu Leu Ala Ala Cys
    290                 295                 300

Gln Leu Arg Ile Ser Gln
305                 310

<210> SEQ ID NO 18
<211> LENGTH: 22
<212> TYPE: DNA
<213> ORGANISM: Artificial Sequence
<220> FEATURE:
<223> OTHER INFORMATION: primer for detecting the inversion of
      Chromosome 10

<400> SEQUENCE: 18
cagaatttca caaggaggga ag                                              22

<210> SEQ ID NO 19
<211> LENGTH: 22
<212> TYPE: DNA
<213> ORGANISM: Artificial Sequence
<220> FEATURE:
<223> OTHER INFORMATION: primer for detecting the inversion of
      Chromosome 10

<400> SEQUENCE: 19
caggacctct gactacagtg ga                                              22

<210> SEQ ID NO 20
<211> LENGTH: 22
<212> TYPE: DNA
<213> ORGANISM: Artificial Sequence
<220> FEATURE:
<223> OTHER INFORMATION: KIF5B primer for detecting the fusion gene
      KIF5B-RET derived from AK55 and LC_S6

<400> SEQUENCE: 20
gtgaaacgtt gcaagcagtt ag                                              22

<210> SEQ ID NO 21
<211> LENGTH: 22
<212> TYPE: DNA
<213> ORGANISM: Artificial Sequence
<220> FEATURE:
<223> OTHER INFORMATION: RET primer for detecting the fusion gene
      KIF5B-RET

<400> SEQUENCE: 21
ccttgaccac ttttccaaat tc                                              22

<210> SEQ ID NO 22
<211> LENGTH: 22
<212> TYPE: DNA
<213> ORGANISM: Artificial Sequence
<220> FEATURE:
<223> OTHER INFORMATION: KIF5B primer for detecting the fusion protein
      KIF5B-RET derived from LC_S2

<400> SEQUENCE: 22
taaggaaatg accaaccacc ag                                              22

FUSION PROTEIN COMPRISING C-TERMINAL DOMAIN OF RET PROTEIN AND USE THEREOF AS A DIAGNOSING MARKER

CROSS-REFERENCE TO RELATED APPLICATION

This application claims priority to and the benefit of U.S. Provisional Application No. 61/553,483 filed in the United States Patent and Trademark Office on Oct. 31, 2011, the entire contents of which are incorporated herein by reference.

BACKGROUND OF THE INVENTION (a) Field of the Invention

A fusion protein including N-terminal domain of a fusion partner at N-terminal and C-terminal domain of RET protein at C-terminal, a fusion gene encoding the fusion protein, and a use of the fusion protein or the fusion gene as a diagnosing marker for a cancer, are provided.

(b) Description of the Related Art

Lung cancer remains a leading cause of mortality in cancer, with around 1.38 million deaths worldwide annually. With conventional chemotherapeutic regimen, the median survival time for lung cancer patients in advanced stages is less than one year from diagnosis. Tobacco smoking is known to be the major risk factor of lung cancer in Western countries, where 85% to 90% of all lung cancers were attributed to smoking. However, approximately 25% of lung cancer patients worldwide are 'never-smokers'. Data from many Asian countries have shown that 'never-smokers' constitute 30-40% of non-small-cell lung cancer (NSCLC), which accounts for ~80% of lung cancer cases. In NSCLC, a dominant histological type is adenocarcinoma (~70%).

Lung cancer of never-smokers tends to be driven by single somatic mutation events, rather than global genetic and epigenetic changes. A subset of somatic mutations has been reported in NSCLC in the past few years, such as EGFR, KRAS and ALK genes (which are conventionally called as 'the triple-markers'). Mutations in the tyrosine kinase domain of EGFR, which are associated preferentially with NSCLC of non-smokers and Asians, are sensitive to EGFR targeted therapy, such as Gefitinib. Missense mutations in KRAS are common in the lung adenocarcinomas of smokers, and induce resistance to EGFR inhibitors.

Although several genetic mutations have been reported, a large proportion of lung cancer patients have been observed to have none of them in their cancer genome. More than 40% of NSCLC appear to be driven by unknown genetic events. Therefore, it is needed to find more effective genetic markers for lung cancer.

SUMMARY OF THE INVENTION

An embodiment provides a fusion protein consisting essentially of N-terminal domain of a fusion partner and C-terminal domain of RET protein. The fusion protein may be KIF5B-RET fusion protein consisting essentially of N-terminal domain of KIF5B protein and C-terminal domain of RET protein.

Another embodiment provides a fusion gene encoding the fusion protein.

Another embodiment provides a recombinant vector including the fusion gene.

Another embodiment provided a method of diagnosing a lung cancer including: detecting at least one selected from the group consisting of an RET-involved chromosomal rearrangement including inversion or translocation in Chromosome 10; a fusion protein wherein RET protein is fused with other protein; a fusion gene encoding the fusion protein; and the overexpression of RET compared to a standard sample from an individual without a cancer, wherein when at least one selected from the above group is detected in the test sample, the subject from which the test sample taken is determined as a lung cancer patient.

Another embodiment provides a use of the KIF5B-RET fusion protein as a marker for diagnosing a lung cancer.

Another embodiment provides a composition for diagnosing a lung cancer comprising a material for detecting the fusion protein or the fusion gene.

Another embodiment provides a method of preventing or treating a lung cancer, comprising the step of administering a therapeutically effective amount of at least one inhibitor against the fusion protein, at least one inhibitor against the fusion gene encoding the fusion protein, at least one inhibitor against a RET coding gene, or a combination thereof, to a patient in need thereof.

Another embodiment provides a composition for preventing or treating a lung cancer, comprising at least one inhibitor against the fusion protein, at least one inhibitor against the fusion gene encoding the fusion protein, at least one inhibitor against a RET coding gene, or a combination thereof, as an active ingredient.

Another embodiment provides a use of at least one inhibitor against the fusion protein, at least one inhibitor against the fusion gene encoding the fusion protein, at least one inhibitor against a RET coding gene, or a combination thereof for preventing or treating a lung cancer.

Still another embodiment provides a method of screening an anticancer drug against lung cancer including: treating a cell expressing the fusion protein with a sample compound; measuring the fusion protein expression level in the cell, wherein the fusion protein expression level in the cell treated with the sample compound is decreased compared with that before the treatment with the sample compound or that in a non-treated cell, the sample compound is determined as a candidate compound for the anticancer drug against lung cancer.

DETAILED DESCRIPTION OF THE EMBODIMENTS

The present inventors identified a fusion gene generated by a chromosomal inversion event in lung adenocarcinoma patients, to complete the present invention. It is found that the fusion gene is detected even in a young, never-smoker lung adenocarcinoma patient, whose cancer was negative for the previously known triple-markers (EGFR, KRAS and ALK genes). Therefore, the fusion gene is expected as an effective marker for a lung cancer, which can function as a marker even when the previously known triple-markers cannot function.

An embodiment provides a fusion gene specifically found at a cancer cell and a fusion protein encoded by the fusion gene.

In particular, a fusion protein including N-terminal domain of a fusion partner and C-terminal domain of RET protein is provided. The N-terminal domain of a fusion partner may be positioned at N-terminus of the fusion protein, and the C-terminal domain of RET protein may be positioned at C-terminus of the fusion protein. In the present invention, it is found that the existence of a fusion protein including RET protein is associated with the development of a cancer, such as a lung cancer.

The fusion partner may be a N-terminal domain of KIF5B protein, which is positioned at N-terminus of the fusion protein. In this case, the fusion protein may be represented as KIF5B-RET protein which includes N-terminal domain of KIF5B protein at N-terminus and C-terminal domain of RET protein at C-terminus.

Another embodiment provides a fusion gene encoding the fusion protein, where a gene encoding the N-terminal domain of the fusion partner positions at 5' end and a gene encoding the C-terminal domain of the RET protein positions at 3' end. In a concrete embodiment, when the fusion protein is the KIF5B-RET protein, the fusion gene may be represented as KIF5B-RET gene, where a gene encoding the N-terminal domain of KIF5B positions at 5' end and a gene encoding the C-terminal domain of the RET protein positions at 3' end.

Another embodiment provides an expression vector including the fusion gene and optionally transcription elements (e.g., a promoter and the like) operably linked to the fusion gene. Another embodiment provides a transformant cell transformed with the expression vector.

The RET protein is a transmembrane receptor tyrosine kinase. The RET consists of extracellular region (which contains Cadherin-like domains), a trans-membrane domain and an intracellular region containing a tyrosine kinase domain. When the RET protein is dimerized by binding co-receptors and ligands, such as glial derived neurotrophic factor (GDNF), it is activated by auto-phosphorylation and then simulates downstream signaling pathways. The downstream signaling cascade of the RET is the mitogen-activated protein kinase (MAPK) pathway, which regulates cell survival/apoptosis, proliferation, differentiation, and migration. The normal expression of RET is important for neuronal development, but it is known not to be activated in differentiated tissues.

The RET protein may be derived from a mammal, such as a human. The human RET gene encoding the human RET protein is localized to chromosome 10 (10q11.2) and contains 19-21 exons depending on variants. The human RET protein may be encoded by a human RET gene represented by the NCBI accession number NM_020630 or NM_020975.

The C-terminal domain of RET protein may include an amino acid sequence encoded by a polynucleotide from $12^{th}$ exon to the last exon (for example, $20^{th}$ exon) of RET gene (e.g., NM_020630 or NM_020975). The C-terminal domain of RET protein may include consecutive at least about 300 amino acids from the start position of $12^{th}$ exon (for example $713^{th}$ position for the RET protein encoded by NM_020975) toward C-terminus of the RET protein encoded by NM_020630 or NM_020975. For example, the C-terminal domain of RET protein may include consecutive about 300 to about 450 amino acids, consecutive about 300 to about 420 amino acids, or consecutive about 300 to about 402 amino acids from the start position of $12^{th}$ exon (e.g., $713^{th}$ position) toward C-terminus of the RET protein encoded by NM_020630 (19 exons) or NM_020975 (20 exons).

The KIF5B protein, which is also called as Kinesin-1 heavy chain, is a protein encoded by KIF5B gene. The KIF5B protein may be derived from a mammal, such as a human. The human KIF5B gene encoding the human KIF5B protein is localized to chromosome 10 (10q11.22) and contains 26 exons. The human KIF5B protein may be encoded by a human KIF5B gene represented by the NCBI accession number NM_004521.

The N-terminal domain of KIF5B protein may include an amino acid sequence encoded by a polynucleotide from the first exon to $16^{th}$ exon, or from the first exon to $15^{th}$ exon, or from the first exon to $23^{th}$ exon of KIF5B gene (e.g., NM_004521). The N-terminal domain of KIF5B protein may include consecutive at least about 329 amino acids from $1^{st}$ position (that is, at least amino acid sequence from $1^{st}$ to $329^{th}$ positions) of the KIF5B protein encoded by NM_004521. The N-terminal domain of KIF5B protein may further include at least two coiled coil domain which starts from the amino acid of the $329^{th}$ position of the KIF5B protein encoded by NM_004521. For example, the two coiled coil domain further included may have an amino acid sequence of $329^{th}$ to $638^{th}$ positions of the KIF5B protein encoded by NM_004521 (SEQ ID NO: 21). The N-terminal domain of KIF5B protein may include consecutive about 329 to 900 amino acids, consecutive about 329 to 700 amino acids, consecutive about 329 to 650 amino acids, or consecutive about 329 to 638 amino acids from $1^{st}$ position of the KIF5B protein encoded by NM_004521.

In the fusion protein, the fusion may occur between the $16^{th}$ exon of KIF5B gene and $12^{th}$ exon of RET gene, which is called as a fusion point or breakpoint. The term "a fusion region" may refer to a polynucleotide fragment (about ~30 nucleotides) or polypeptide (about ~30 amino acids) fragment around the fusion point.

As used herein, the exon number is numbered according to the exon number allocated by NCBI.

In an Embodiment, the fusion protein KIF5B-RET may have the amino acid sequence of SEQ ID NO: 3, 7, 11 or 15, wherein a polypeptide fragment from $629^{th}$ to $648^{th}$ positions of SEQ ID NO: 3, from $629^{th}$ to $648^{th}$ positions of SEQ ID NO: 7, from $566^{th}$ to $585^{th}$ positions of SEQ ID NO: 11, and from $839^{th}$ to $858^{th}$ positions of SEQ ID NO: 15 may be a fusion region of the fusion protein KIF5B-RET. The fusion region of the fusion protein KIF5B-RET may have the amino acid sequence of SEQ ID NO: 4, 8, 12 or 16. The fusion gene of KIF5B-RET encoding the fusion protein of KIF5B-RET may have the nucleotide sequence of SEQ ID NO: 1, 5, 9 or 13, wherein a polynucleotide from $1885^{th}$ to $1944^{th}$ positions of SEQ ID NO: 1, $1885^{th}$ to $1944^{th}$ positions of SEQ ID NO: 5, $1696^{th}$ to $1755^{th}$ positions of SEQ ID NO: 9, and $2515^{th}$ to $2574^{th}$ positions of SEQ ID NO: 13 may be a fusion region of the fusion gene KIF5B-RET. The fusion region of the fusion gene KIF5B-RET may have the nucleotide sequence of SEQ ID NO: 2, 6, 10 or 14. The fusion genes, the fusion proteins, and the fusion regions thereof are shown in FIGS. 27 to 34.

The nucleotide sequences of DNA molecules and the amino acid sequences of proteins encoded by the DNA molecules may be determined by an automated DNA sequencer or an automated peptide sequencer. The (nucleotide or amino acid) sequences determined by such automated sequencing means may include partial error compared with actual sequences. For Generally, the sequences determined by automated sequencing may have sequence identity of at least about 90%, at least about 95%, at least about 99%, or at least about 99.9% compared with actual sequences. Therefore, the fusion protein, the fusion gene or the fusion region may have an amino acid sequence or a nucleotide sequence having sequence identity of at least about 90%, at least about 95%, at least about 99%, or at least about 99.9% compared with the sequences of SEQ ID NOS: 1 to 17.

It is confirmed that the fusion protein and the fusion gene are specifically present in cancer region, and they are not present in other region around the cancer region in the same tissue, suggesting a use of the fusion protein and/or the fusion gene as a biomarker for a cancer, for example, a solid cancer, in particular a lung cancer. In addition, a RET-involved chromosomal rearrangement including inversion or translocation in Chromosome 10 or an overexpression of RET is also found in a cancer cell, in particular a lung cancer cell.

Therefore, another embodiment provides a method of diagnosing a cancer or a method of providing information for diagnosing a cancer, including detecting, in a test sample obtained from a subject, at least one selected from the group consisting of:

a RET-involved chromosomal rearrangement including inversion or translocation in Chromosome 10;

a fusion protein including N-terminal domain of a fusion partner and C-terminal domain of RET protein;

a fusion gene encoding the fusion protein; and an overexpression of RET compared to a standard sample from an individual without lung cancer, wherein when at least one selected from the above group is detected in the test sample, the subject is determined as a patient suffered from a cancer.

The RET-involved chromosomal rearrangement may result in formation of the fusion protein or the fusion gene. For example, the RET-involved chromosomal rearrangement may be an inversion Chromosome 10. The inversion of Chromosome 10 may be detected by using a polynucleotide (a probe) capable of hybridizing with (complementarily binding to) the inversion region in Chromosome 10 and/or a primer pair capable of detecting the inversion of Chromosome 10, for example, capable of producing a polynucleotide fragment having consecutive 100 to 200 nucleotides including the inversion region in Chromosome 10. For example, the inversion of Chromosome 10 may be detected by using the primer pair may comprise 5'-CAGAATTTCA-CAAGGAGGGAAG-3' (SEQ ID NO: 18) and 5'-CAG-GACCTCTGACTACAGTGGA-3' (SEQ ID NO: 19).

The fusion protein and the fusion gene are as described above.

In a concrete embodiment, the fusion protein may also be detected by detecting the presence of the fusion protein or the fusion gene or mRNA corresponding to the fusion gene.

The presence of the fusion protein may be detected be a general assay that measures the interaction between the fusion protein and a material (e.g., an antibody or an aptamer) specifically binding to the fusion protein. The general assay may be immunochromatography, immunohistochemical staining, enzyme liked immunosorbent assay (ELISA), radioimmunoassay (RIA), enzyme immunoassay (EIA), florescence immunoassay (FIA), luminescence immunoassay (LIA), western blotting, FACS, and the like.

In addition, the presence of the fusion gene or the mRNA may be detected by a general assay such as PCR, FISH (fluorescent in situ hybridization), and the like, using a polynucleotide capable of hybridizing with (complementarily binding to) the fusion gene or the mRNA. The fusion gene may be detected and/or validated by using the integration techniques of whole-transcriptome (RNA) and/or whole-genome (DNA) sequencing through massively parallel sequencing technologies. The polynucleotide capable of hybridizing with the fusion gene or the mRNA may be a siRNA, an oligonucleotide, DNA probe, or DNA primer, which can detect the fusion gene or the mRNA by a direct hybridization with the fused or truncated gene or transcript in the test sample.

When the fusion gene is a fusion gene KIF5B-RET encoding the fusion protein of KIF5B-RET, the fusion gene KIF5B-RET may be detected by using a polynucleotide (a probe) capable of hybridizing with (complementarily binding to) the fusion region of SEQ ID NO: 2, 6, 10 or 14, and/or a primer pair capable of producing a polynucleotide fragment having consecutive 100 to 200 nucleotides including the fusion region of SEQ ID NO: 2, 6, 10 or 14 in SEQ ID NO: 1, 5, 9 or 13, respectively. For example, the fusion gene KIF5B-RET may be detected by using the primer pair of 5'-GTGAAACGTTGCAAGCAGTTAG-3' (KIF5B; SEQ ID NO: 20) and 5'-CCTTGACCACTTTTCCAAATTC-3' (RET; SEQ ID NO: 21) or 5'-TAAGGAAATGACCAAC-CACCAG-3' (KIF5B; SEQ ID NO: 22) and 5'-CCTTGAC-CACTTTTCCAAATTC-3' (RET; SEQ ID NO: 21). In addition, the fusion protein KIF5B-RET may be detected using an antibody or aptamer specifically binding to the fusion region of the fusion protein KIF5B-RET. For example, the fusion region of the fusion protein KIF5B-RET may have the amino acid sequence of SEQ ID NO: 4, 8, 12 or 16.

The term "capable of hybridizing with the fusion region (or the inversion region)" may refer to having a complementary sequence or a sequence having sequence identity of at least 90% with that of the fusion region (or the inversion region).

Another embodiment provides a composition for diagnosing a cancer, including one or more selected from the group consisting of a polynucleotide capable of hybridizing with the fusion region of SEQ ID NO: 2, 6, 10 or 14, a primer pair capable of producing a polynucleotide fragment having consecutive 100 to 200 nucleotides including the fusion region of SEQ ID NO: 2, 6, 10 or 14 in SEQ ID NO: 1, 5, 9 or 13, respectively, a polynucleotide capable of hybridizing with the inversion region in Chromosome 10, a primer pair capable of producing a polynucleotide fragment having consecutive 100 to 200 nucleotides including the inversion region of Chromosome 10, and an antibody or aptamer binding to the fusion region of SEQ ID NO: 4, 8, 12 or 16. For example, the primer pair may be at least one selected from the group consisting of the primer pair of 5'-GTGAAACGTTGCAAGCAGTTAG-3' (KIF5B; SEQ ID NO: 20) and 5'-CCTTGACCACTTTTCCAAATTC-3' (RET; SEQ ID NO: 21) or 5'-TAAGGAAATGACCAAC-CACCAG-3' (KIF5B; SEQ ID NO: 22) and 5'-CCTTGAC-CACTTTTCCAAATTC-3' (RET; SEQ ID NO: 21), to detect the fusion gene of KIF5B-RET encoding the fusion protein, and the primer pair of 5'-CAGAATTTCA-CAAGGAGGGAAG-3' (SEQ ID NO: 18) and 5'-CAG-GACCTCTGACTACAGTGGA-3' (SEQ ID NO: 19), to detect the inversion of Chromosome 10.

Another embodiment provides a use of the fusion protein and/or the fusion gene for diagnosing a cancer.

The patient may be any mammal, for example, a primate such as a human or monkey, a rodent such as a mouse or a rat, in particular a human.

The test sample may be a cell (e.g., a lung cell), a tissue (e.g., a lung tissue), or body fluid (e.g., blood) separated from the patient, for example a human. The patient may be being treated or planed to be treated with a kinase inhibitor. The test sample may include a cell derived from a human cancer cell or an extract thereof.

The fusion protein and/or the fusion gene may act as a target for treatment of a cancer.

Therefore, another embodiment provides a method of preventing and/or treating a cancer, comprising administering a pharmaceutically (therapeutically) effective amount of at least one inhibitor against the fusion protein, at least one inhibitor against the fusion gene encoding the fusion protein, at least one inhibitor against a RET coding gene, or a combination thereof, to a patient in need thereof. The method may further comprise the step of identifying the patient who needs the prevention and/or treatment of a cancer, prior to the step of administering.

Another embodiment provides a composition for preventing and/or treating a cancer, comprising at least one inhibitor against the fusion protein, at least one inhibitor against the fusion gene encoding the fusion protein, at least one inhibitor against a RET coding gene, or a combination thereof.

Another embodiment provides a use of an inhibitor against the fusion protein, an inhibitor against the fusion gene encoding the fusion protein, an inhibitor against a RET coding gene, or a combination thereof, for preventing and/or treating a cancer.

The inhibitor against the fusion protein of KIF5B-RET may be at least one selected from the group consisting of an aptamer specifically binding to the fusion protein; an antibody specifically binding to the fusion protein; and a kinase inhibitor such as sorafenib(4-[4-[[4-chloro-3-(trifluoromethyl)phenyl]carbamoylamino]phenoxy]-N-methyl-pyridine-2-carboxamide), cabozantinib(N-(4-((6,7-Dimethoxyquinolin-4-yl)oxy)phenyl)-N-(4-fluorophenyl) cyclopropane-1,1-dicarboxamide), and the like. The inhibitor against the fusion gene or the RET coding gene may be at least one selected from the group consisting of sRNA, shRNA, miRNA, and an aptamer, which are capable of specifically binding to the fusion gene or the RET coding gene.

In the present invention, the cancer may be any solid cancer, for example, a lung cancer, a liver cancer, a colon cancer, a pancreatic cancer, a gastric cancer, a breast cancer, an ovarian cancer, a renal cancer, a thyroid cancer, an esophageal cancer, a prostatic cancer, or a brain cancer. In concrete embodiment, the cancer may be a lung cancer, in particular a small cell lung cancer (SCLC) or a non-small cell lung cancer (NSCLC) such as a lung adenocarcinoma, a squamous cell lung carcinoma, or a large cell lung carcinoma.

Still another embodiment provides a method of screening an anticancer drug including:

contacting a sample compound to a cell expressing the fusion protein; and
measuring the fusion protein expression level in the cell,
wherein the fusion protein expression level in the cell treated with the sample compound is decreased compared with that before the treatment with the sample compound or that in a non-treated cell, the sample compound is determined as a candidate compound for the anticancer drug.

The method of screening an anticancer drug may further include the step of measuring the fusion protein expression level in the cell before the treatment of the sample compound. In this case the sample compound may be determined as a candidate compound for the anticancer drug when the fusion protein expression level after treatment of the sample compound is decreased compared with that before the treatment with the sample compound in the same cell. Alternatively, the method of screening an anticancer drug may include providing cells expressing the fusion protein, and contacting a sample compound to a part of the provided cells. In this case the sample compound may be determined as a candidate compound for the anticancer drug when the fusion protein expression level in the cell contacted with the sample compound is decreased compared with that in the cells which are not contacted with the sample compound.

The cell used in the screening method may be a cell derived from a cancer cell where the fusion gene or the fusion protein is expressed and/or activated, an extract of the cell, or a culture of the cell. The cancer cell may be a solid cancer cell, in particular a lung cancer, for example a non-small cell lung cancer such as a lung adenocarcinoma, as described above.

The fusion protein expression level may be detected be a general assay such as immunochromatography, immunohistochemical staining, enzyme liked immunosorbent assay (ELISA), radioimmunoassay (RIA), enzyme immunoassay (EIA), florescence immunoassay (FIA), luminescence immunoassay (LIA), western blotting, FACS, and the like.

The sample compound may be any natural or synthetic compound, for example at least one selected from the group consisting of a general compound, DNA, RNA, protein, and the like.

BRIEF DESCRIPTION OF THE DRAWINGS

FIG. 27 shows nucleotide sequence of KIF5B-RETa fusion gene and its fusion region, wherein the KIF5B domain is derived from NM_020975.

FIG. 28 shows amino acid sequence of KIF5B-RETa fusion protein and its fusion region, wherein the KIF5B domain is derived from NM_020975.

FIG. 29 shows nucleotide sequence of KIF5B-RETc fusion gene and its fusion region, wherein the KIF5B domain is derived from NM_020630.

FIG. 30 shows amino acid sequence of KIF5B-RETc fusion protein and its fusion region, wherein the KIF5B domain is derived from NM_020630.

FIG. 31 shows nucleotide sequence of KIF5B-RETa variant fusion gene and its fusion region, obtained from LC_S2.

FIG. 32 shows amino acid sequence of KIF5B-RETa variant fusion protein and its fusion region, obtained from LC_S2.

FIG. 33 shows nucleotide sequence of KIF5B-RETa variant fusion gene and its fusion region, obtained from LC_S6.

FIG. 34 shows amino acid sequence of KIF5B-RETa variant fusion protein and its fusion region, obtained from LC_S6.

EXAMPLE

The present invention is further explained in more detail with reference to the following examples. These examples, however, should not be interpreted as limiting the scope of the present invention in any manner.

Example 1: Sample Preparations

All protocols used in this example were approved by the Institutional Review Board of Seoul St. Mary's Hospital (Approval #KC11OISI0603). Paraffin-embedded tissues were obtained from primary lung cancer and bone metastasis of a patient AK55. A frozen tissue from biopsy of liver metastatic cancer from AK55 was also available to use. In addition, venous blood of AK55 was extracted. Genomic DNA was extracted from the lung cancer, bone metastasis, liver metastasis and blood of the patient AK55. Furthermore, RNA was extracted from the frozen liver metastasis of the patient AK55. Then cDNA was synthesized from total RNA as described in "Ju Y S, Kim J I, Kim S, et al., Nat Genet 2011," which is incorporated herein by reference.

Figure 1:
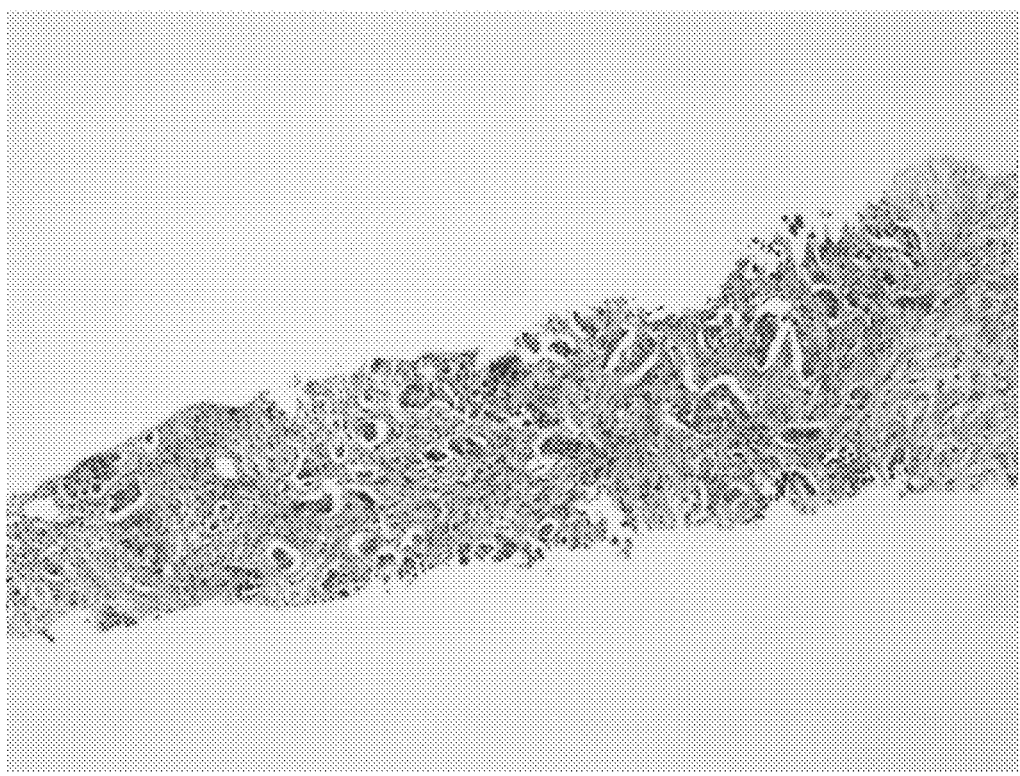
FIG. 1 is a microscopic image showing a paraffin section from a primary lung cancer tissue of a patient (AK55) obtained by CT-guided biopsy stained by hematoxylin and eosin, in magnification ratio of ×100.
Figure 2:
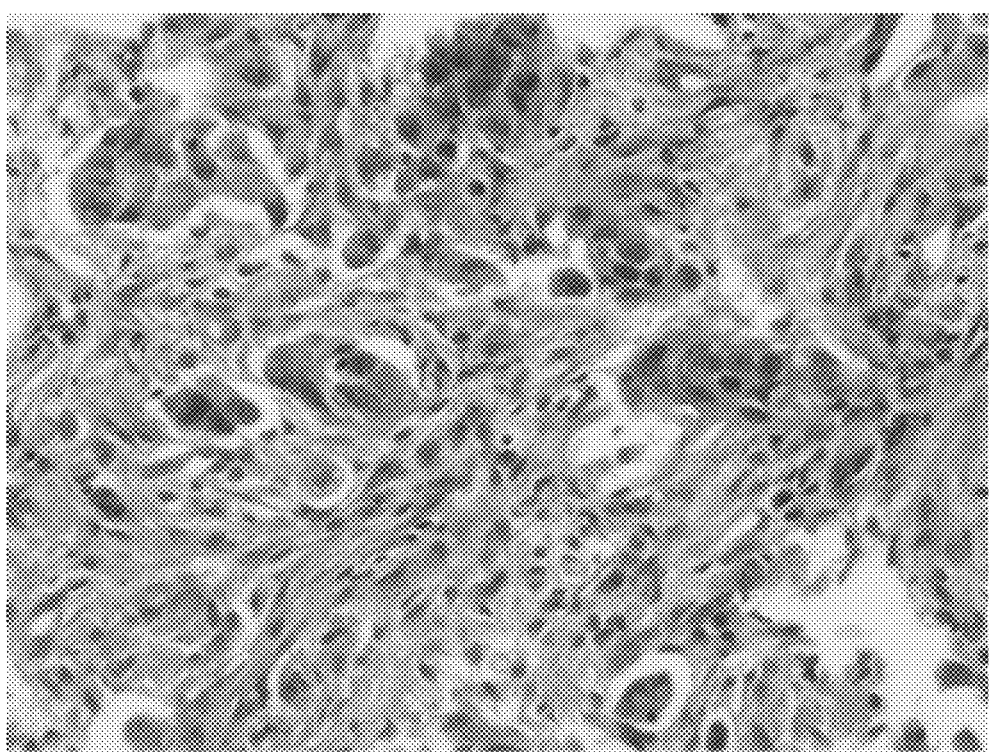
FIG. 2 is a microscopic image showing a paraffin section from a primary lung cancer tissue of a patient (AK55) obtained by CT-guided biopsy stained by hematoxylin and eosin, in magnification ratio of ×400.

The patient AK55 (A 33-year-old man patient received a diagnosis of lung adenocarcinoma with multiple metastases) was healthy until 33 years of age, when a poorly differentiated adenocarcinoma developed in the right upper lobe of lung as shown in FIGS. 1 and 2. FIGS. 1 and 2 are microscopic images showing a paraffin section from a primary lung cancer tissue obtained by CT-guided biopsy (stained by hematoxylin and eosin) (FIG. 1: ×100; FIG. 2: ×400). In the cancer tissue, poorly differentiated tumor cell nests were present in the desmoplastic stroma. In addition, the cancer cells had plump cytoplasm and large pleomorphic nuclei.

The metastases in liver and multiple bones were also detected in positron emission tomography (PET) studies. For pathological diagnosis, he underwent CT-guided biopsy of primary lung cancer as well as ultrasound-guided biopsy of liver metastasis. The patient AK55 has no known family history of cancers from grandparents and he is a never-smoker. A week after diagnosis, he suffered from a neck fracture due to the metastasis in cervical bone, and underwent a C7 corpectomy. In pathologic studies, his lung adenocarcinoma was negative for known EGFR, KRAS and ALK mutations. The immunohistochemical analysis results for CK7, CK20 and TTF1 were consistent with lung adenocarcinoma (FIGS. 3-5; positive for CK7 (FIG. 3) and TTF1 (FIG. 4), negative for CK20 (FIG. 5)).

Figure 3:
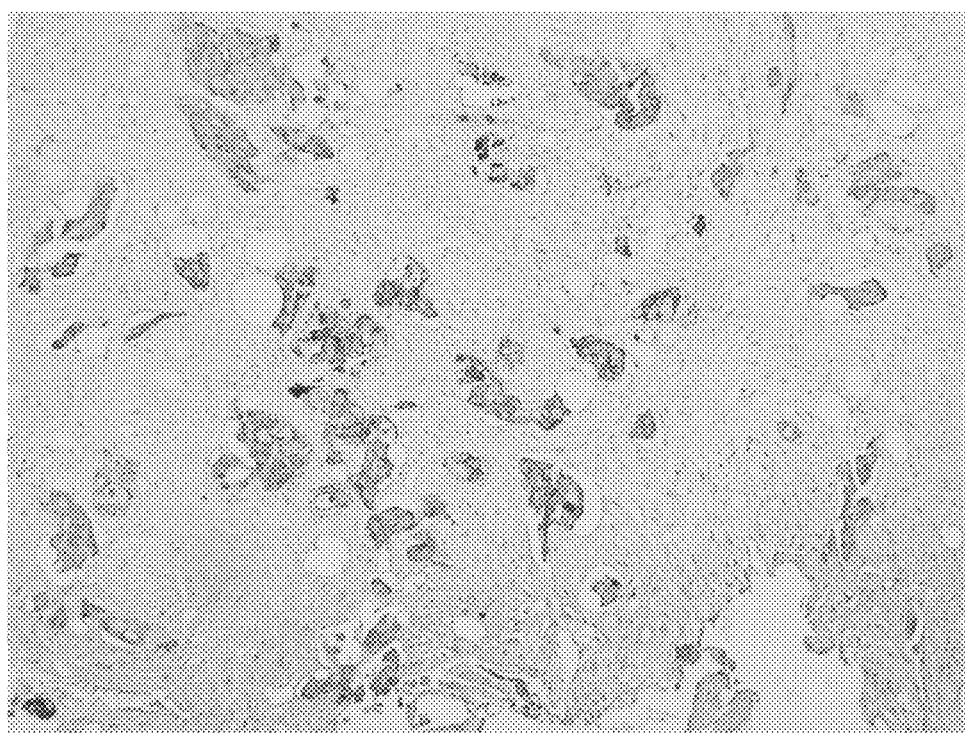
FIG. 3 is a microscopic image showing a result of immunohistochemical analysis of a primary lung cancer tissue for CK7.
Figure 4:
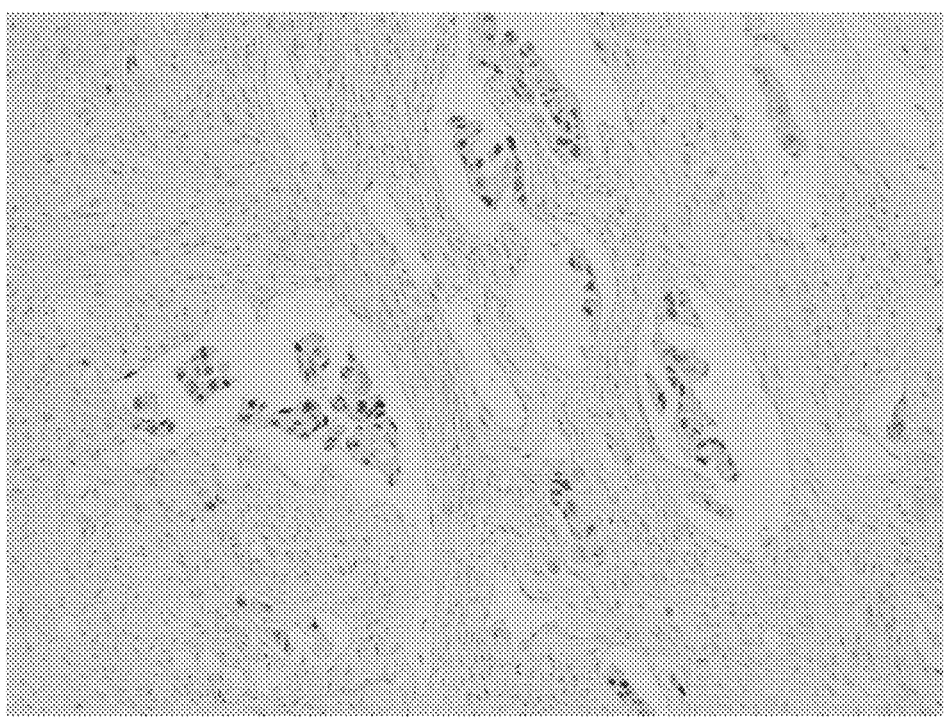
FIG. 4 is a microscopic image showing a result of immunohistochemical analysis of a primary lung cancer tissue for TTF1.
Figure 5:
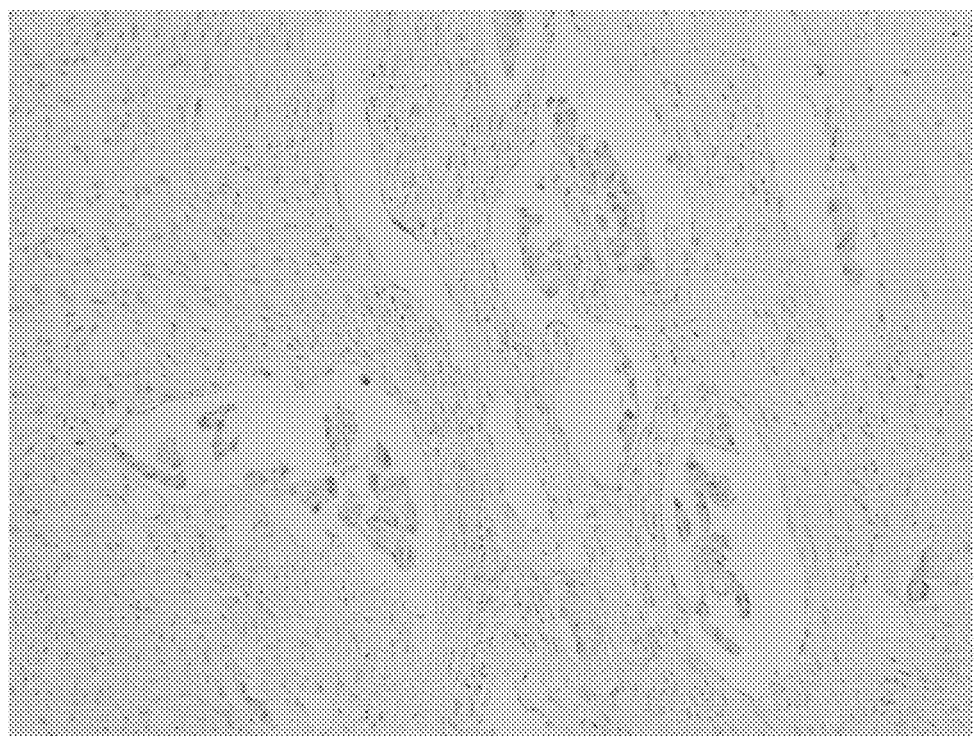
FIG. 5 is a microscopic image showing a result of immunohistochemical analysis of a primary lung cancer tissue for CK20.

FIGS. 3-5 are microscopic images showing results of immunohistochemical analyses of a primary lung cancer tissue (FIG. 3; CK7; FIG. 4: TTF1; FIG. 5: CK20). These analyses were done in the metastatic tumor in the cervical bone. CK7 and TTF1 were positive, but CK20 was negative. The results highly suggest that primary lung adenocarcinoma is the origin of this cancer.

Example 2: Whole-Genome Analysis

Genomic variants of each sample obtained from the patient AK55 as described in Example 1 was classified into single nucleotide variation (SNV), short insertion and deletion (indel) and large deletions, using modified criteria of whole-genome sequencing as described in "Ju Y S, Kim J I, Kim S, et al., Nat Genet 2011" and "Kim J I, Ju Y S, Park H, et al., Nature 2009; 460:1011-5", which are incorporated herein by reference. Then, the genomic variants in cancer tissue were compared with those in blood to identify cancer-associated somatic mutations. DNA and RNA sequencing data was also analyzed as described in "Ju Y S, Kim J I, Kim S, et al., Nat Genet 2011," which is incorporated herein by reference.

Because the DNA of primary lung cancer was extracted from a small amount of DNA in the paraffin-embedded tissue, the short-read redundancy was too high for analysis. Hence, the primary comparisons were done between the sequences from liver metastasis and blood. The sequencing experiments were performed using the standard methods of Illumina and described in "Ju Y S, Kim J I, Kim S, et al., Nat Genet 2011" and "Kim J I, Ju Y S, Park H, et al., Nature 2009; 460:1011-5", which are incorporated herein by reference.

Sequencing libraries were generated according to the standard protocol of Illumina Inc. for high-throughput sequencing. Excluding the genomic DNA from paraffin-embedded bone metastasis (of which DNA concentration was too low and it did not qualify under the inventor's criteria for generating the sequencing library), samples were sequenced using Illumina HiSeq2000 and Genome Analyzer IIx. From whole-genome deep sequencing of cancer (liver metastasis) and normal tissue (blood) of the patient AK55, the inventors obtained 47.77× and 28.27× average read-depth, respectively. The obtained results are shown in Table 1.

TABLE 1

Summary statistics of sequencing analysis of the lung cancer patient AK55.

| | | | Massively Parallel Sequencing | | | | Validation |
|---|---|---|---|---|---|---|---|
| Analysis | Tissue | Source | Number of aligned reads | Read length (bp) | Throughput (Gbp) | Read depth (fold) | PCR and Sanger sequencing |
| Genome | Blood | Fresh | 392,194,564 | 103 | 80.79 | 28.27 | Yes |
| | Lung cancer | Paraffin-embedded | 274,909,815 | 103 | 56.63 | 19.81 | Yes |
| | Liver metastasis | Frozen | 362,530,401 | 101 | 136.55 | 47.77 | Yes |
| | | | 293,140,533 | 108 | | | |
| | Bone metastasis | Paraffin-embedded | — | — | — | — | Yes |
| Transcriptome | Liver metastasis | Frozen | 89,682,934 | 101.68 | 15.16 | — | Yes |

Figure 6:
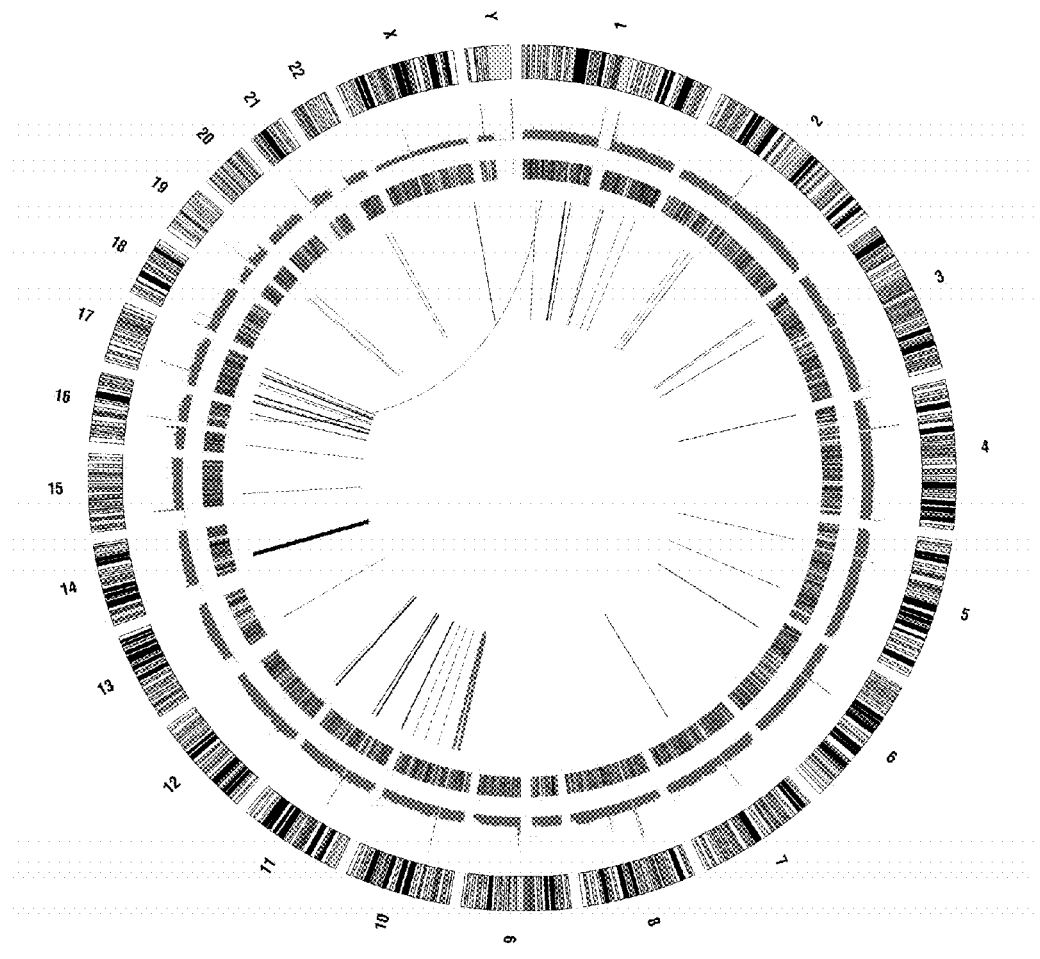
FIG. 6 shows a graphical representation of fusion genes identified in the lung cancer transcriptome sequencing.

The whole-genome coverage was evenly distributed (excepting normal 'spikes' in the centromeric or telomeric regions) suggesting no evidence of aneuploidy in the cancer tissue (FIG. 6). FIG. 6 shows a graphical representation of fusion genes identified in the lung cancer transcriptome sequencing. Intra- and inter-chromosomal fusion genes are shown in the central layer. The thickness of lines shows the amount of evidence (number of spanning reads). The KIF5B-RET fusion gene is shown in red. Chromosome ideograms are shown in the outer layer. Coverage of cancer whole-genome sequencing is shown in the $1^{st}$ middle layer. This suggests that the cancer genome has no large chromosomal aneuploidy. Expression level of genes is shown in the $2^{nd}$ middle layer using heatmap.

In the cancer whole-genome sequence, we could not find any known cancer-related somatic point mutations, archived in OMIM (Online Mendelian Inheritance in Man) and SNPedia. The comparison of SNVs, indels and copy number variants (CNVs) between cancer and blood did not show any remarkable mutations in the cancer-related genes which could drive oncogenesis.

Example 3: Fusion Gene Analysis

For detection of fusion genes using transcriptome sequencing, discordant reads, where the ends of a read were aligned to different genes, and exon-spanning reads across the fusion breakpoint of chimeric transcripts, were used. For final fusion gene candidates, corresponding genomic rearrangements, such as inversions, translocations and large deletions were assessed in the whole-genome sequencing data.

Transcriptome data were analyzed. The inventors have focused on detecting fusion genes since many cancers are known to be driven by fusion genes resulting from pathogenic chromosomal translocation or inversion.

To detect fusion genes, each end of about 300 bp-long cDNA fragment was sequenced up to 101 bp by next generation sequencing (Ju Y S et al., Genome Res. 2012 22:436-445). From the sequence data, we examined the existence of a discordant read wherein the sequences of both ends are aligned on different chromosomes. In addition, exon-spanning reads, one of each end sequence is generated from a breakpoint of the fusion gene, was also examined. Discordant and exon-spanning reads indicate the existence of a fusion gene. Genes that have both discordant reads and exon-spanning reads were determined as lung cancer fusion genes.

The approaches identified 52 fusion genes (Table 2; FIG. 6).

TABLE 2

Selected fusion genes (20 out of 52 in total) identified in AK55.

| Category | Donor gene | Acceptor gene | Chr | Distance (Mb) | # of discordant reads | # of spanning reads | Evidence in whole-genome sequence |
|---|---|---|---|---|---|---|---|
| Intra-chromosomal | KIF5B | RET | 10 | 10.580 | 34 | 60 | YES (inversion) |
| | KIF5B | KIAA1462 | 10 | 1.970 | 4 | 4 | — |
| | EEF1DP3 | FRY | 13 | 0.133 | 3 | 5 | — |
| | RPS6KB1 | TMEM49 | 17 | 0.097 | 4 | 31 | — |
| | HACL1 | COLQ | 3 | 0.075 | 3 | 4 | — |
| | TMEM56 | RWDD3 | 1 | 0.073 | 4 | 11 | — |
| | FAM18B2 | CDRT4 | 17 | 0.065 | 4 | 29 | — |
| | CTBS | GNG5 | 1 | 0.065 | 6 | 27 | — |
| | METTL10 | FAM53B | 10 | 0.054 | 2 | 4 | — |
| | AZGP1 | GJC3 | 7 | 0.048 | 5 | 15 | — |
| | NKX2-1 | SFTA3 | 14 | 0.046 | 3 | 7 | — |
| | ADSL | SGSM3 | 22 | 0.036 | 5 | 6 | — |
| | ART4 | C12orf69 | 12 | 0.034 | 3 | 4 | — |
| | LOC100131434 | IDS | X | 0.031 | 2 | 11 | — |
| | LOC100130093 | SNAP47 | 1 | 0.030 | 2 | 2 | — |
| | C15orf57 | MRPL42P5 | 15 | 0.025 | 2 | 7 | — |

TABLE 2-continued

Selected fusion genes (20 out of 52 in total) identified in AK55.

| Category | Donor gene | Acceptor gene | Chr | Distance (Mb) | # of discordant reads | # of spanning reads | Evidence in whole-genome sequence |
|---|---|---|---|---|---|---|---|
| | MIA2 | CTAGE5 | 14 | 0.024 | 30 | 102 | — |
| | SH3D20 | ARHGAP27 | 17 | 0.024 | 2 | 10 | — |
| | RBM14 | RBM4 | 11 | 0.023 | 16 | 24 | — |
| Inter-chromosomal | RSPO1 | HP | 16; 1 | — | 2 | 3 | — |

Of these, 94.2% (n=49) were intrachromosomal fusions between adjacent genes (<135 Kb), which may not have any functional roles in oncogenesis (Table 2). In addition, one (1.9%) were inter-chromosomal fusions, but these were generated by haptoglobin (HP), which is highly expressed genes in liver. Although the existence of this fusion gene is interesting biologically, given the molecular function of the gene, it is not believed to be tumorigenic. The remaining two (3.8%) were KIF5B-RET and KIAA1462-KIF5B fusion genes, which were intrachromosomal fusions between remote genes (>~2 Mb). Of these, KIAA1462-KIF5B was excluded, since its expression level is low and KIAA1462 is a hypothetical protein of which the molecular function is not known. Except KIF5B-RET fusion, we could not detect the corresponding chromosomal rearrangements (e.g. large deletion, inversion or translocation) in the fusion gene candidates.

Figure 7:
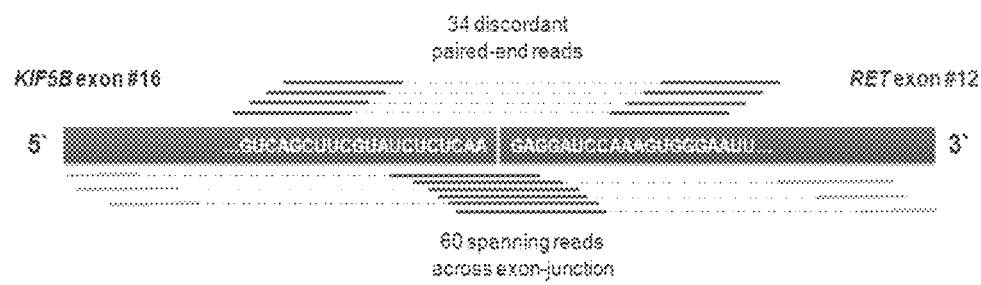
FIG. 7 schematically shows KIF5B-RET fusion gene.

The final fusion gene, KIF5B-RET, was interesting in particular, since RET is a well known tyrosine-kinase proto-oncogene. In addition, this fusion gene has not been reported in human cancer, hence it is considered to be novel. The characteristics of this gene fusion event were further confirmed using RNA sequencing data. The fusion gene was highly expressed, as evidenced by 34 discordant paired-end reads and 60 spanning reads across the fusion-junction (see Table 2 and FIG. 7). FIG. 7 schematically shows KIF5B-RET fusion gene. In the transcriptome sequencing, 34 discordant paired-end reads and 60 spanning reads across the exon-junction were identified. The existence of these reads is strong evidence of a fusion gene. A discordant paired-end read is defined as a read whose end-sequences are aligned to different genes. A spanning read is a read, one of whose end-sequences is aligned across the junction of the predicted fusion transcripts. In this analysis, the fusion occurred between the $16^{th}$ exon of KIF5B and $12^{th}$ exon of RET.

Figure 8:
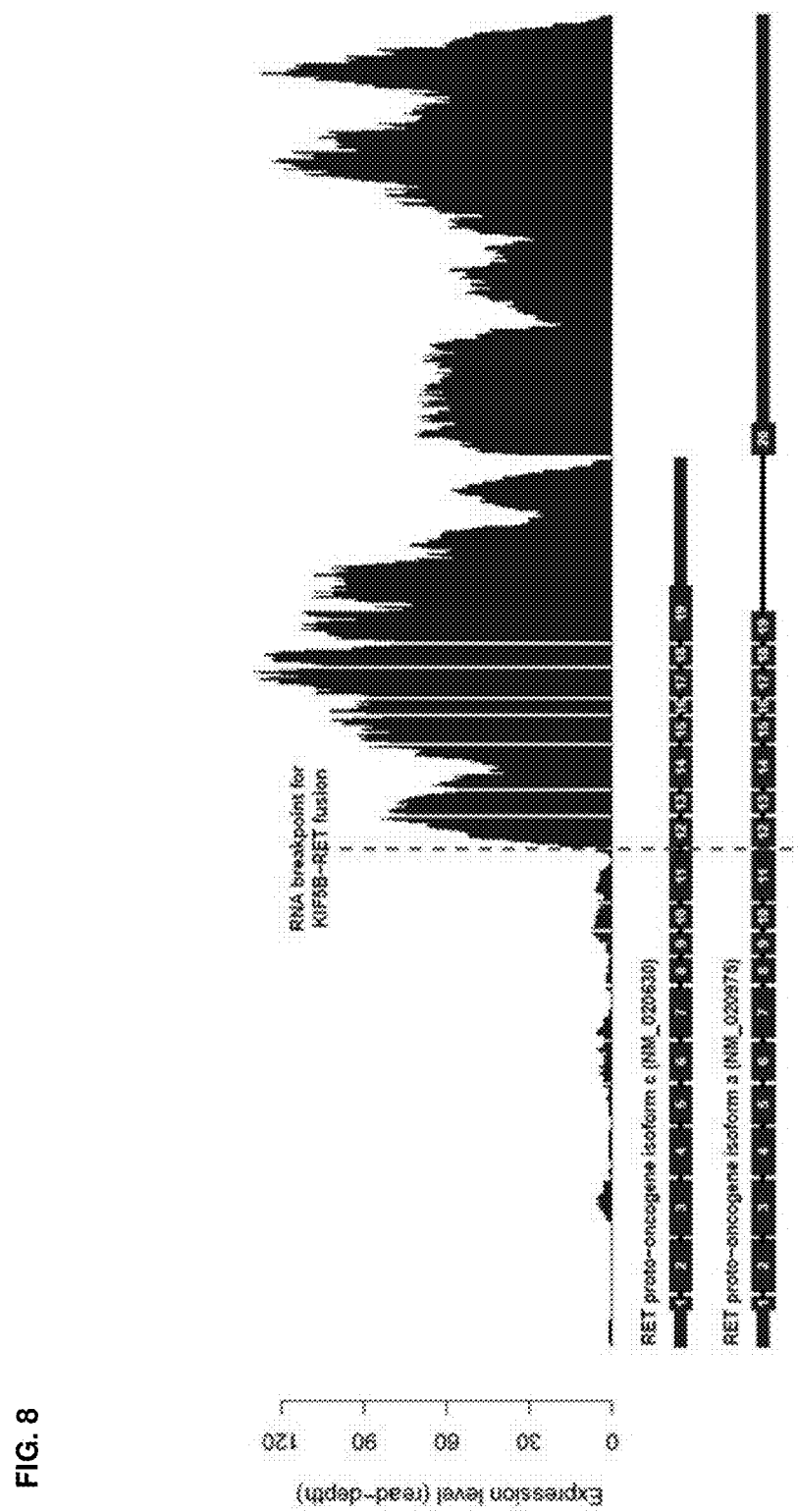
FIG. 8 is a graph showing RNA expression level of each RET exon.

These data showed that the end of the $16^{th}$ exon of KIF5B and the start of the $12^{th}$ exon of the RET proto-oncogene were integrated. The expression profile showed that the first to eleventh exons of RET were not expressed (FIG. 8) in the cancer tissue, suggesting most of the RET expression in the cancer took place from the fusion gene rather than from the intact RET gene. FIG. 8 is a graph showing RNA expression level of each RET exon. RET expression was observed from the $12^{th}$ exon, downstream of the junction of the fusion gene. This suggests that all the RET expression originated from the KIF5B-RET fusion gene, rather than normal RET.

Figure 9:
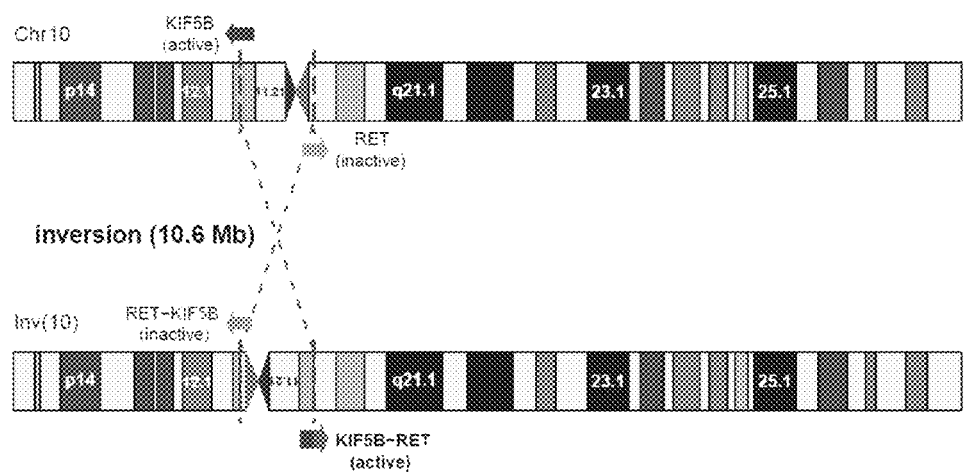
FIG. 9 schematically shows a 10.6 Mb-long inversion event in chromosome 10 in the massively parallel sequencing of the cancer genome.

KIF5B and RET are 10.6 Mb away from each other, located at 10p11.22 and 10q11.21, respectively. Because the coding strands for the two genes are different, a 10.6 Mb-long inversion event is necessary for the fusion gene (see FIG. 9). FIG. 9 schematically shows a 10.6 Mb-long inversion event in chromosome 10 in the massively parallel sequencing of the cancer genome. This event is the cause of the KIF5B-RET fusion gene. KIF5B is generally expressed with its universal promoter. After the inversion event, this promoter activates global expression of the KIF5B-RET fusion gene.

This genomic inversion event was confirmed in the cancer by detecting reads supporting the inversion (8 reads in the liver metastasis; 1 reads in the primary lung cancer). In blood tissue, however, there was no corresponding chromosomal rearrangement in the whole-genome sequencing.

The above findings were further validated using PCR amplification and Sanger sequencing of genomic DNA and cDNA. The PCR reactions were at 95° C. for 10 min, 30 cycles of 95° C. for 30 s, 62° C. for 10 s 72° C. for 10 s and, finally, 72° C. for 10 min. PCR and Sanger sequencing primers for genomic inversion were 5'-CAGAATTTCA-CAAGGAGGGAAG-3' (SEQ ID NO: 18) and 5'-CAG-GACCTCTGACTACAGTGGA-3' (SEQ ID NO: 19). Primers for fusion transcripts are 5'-GTGAAACGTTGCAAGCAGTTAG-3' (SEQ ID NO: 20) and 5'-CCTTGACCACTTTTCCAAATTC-3' (SEQ ID NO: 21). All the Sanger sequencing experiments were performed at Macrogen Inc. (www.macrogen.com).

Figure 10:
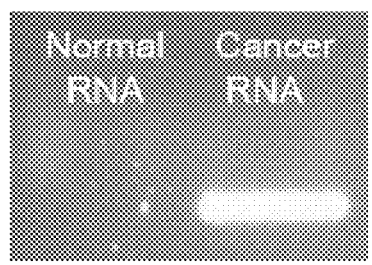
FIG. 10 shows a PCR amplification result for validation of KIF5B-RET fusion gene in RNA of AK55.
Figure 11:
FIG. 11 shows a PCR amplification result for validation of KIF5B-RET fusion gene in DNA of AK55.

All three cancer-related tissues of the patient AK55 (lung cancer, bone and liver metastasis), excluding normal blood, showed PCR products resulting from the inversion event (FIGS. 10 and 11). FIGS. 10 and 11 show the obtained PCR amplification results for validation of KIF5B-RET fusion gene in RNA (FIG. 10) and DNA (FIG. 11) of the patient AK55. The validation of KIF5B-RET fusion gene in RNA and DNA was performed by PCR amplification using inversion-specific primers as described above and electrophoresis. The fusion gene is only detected in the RNA and DNA from the cancer tissue of the patient AK55.

Figure 12:
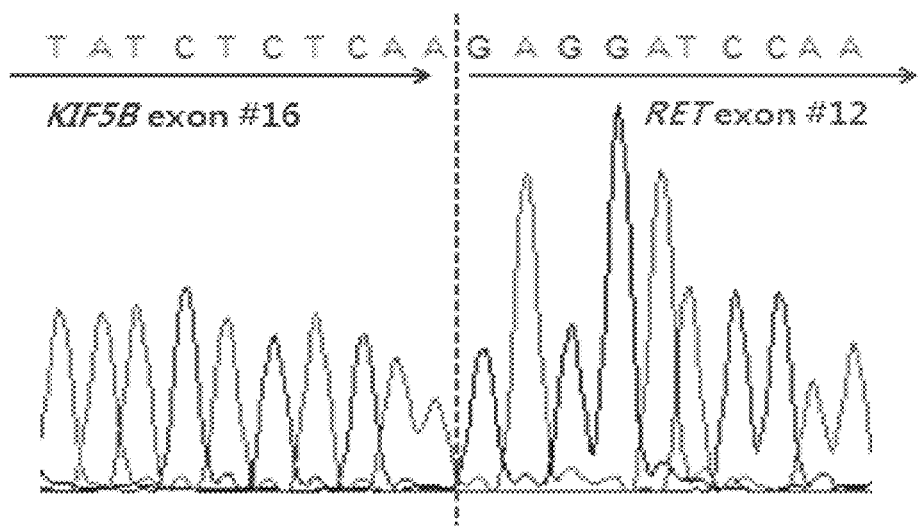
FIG. 12 shows a result of detection of the inversion breakpoint using Sanger sequencing for RNA validation.
Figure 13:
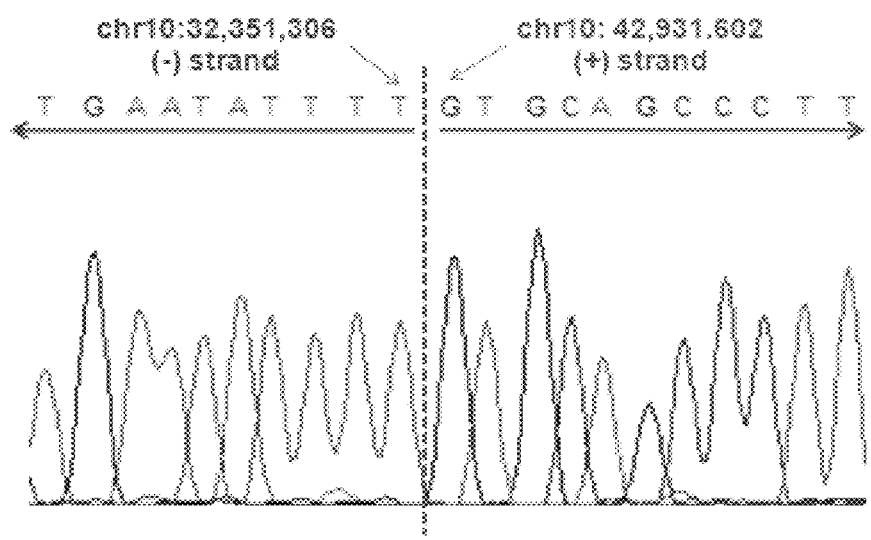
FIG. 13 shows a result of detection of the inversion breakpoint using Sanger sequencing for DNA validation.

Sanger sequencing of these products validated the fusion transcript again as well as finding the breakpoints of the inversion with nucleotide resolution (chr10:32,351,306-42, 931,601 in human reference genome build 36.3). FIGS. 12 and 13 show results of detection of the inversion breakpoint using Sanger sequencing for RNA (FIG. 12) and DNA (FIG. 13) validation. The fusion gene was successfully validated by Sanger sequencing. The inversion breakpoint in the genome was also identified to single-nucleotide resolution. The genomic breakpoints were located in the introns of KIF5B and RET. Two bases downstream from the breakpoint (chr10:42,931,604 in human reference genome build 36.3), a 1-bp deletion was generated, suggesting error-prone non-homologous end joining (NHEJ) might contribute to this inversion event after double-strand DNA breaks.

Interestingly, a single base-pair deletion was identified 2 bp-adjacent to the breakpoint (chr10:42,931,604), suggesting an error-prone DNA repair mechanism, or non-homologous end joining (NHEJ), might have contributed to this inversion event after double-strand DNA breaks. Furthermore, the G-quadruplex (a non-B DNA) structure is predicted in the ~100 bp upstream of the breakpoint in RET, which is known to be fragile and a source of chromosomal translocations.

Example 4: Functional Assessment of KIF5B-RET Fusion Kinase

Figure 14:
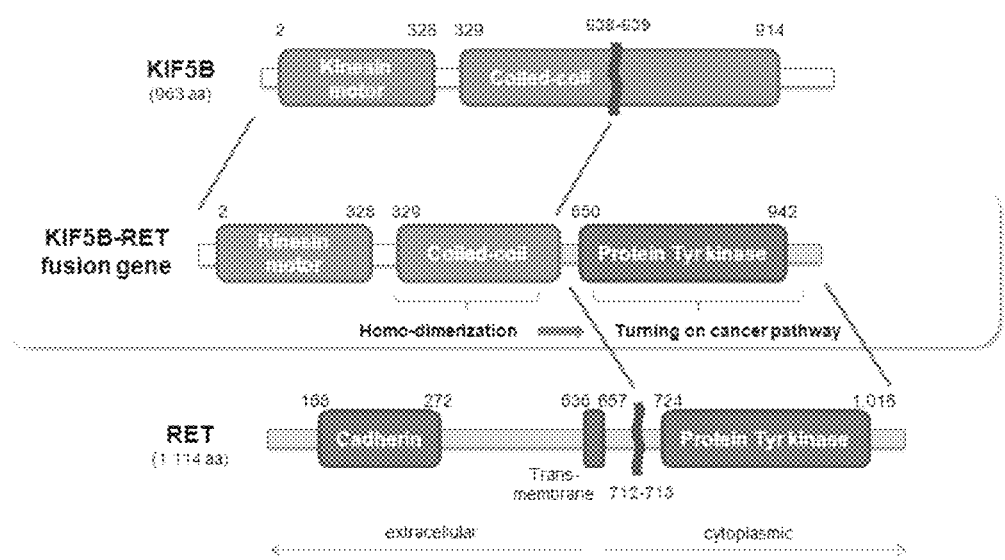
FIG. 14 schematically shows functional domains of KIF5B-RET fusion protein.

The RET oncogene is a transmembrane receptor tyrosine kinase. RET consists of extracellular region (which contains Cadherin-like domains), a trans-membrane domain and an intracellular region containing a tyrosine kinase domain (see FIG. 14). FIG. 14 schematically shows functional domains of KIF5B-RET fusion protein. The fusion protein consists of 638 N-terminal residues of KIF5B and 402 C-terminal residues of RET. The fusion gene has a protein tyrosine kinase domain together with a coiled-coil domain. The coiled-coil domain induces homo-dimerization which will activate the oncogenic protein tyrosine kinase domain by auto-phosphorylation.

When RET is dimerized by binding co-receptors and ligands, such as glial derived neurotrophic factor (GDNF), it is activated by auto-phosphorylation and then simulates downstream signaling pathways. The downstream signaling cascade of the RET proto-oncogene is the mitogen-activated protein kinase (MAPK) pathway, which regulates cell survival/apoptosis, proliferation, differentiation, and migration. The normal expression of RET is important for neuronal development, but it is known to not be activated in differentiated tissues.

KIF5B is a microtubule-based motor protein, ubiquitously expressed due to its active promoter and involved in the transport of organelles in eukaryotic cells. Its coiled-coil domain induces homo-dimerization, which is essential for its movement.

Figure 15:
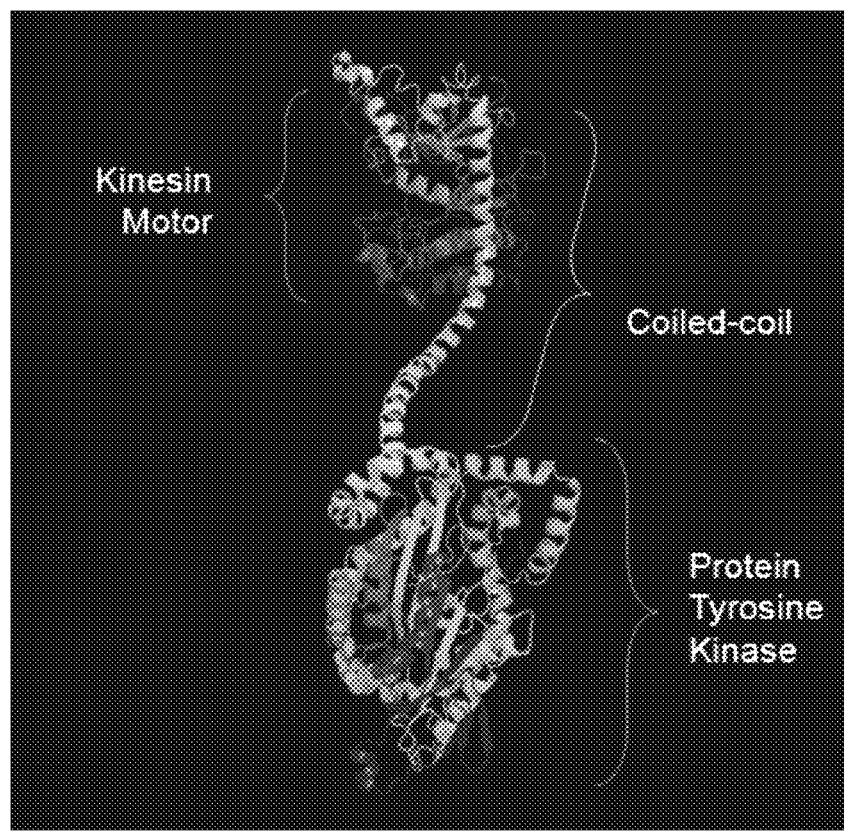
FIG. 15 shows a three-dimensional structure of KIF5B-RET fusion protein as predicted by the PHYRE2 algorithm.

FIG. 15 shows a three-dimensional structure of KIF5B-RET fusion protein as predicted by the PHYRE2 algorithm. The N- and C-terminal of the fusion protein are colored in red and blue, respectively. Protein 3D modeling was performed using Phyre2 software using the protein sequence of the KIF5B-RET fusion gene (www.sbg.bio.ic.ac.uk/phyre2).

Figure 16:
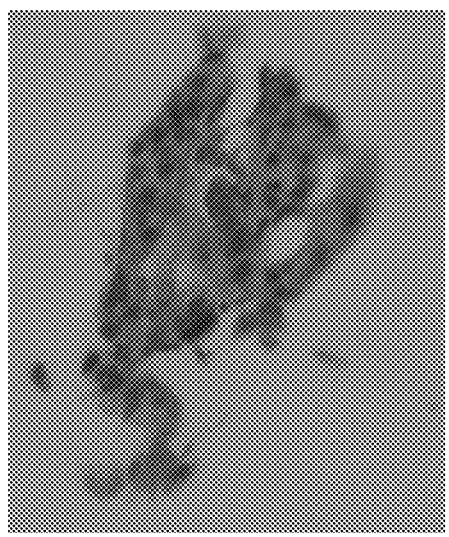
FIG. 16 is a microscopic image showing a result of immunohistochemical analysis of KIF5B-RET expression in the lung cancer (bone metastasis) obtained from a patient (AK55) (×400).

Taken together, the KIF5B-RET fusion gene may be highly expressed and then dimerized after translation owing to KIF5B (FIGS. 14 and 15). Then, the dimerized RET protein tyrosine kinase domain may be stimulated abnormally, thus facilitating the stimulation of an oncogenic pathway. Immunohistochemical analysis showed that the tyrosine kinase domain of RET was highly expressed in the lung cancer tissue (FIG. 16). FIG. 16 is a microscopic image showing a result of immunohistochemical analysis of KIF5B-RET expression in the lung cancer (bone metastasis) obtained from a patient (AK55) (×400). The protein is exclusively observed in tumor cells, suggesting the KIF5B-RET fusion protein has important roles in the cancer.

Example 5: Frequency Assessment of RET Overexpression in Other Lung Cancer Samples The oncogenic effect of RET was first identified in papillary thyroid carcinoma (PTC) where diverse kinds of chromosomal translocations and inversions led to the formation of PTC/RET fusion genes. Specific point mutations have also been reported as drivers in multiple endocrine neoplasia (MEN) types 2A and 2B. In addition, activated RET has been observed in prostate cancer, pancreatic cancer and melanoma. Its tumorigenecity is also supported by RET transgenic mice studies which generated a variety of malignancies. However, this gene has not been highlighted in lung cancer previously.

The frequency of RET overexpression in lung adenocarcinoma was evaluated using previous microarray data archived in databases. In particular, to investigate the RET overexpression in general lung adenocarcinoma, we analyzed the expression profile of lung adenocarcinoma archived in databases (Gene Expression Omnibus: www.ncbi.nlm.nih.gov/geo and The Cancer Genome Atlas (TCGA): www.cancergenome.nih.gov).

Figure 17:
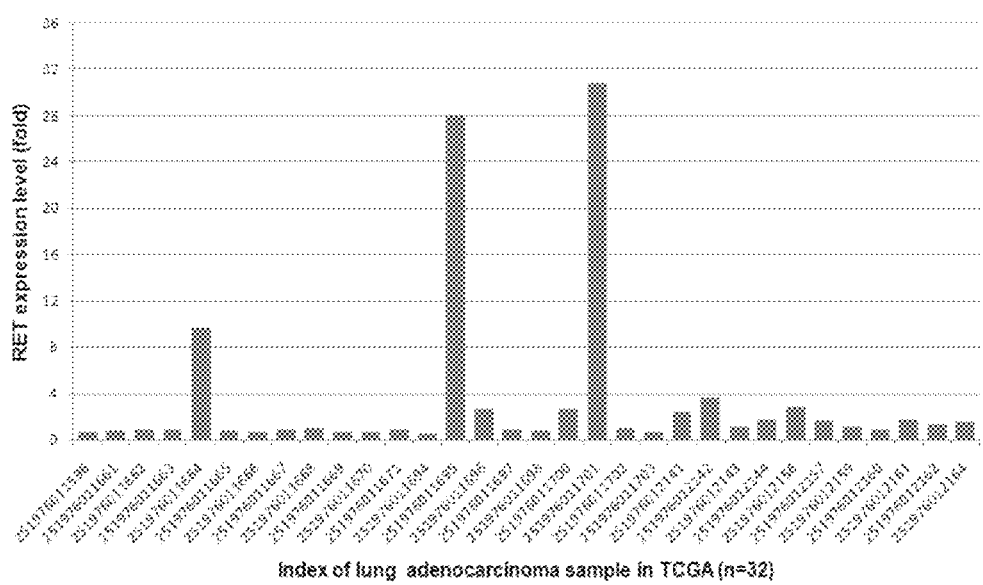
FIG. 17 is a graph showing the results of analysis of RET expression in other lung adenocarcinomas.

Expression profiling of ten adenocarcinoma cell lines (Gemma A, Li C, Sugiyama Y, et al., BMC Cancer 2006; 6:174) showed two samples highly expressing RET. On the other hand, RET was not activated in ten small cell cancer cell lines and nine squamous cell carcinoma cell lines in this dataset. We found a further 3 studies which profiled RET proto-oncogene expression in primary lung cancer. In the dataset of the first study (Ding L, Getz G, Wheeler D A, et al., Nature 2008; 455:1069-75), 6 of the 75 tumors (8%) overexpressed RET. Another dataset (Kuner R, Muley T, Meister M, et al., Lung Cancer 2009; 63:32-8) showed RET activation in 5 out of 40 samples (12.5%). Finally, The Cancer Genome Atlas (TCGA) dataset showed RET overexpression in 3 out of 32 samples (9.4%; FIG. 17). FIG. 17 is a graph showing the results of analysis of RET expression in other lung adenocarcinomas. The expression microarray data of 32 lung adenocarcinomas deposited in TCGA (The Cancer Genome Atlas) were analyzed. Of these, 3 samples showed clear overexpression of RET, suggesting the frequency of overexpression in lung adenocarcinoma is approximately 10%.

Taken together, these results suggest that the frequency of RET overexpression is ~10% in lung adenocarcinoma.

Figure 18:
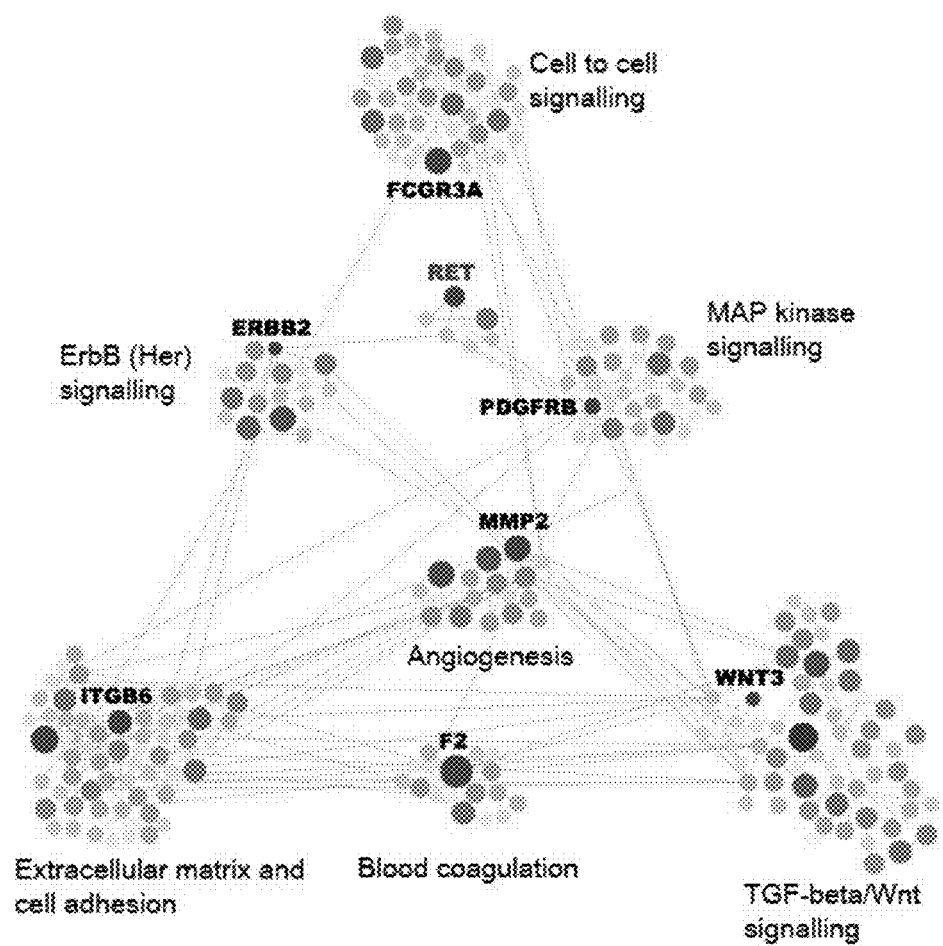
FIG. 18 shows a result of network analysis of gene expression in the liver metastasis.

FIG. 18 shows a result of network analysis of gene expression in the liver metastasis. The network analysis was done using Cytoscape (www.cytoscape.org) along with MiMl plugin (www.miniplugin.ncibi.org). Genes overexpressed in the cancer were mapped as a network, where the node size is proportional to the relative expression. Major functional groups were labeled. Functionally important genes were colored in red.

Example 6: Identification of KIF5B-RET Fusion Gene by FISH Analysis

Figure 19:
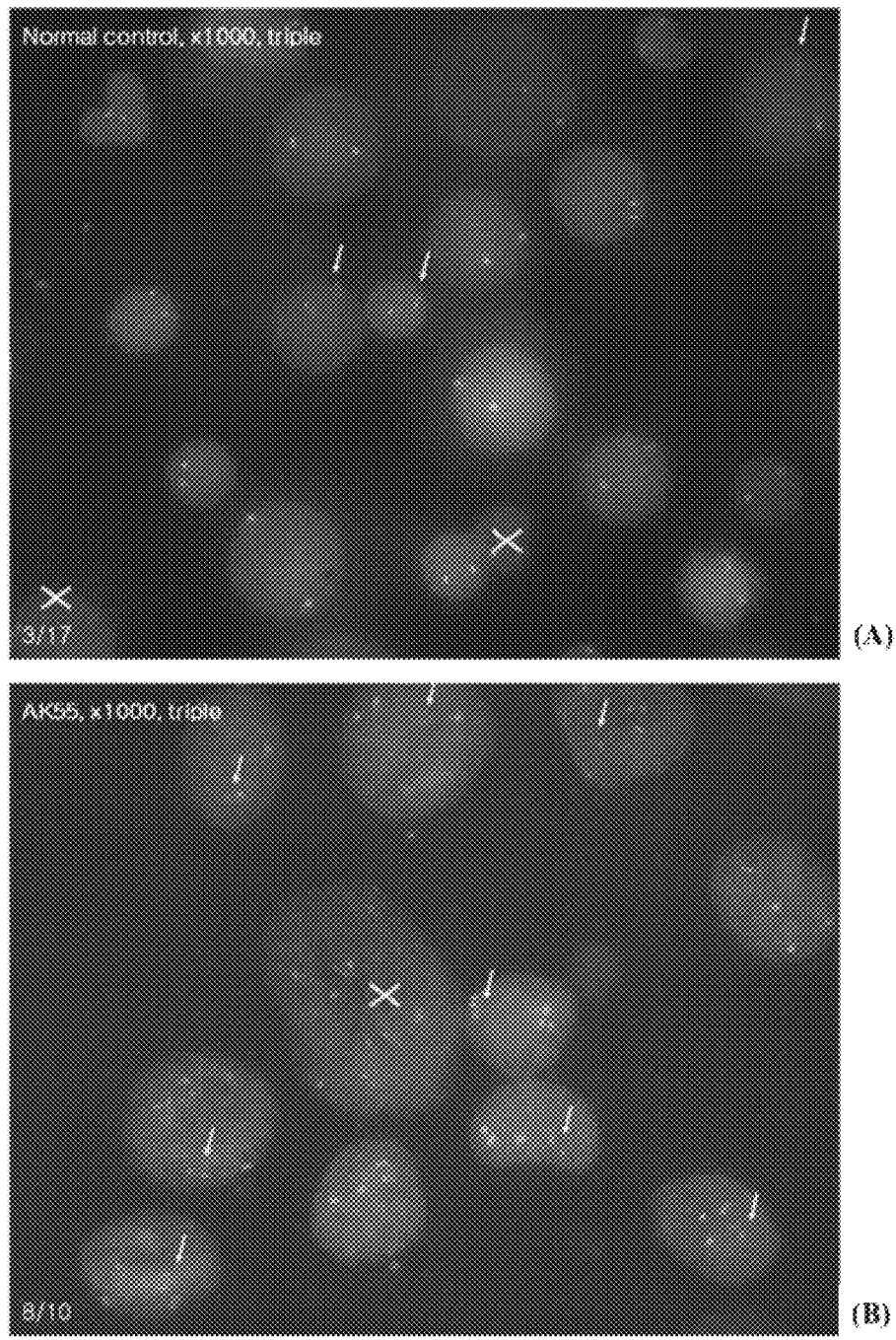
FIG. 19 shows results of FISH analysis for normal cell (A) and lung cancer cell (B).

To identify RET rearrangements, fluorescent in situ hybridization (FISH) was performed on AK55 cell lines and normal cell as a control by using a break-apart probe for RET. The slides were immersed in Citrisolve (Fisher Scientific, Pittsburgh, Pa.) for 15 minutes, jet air dried, immersed in Lugol solution for 5 minutes, and immersed in 2.5% sodium thiocyanate for 30 seconds. The slides were then placed in 10 mmol/L of citrate/citric acid solution (pH 6.0) and microwaved on the high setting for 5 minutes, followed by 15 to 45 minutes in 0.4% pepsin solution (pepsin A/0.9% sodium chloride at pH 1.5) at 37° C. Ten microliters of FISH reagent (7 μL LSI buffer [Vysis, Downers Grove, Ill.] and 3 μL probe) were placed on each slide, and the slides were coverslipped, denatured in a Hybrite (Vysis) set at a melt temperature of 80° C. for 5 minutes, and incubated in a humidified chamber at 37° C. for 12 hours. The slides were then washed in 2× saline sodium citrate/ 0.1% NP40 (US Biological, Swampscott, Mass.) at 70° C. for 2 minutes and counterstained with 49,6-diamidino-2-phenyl indole dihydrochloride. The cells were analyzed by a microscopist (M. L.) using a fluorescent microscope equipped with appropriate filter sets. Chromosome inversion, a deduced chromosomal rearrangement is responsible for KIF5B-RET fusion. The obtained results of FISH are shown in FIG. 19, showing a split of red and green probes that flank the RET translocation site in a KIF5B-RET fusion positive tumor (arrows).

Figure 20:
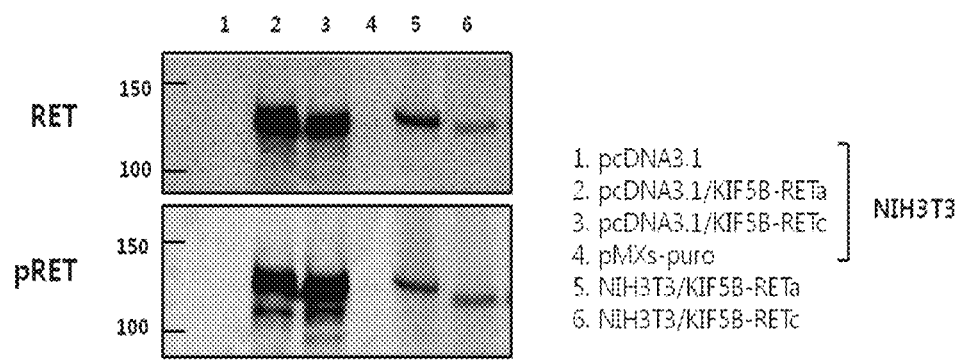
FIG. 20 shows western blotting results of NIH3T3 cell line showing the expression of KIF5B-RET fusion protein in NIH3T3 cell line.

Example 7: Examination of Cell Growth Rate and Viability of a Mammal Cell Transfected with KIF5B-RET Fusion Gene By transfecting NIH 3T3 cells with a construct including cDNA encoding KIF5B-RET fusion protein and expressing the KIF5B-RET fusion protein, it was confirmed whether or not the expression of the KIF5B-RET fusion protein contributes to conversion from normal cell to tumor cell. NIH 3T3 cells (ATCC/ATCC Number CRL-1658) were maintained in DMEM medium (Gibco BRL) supplemented with 10% (v/v) fetal bovine serum (FBS; Gibco BRL), penicillin, and streptomycin. Preparation of supernatant of retrovirus and transfection were performed according to protocol provided by Platinum Retrovirus Expression System purchased from CELL BIOLABs. NIH3T3 cells were transduced with the supernatant of retrovirus including a pMXs-puro/fusion protein expression vector, and then the transducted cells were selected using puromycin (2 ug/ml). Whole cell lysates from cell lines were subjected to SDS-PAGE followed by blotting onto a polyvinylidine difluoride (PVDF) membrane. The blot were blocked TBS containing 0.1% Tween 20 and 5% BSA, and probed with anti-RET (#3223, Cell signaling, USA), anti-phospho-RET (Tyr905) (#3221, Cell signaling, USA), and anti-actin (A5441, Sigma-Aldrich, USA). After washing with TBS containing 0.1% Tween 20, the membrane were incubated with horseradish peroxidase-conjugated anti-mouse or anti-rabbit secondary antibodies and treated with an enhanced chemiluminescence reagent (Pierce, #34080). The obtained results are shown in FIG. 20, indicating that the selected NIH3T3 cells are stably transformed with KIF5B-RET fusion gene through western blotting.

Figure 21:
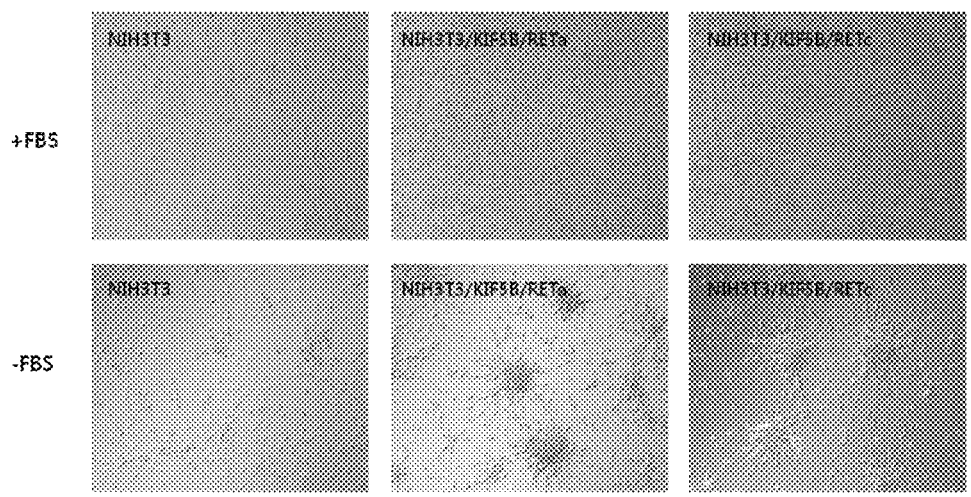
FIG. 21 shows the colony forming ability of NIH3T3 cell line transfected with KIF5B-RET fusion gene.

The growth rates of NIH3T3 parent cells and NIH3T3 stable cell lines expressing KIF5B-RETa, or KIF5B-RETc fusion gene (NIH3T3/KIF5B-RETa, NIH3T3/KIF5B-RETc) cells in FBS-containing or FBS-free medium were measured and compared with each other. The NIH3T3 cell and NIH3T3/KIF5B-RET cells were cultured with FBS containing media, or FBS-free media for 24 hour. And then, the obtained images are shown in FIG. 21. As shown in FIG. 21, the growth of non-transfected NIH3T3 cells is inhibited in FBS-free medium, but KIF5B-RET fusion gene transformed NIH3T3 cells grow and form colonies well even in FBS-free medium. These results indicate that the expression of KIF5B-RET fusion protein converts NIH3T3 cells properties and KIF5B-RET fusion gene transfected cells are capable of survival and growth even under the abnormal conditions such as FBS deficient medium owing to the KIF5B-RET fusion protein.

Example 8: Examination of Inhibition of Mammal Solid Tumor Cell Growth by the Fusion Protein Inhibitor (Cabozantinib)

To confirm the effects of the fusion protein to stimulate growth and survival of cell lines (or tumor cells) expressing the fusion protein, the cell lines were treated with a inhibitor against a kinase or other domain in the fusion protein.

Figure 22:
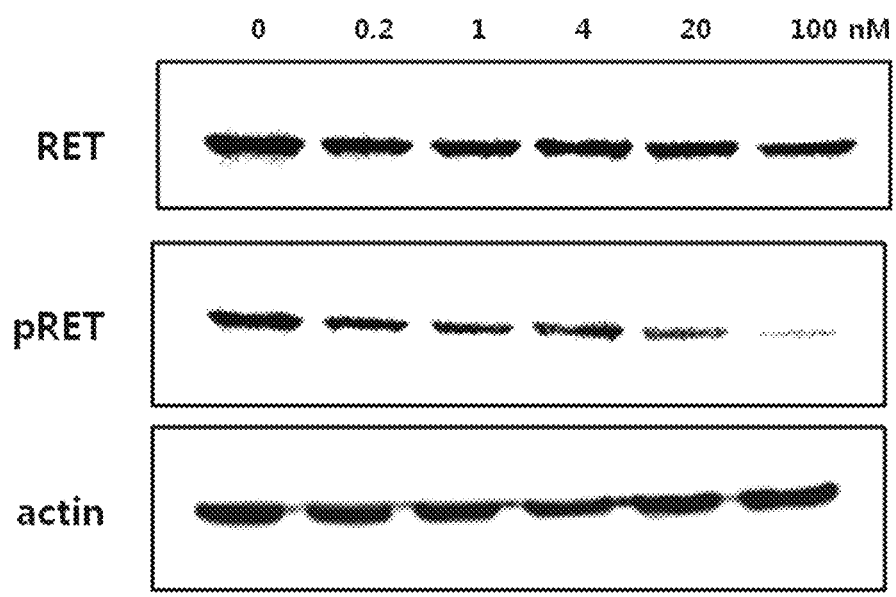
FIG. 22 shows the protein expression level in NIH3T3 cell line transfected with KIF5B-RET fusion gene under the treatment of a kinase inhibitor, Cabozantinib.

Specifically, KIF5B-RET transfected NIH3T3 cells (NIH3T3/KIF5B-RET) (referring to Example 7) were treated with cabozantinib (4 Chem, Korea) in various concentrations for 2 days as shown in FIG. 22, and the expression levels of RET, phospho-RET, and actin (control) were measured by immunoblotting using corresponding antibodies. Anti-RET and anti-phospho-RET (Tyr905) antibodies were obtained from Cell Signaling Technology (#3223, #3221). Anti-actin antibody were obtained from Sigma Aldrich (#A5441).

The obtained results are shown in FIG. 22 showing that the expression of phospho-RET, which is an active form of RET, is decreased depending on the concentration of cabozantinib. These results indicate that the RET protein is abnormally activated in the fusion protein transfected cells, and the growth of the fusion protein transfected cells can be inhibited by treating a kinase inhibitor.

Figure 23:
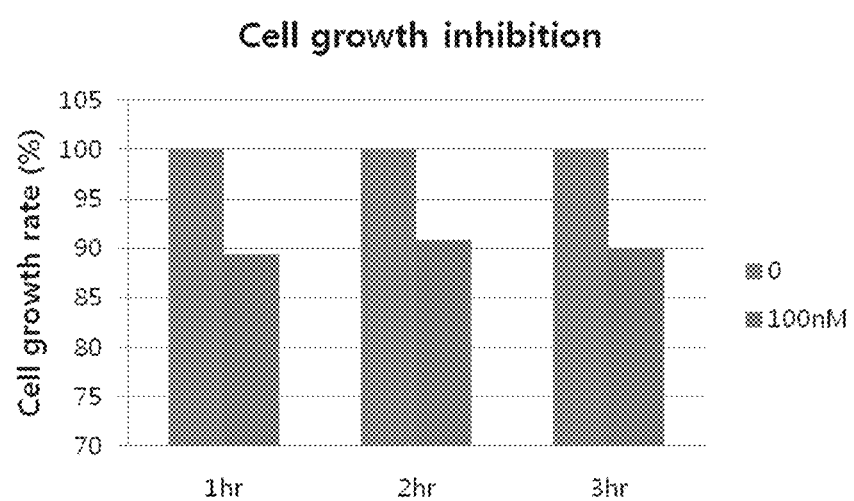
FIG. 23 is a graph showing the cell growth rate of KIF5B-RET fusion protein expressing cell under the treatment of a kinase inhibitor, Cabozantinib.

To quantitatively analyze such cell growth inhibition, the number of cells expressing the fusion protein is counted, and the cell growth inhibition was analyzed using WST-1 solution cell proliferation assay (Roche) according to protocol provided by the manufacturer. About 1000 to 5000 cells of the KIF5B-RET transfected NIH3T3 cells were seeded on 96-well plate, and grown in complete medium (DMEM, Gibco) supplemented with 10% (v/v) FBS. After 24 hours, the medium was replaced with 100 µl of complete growth medium supplemented with 10% (v/v) FBS and cabozantinib in 100 nM concentrations as shown in FIG. 23, and then, the cells were further cultured for 72 hours. At end point of the cell culture, each well was added with 10 µl of WST-1 solution and further cultured for 1 to 3 hours. Absorbance at 450 nm was measured using a microplate reader. The growth inhibition was evaluated as mean±SD value of the measured absorbance of cabozantinib treated cells compared with that of non-treated cells. The analyses were performed in triplicate. The obtained results are shown in FIG. 23. As shown in FIG. 23, the KIF5B-RET fusion protein contributes to increase of cell growth rate and cell survival of human tumor cells (such as NSCLC), and the inhibitor against the fusion protein is capable of leading to deceased cell survival and increased apoptosis.

Example 9: Detection of KIF5B-RET Fusion Gene in Other Patients

In order to show that the KIF5B-RET fusion gene also exists in other primary lung adenocarcinomas, a transcriptome of additional triple-negative (EGFR, KRAS, and EML4-ALK) primary lung adenocarcinoma was analyzed using massively parallel sequencing. The additional sample was called as LC_S2 (A 62-year-old man patient received a diagnosis of lung adenocarcinoma stage 3A). The sample of LC_S2 was prepared referring to the method described in Example 1. KIF5B-RET fusion transcripts were found in LC_S2. As in AK55, RET was highly expressed from $12^{th}$ exon in LC_S2 as shown in Table 4.

TABLE 4

Exon-by-exon RET expression

| gene | accession | chrom | exon | start | end | length | strand | AK55 | LC_S2 |
|---|---|---|---|---|---|---|---|---|---|
| RET | NM_020630 | 10 | exon1 | 43572516 | 43572779 | 263 | + | 0.03 | 0.10 |
| RET | NM_020630 | 10 | exon2 | 43595906 | 43596170 | 264 | + | 0.00 | 0.38 |
| RET | NM_020630 | 10 | exon3 | 43597789 | 43598077 | 288 | + | 0.18 | 0.68 |
| RET | NM_020630 | 10 | exon4 | 43600399 | 43600641 | 242 | + | 0.08 | 0.41 |
| RET | NM_020630 | 10 | exon5 | 43601823 | 43602019 | 198 | + | 0.07 | 0.32 |
| RET | NM_020630 | 10 | exon6 | 43604478 | 43604678 | 200 | + | 0.24 | 0.33 |
| RET | NM_020630 | 10 | exon7 | 43606654 | 43606913 | 259 | + | 0.14 | 0.43 |
| RET | NM_020630 | 10 | exon8 | 43607546 | 43607672 | 126 | + | 0.11 | 0.00 |
| RET | NM_020630 | 10 | exon9 | 43608300 | 43608411 | 111 | + | 0.26 | 0.27 |
| RET | NM_020630 | 10 | exon10 | 43809003 | 43609123 | 120 | + | 0.40 | 0.58 |
| RET | NM_020630 | 10 | exon11 | 43609927 | 43610184 | 257 | + | 0.24 | 0.66 |
| RET | NM_020630 | 10 | exon12 | 43612031 | 43612179 | 148 | + | 4.25 | 12.50 |
| RET | NM_020630 | 10 | exon13 | 43613820 | 43613928 | 108 | + | 5.82 | 7.74 |
| RET | NM_020630 | 10 | exon14 | 43614978 | 43615193 | 215 | + | 4.49 | 8.41 |
| RET | NM_020630 | 10 | exon15 | 43615528 | 43615651 | 123 | + | 7.13 | 14.60 |
| RET | NM_020630 | 10 | exon16 | 43617293 | 43617464 | 71 | + | 7.45 | 17.86 |
| RET | NM_020630 | 10 | exon17 | 43619118 | 43619256 | 138 | + | 8.94 | 18.15 |
| RET | NM_020630 | 10 | exon18 | 43820330 | 43620430 | 100 | + | 8.06 | 15.81 |
| RET | NM_020630 | 10 | exon19 | 43622022 | 43622952 | 930 | + | 8.21 | 8.37 |

Because KIF5B is generally expressed in differentiated tissue, the KIF5B-RET fusion gene could be expressed by the active promoter of KIF5B in those lung cancer tissues (AK55 and LC_S2). This fusion transcript in LC_S2 was validated using cDNA PCR.

Figure 24:
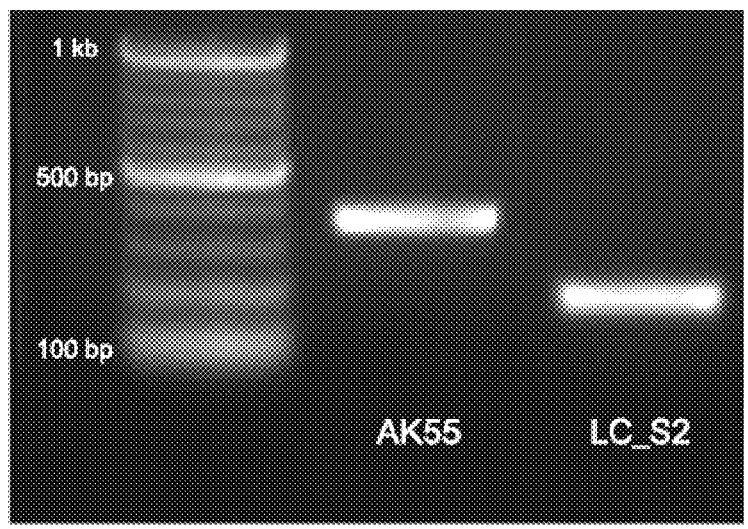
FIG. 24 is a gel electrophoresis image of liver metastatic lung cancer (AK55) and triple-negative lung adenocarcinoma (LC_S2).

The obtained validating data for AK55 and LC_S2 are shown in FIG. 24. FIG. 24 shows the results of analysis using cDNA PCR targeting KIF5B-RET fusion transcripts and gel electrophoresis in the liver metastatic lung cancer of AK55 and the additional triple-negative lung adenocarcinoma (LC_S2). cDNA from AK55 (SEQ ID NO: 1) and LC_S2 (SEQ ID NO: 9) shows clear evidence of the fusion transcript. Because the fusion transcript in AK55 contains one more exon of KIF5B (exon 16) compared with that in LC_S2 (exon 15), the size of the PCR product in AK55 is longer than that in LC_S2.

In addition, the KIF5B-RET fusion gene was further assessed using cDNA PCR of a double-negative (EGFR and EML4-ALK were negative in pathologic studies; KRAS mutation status was unknown) primary lung adenocarcinoma (LC_S6) (A 58-year-old man patient received a diagnosis of lung adenocarcinoma stage 1A). The sample of LC_S2 was prepared referring to the method described in Example 1. The fusion transcript in LC_S2 was validated using cDNA PCR, confirming that LC_S6 showed the KIF5B-RET fusion gene (SEQ ID NO: 13) (FIG. 25). FIG. 25 shows the results of validation using cDNA PCR targeting KIF5B-RET fusion transcripts and gel electrophoresis in double-negative lung adenocarcinoma (LC_S6). LC_S6 shows clear evidence of the fusion transcript. The fusion transcript in LC_S6 contains seven more exons of KIF5B (exons 17-23) compared with that in AK55.

Figure 25A:
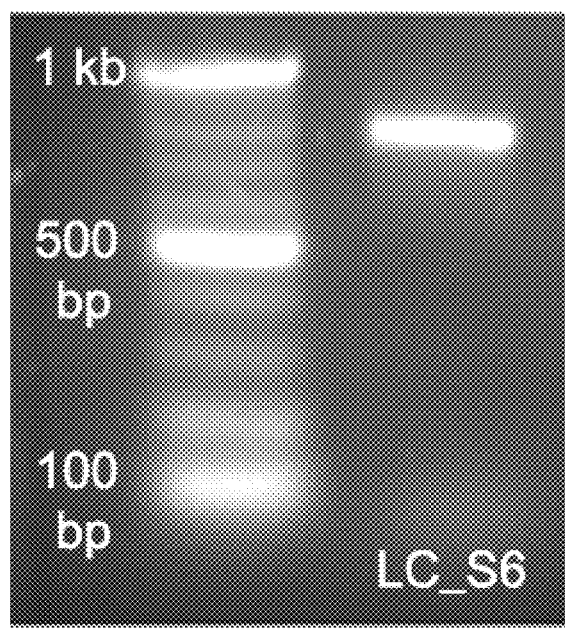
FIG. 25A is a gel electrophoresis image of double-negative lung adenocarcinoma (LC_S6).
Figure 25B:
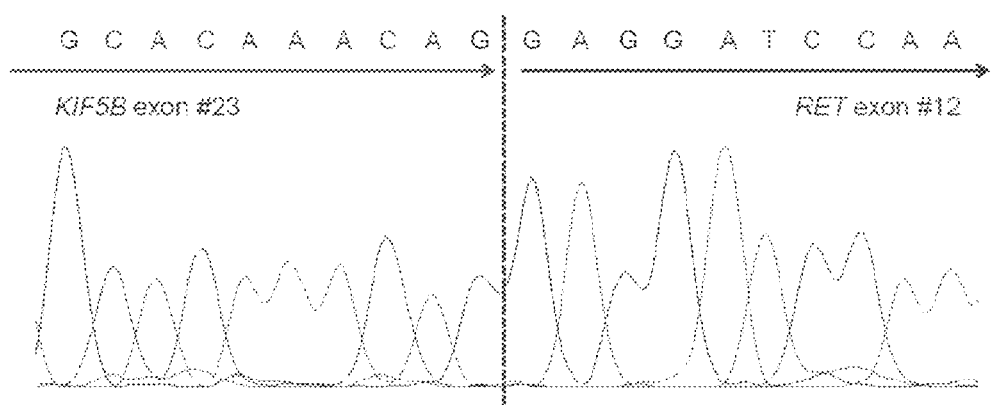
FIG. 25B is results of Identification of breakpoint of the KIF5B-RET fusion gene in LC_S6 using Sanger sequencing.

The breakpoint of the fusion gene in LC_S6 was identified using Sanger sequencing, and the obtained results are shown in FIG. 25B.

The validations relating to FIGS. 24, 25A and 25B were performed using PCR amplification and Sanger sequencing of genomic DNA and cDNA. The PCR reactions were 10 min at 95° C.; 30 cycles of 30 sec at 95° C., 10 sec at 62° C. and 10 sec at 72° C.; and, finally, 10 min at 72° C. PCR and Sanger sequencing primers for genomic inversion of AK55 were 5'-CAGAATTTCACAAGGAGGGAAG-3' (KIF5B; SEQ ID NO: 18) and 5'-CAGGACCTCTGACTA-CAGTG GA-3' (RET; SEQ ID NO: 19). The primers for the fusion transcripts were 5'-GTGAAACGTTGCAAGCAGT-TAG-3' (KIF5B; SEQ ID NO: 20; for AK55 and LC_S6) and 5'-CCTTGACCACTTTTCCAAATTC-3' (RET; SEQ ID NO: 21; or AK55, LC_S2 and LC_S6). For cDNA PCR in replication studies, a different KIF5B primer (5'-TAAGGAAATGACCAACCACCAG-3'; SEQ ID NO: 22) was used for LC_S2, since the KIF5B fusion breakpoint in LC_S2 was different to that in AK55. All the Sanger sequencing experiments were performed at Macrogen Inc. (www.macrogen.com).

Overall, we identified two more cases of the KIF5BRET fusion gene (LC_S2 and LC_S6) in primary lung adenocarcinomas in the replication study. These results clearly show that KIF5B-RET fusion is not rare and that the fusion transcript generally exists in the primary lung adenocarcinomas. In addition, because it would be very unlikely to find identical nonfunctional fusion genes in different cancer tissues, these results also provide indirect evidence that the expression of the KIF5B-RET fusion gene has an important functional impact in lung cancer.

Figure 26:
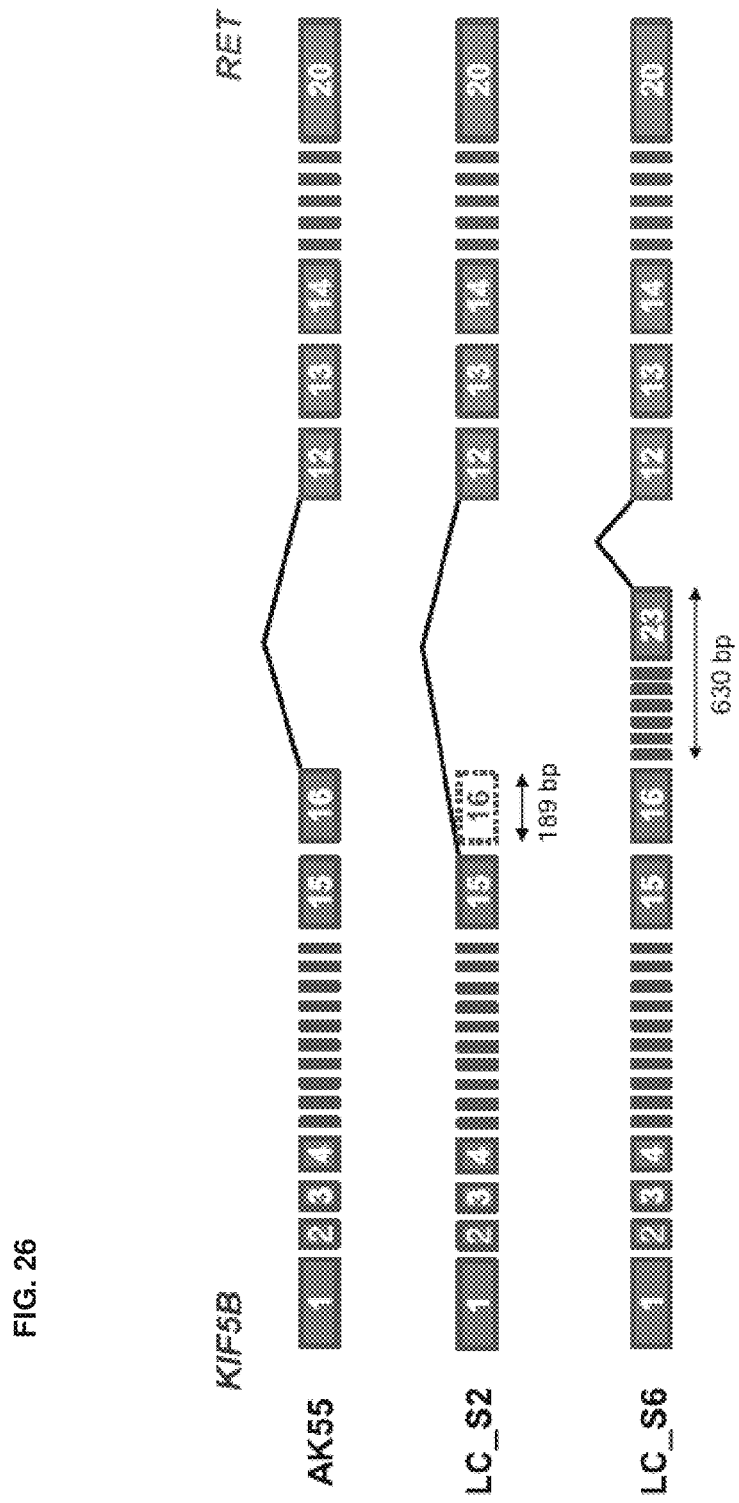
FIG. 26 schematically shows KIF5B-RET fusion transcripts of AK55, LC_S2, and LC_S6.

Interestingly in LC_S2 and LC_S6, exon 12 of RET was joined to exon 15 (LC_S2) and exon 23 (LC_S6) instead of to exon 16 of KIF5B as in AK55 (FIG. 26). FIG. 26 schematically shows KIF5B-RET fusion transcripts of AK55 (SEQ ID NO: 1), LC_S2 (SEQ ID NO: 9), and LC_S6 (SEQ ID NO: 13). Each rectangle indicates an exon of KIF5B (blue) and RET (red) gene.

These suggest that the double-strand breaks of DNAin KIF5B may not be consistent among primary lung cancers. However, because their coiled-coil domains are well preserved in the KIF5B-RET chimeric oncogene in both the samples (the length of coiled-coil domain in the fusion gene was 247 and 520 amino acids in LC_S2 and LC_S6, respectively), the dimerization activity is probably not very different compared with that of AK55 (310 amino acids).

The KIF5B-RET fusion genes and KIF5B-RET fusion proteins obtained from lung adenocarcinoma samples (AK55, LC_S2, and LC_S6) are summarized in the Table 4:

TABLE 4

|  |  | KIF5B (NM_004521) | RET (NM_020975) | size |
|---|---|---|---|---|
| AK55 | nucleotide | 1914 nt | 1209 nt | 3123 nt |
|  | Amino acid | 638 a.a | 402 a.a | 1040 a.a |
|  | exon | 1-16 exon | 12-20 exon | 25 exon |
| LC-S2 | nucleotide | 1725 nt | 1209 nt | 2934 nt |
|  | Amino acid | 575 a.a | 402 a.a | 977 a.a |
|  | exon | 1-15 exon | 12-20 exon | 24 exon |

TABLE 4-continued

|  |  | KIF5B (NM_004521) | RET (NM_020975) | size |
|---|---|---|---|---|
| LC-S6 | nucleotide | 2544 nt | 1209 nt | 3753 nt |
|  | Amino acid | 848 a.a | 402 a.a | 1250 a.a |
|  | exon | 1-23 exon | 12-20 exon | 32 exon |

What is claimed is:

1. A method of diagnosing lung adenocarcinoma in a subject, the method comprising:
    (a) detecting a fusion gene having SEQ ID NO:1 encoding a fusion protein KIF5B-RET in a test sample obtained from the subject;
    (b) determining that the subject is a lung adenocarcinoma patient when the fusion gene encoding the fusion protein KIF5B-RET is detected in the test sample,
    wherein the fusion gene encoding the fusion protein KIF5B-RET is detected by using a primer pair of 5'-GTGAAACGTTGCAAGCAGTTAG-3' (SEQ ID NO: 20) and 5'-CCTTGACCACTTTTCCAAATTC-3' (SEQ ID NO: 21).

2. The method according to claim 1, wherein the fusion gene encoding the fusion protein KIF5B-RET is further detected and validated by using the integration of whole-transcriptome (RNA) and whole-genome (DNA) sequencing through massively parallel sequencing technologies.

3. A method of diagnosing lung adenocarcinoma in a subject, the method comprising:
    (a) detecting a fusion gene having SEQ ID NO: 13 encoding a fusion protein KIF5B-RET in a test sample obtained from the subject;
    (b) determining that the subject is a lung adenocarcinoma patient when the fusion gene encoding the fusion protein KIF5B-RET is detected in the test sample,
    wherein the fusion gene encoding the fusion protein KIF5B-RET is detected by using a primer pair of 5'-GTGAAACGTTGCAAGCAGTTAG-3' (SEQ ID NO: 20) and 5'-CCTTGACCACTTTTCCAAATTC-3' (SEQ ID NO: 21).

4. The method according to claim 3, wherein the fusion gene encoding the fusion protein KIF5B-RET is further detected and validated by using the integration of whole-transcriptome (RNA) and whole-genome (DNA) sequencing through massively parallel sequencing technologies.

* * * * *